US006379928B1

(12) United States Patent
Berka et al.

(10) Patent No.: US 6,379,928 B1
(45) Date of Patent: *Apr. 30, 2002

(54) HETEROLOGOUS POLYPEPTIDES EXPRESSED IN FILAMENTOUS FUNGI, PROCESSES FOR MAKING SAME, AND VECTORS FOR MAKING SAME

(75) Inventors: Randy Michael Berka, San Mateo, CA (US); Daniel Cullen, Madison, WI (US); Gregory Lawrence Gray, South San Francisco, CA (US); Kirk James Hayenga, Burlingame, CA (US); Virgil Bryan Lawlis, San Mateo, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/468,265

(22) Filed: Dec. 10, 1999

Related U.S. Application Data

(63) Continuation of application No. 08/484,384, filed on Jun. 7, 1995, now Pat. No. 6,004,785, which is a continuation of application No. 08/284,942, filed on Aug. 2, 1994, now Pat. No. 5,578,463, which is a continuation of application No. 07/413,010, filed on Sep. 25, 1989, now Pat. No. 5,364,770, which is a continuation of application No. 07/163,219, filed on Feb. 26, 1988, now abandoned, which is a continuation of application No. 06/882,224, filed on Jul. 7, 1986, now abandoned, which is a continuation-in-part of application No. 06/771,374, filed on Aug. 29, 1985, now abandoned.

(51) Int. Cl.[7] .......................... C12P 21/00; C12N 15/00; C12N 9/00; C12N 1/15

(52) U.S. Cl. ................. 435/71.1; 435/69.1; 435/69.7; 435/69.8; 435/183; 435/205; 435/223; 435/225; 435/254.11; 435/254.3; 435/254.4; 435/254.6; 435/254.8

(58) Field of Search ................... 435/69.1, 69.7, 435/69.8, 71.1, 183, 205, 223, 225, 254.11, 254.3, 254.4, 254.6, 254.8, 320.1; 536/23.1, 23.2, 23.74

(56) References Cited

U.S. PATENT DOCUMENTS

| | | | |
|---|---|---|---|
| 4,486,533 A | | 12/1984 | Lambowitz |
| 4,492,758 A | | 1/1985 | Esser et al. |
| 4,666,847 A | | 5/1987 | Alford et al. |
| 4,794,175 A | | 12/1988 | Nunberg et al. |
| 4,816,405 A | | 3/1989 | Yelton et al. |
| 4,863,864 A | | 9/1989 | Ashikari et al. |
| 5,198,345 A | | 3/1993 | Gwynne et al. |
| 5,578,463 A | * | 11/1996 | Berka et al. |
| 6,004,785 A | * | 12/1999 | Berka et al. |
| 6,103,490 A | * | 8/2000 | Berka et al. |
| 6,171,817 B1 | * | 1/2001 | Berka et al. |

FOREIGN PATENT DOCUMENTS

| | | |
|---|---|---|
| EP | 0077109 | 4/1983 |
| EP | 0126206 | 11/1984 |
| EP | 0171218 | 2/1986 |
| EP | 0184438 | 6/1986 |
| EP | 0238023 | 9/1987 |
| EP | 0249350 | 12/1987 |
| WO | 8603774 | 7/1986 |
| WO | 8606097 | 10/1986 |

OTHER PUBLICATIONS

Stohl, L. L., et al., "Construction of a shuttle vector for the filamentous fungus Neurospora crassa" Proc. natl. Acad. Sci. USA, 80:1058–1062 (1983).
Ballance, D. J., et al., "Transformation of Aspergillus nidulans by the Orotidine–5' –Phosphate Decarboxylase Gene," Biochemical and Biophysical Research Communications, 112(1):284–289 (1983).
Tilburn, J., et al., "Transformation by integration in Aspergillus nidulans," Gene, 26:205–221 (1983).
Yelton, M.M., et al., "Transformation of Aspergillus nidulans by using a trpC plasmid," Proc. Natl. Acad. of Sci. USA, 81:1470–1474 (1984).
Kück, U., et al., "II. Recombination: a) DNA Transformation in Cyanobacteria, Algae and Fungi: Trends and Perspectives," Progress in Botany, 46:201–204 (1984).
Krieg et al., J. Mol. Biol., 180:615–640 (1984).
Warren et al., Cell, 30 (2):547–555 (1984).
Innis et al., (1965) Science, vol. 228, pp. 21–26.
Boel et al., EMBO J., 3(5):1097–1102 (May 1984).
Mellor et al., Gene, 24:1–14 (Sep. 1983).
Stohl, L. L., et al., "Characterization of deletion derivatives of an autonomously replicating Neurospora plasmid," Nucleic Acids Research, 12:6169–6178 (1984).

(List continued on next page.)

Primary Examiner—Andrew Wang
Assistant Examiner—Mark L. Shibuya
(74) Attorney, Agent, or Firm—Richard F. Trecartin; Flehr Hohbach Test Albritton & Herbert LLP

(57) ABSTRACT

Novel vectors are disclosed for expressing and secreting heterologous polypeptides from filamentous fungi. Such vectors are used in novel processes to express and secrete such heterologous polypeptides. The vectors used for transforming a filamentous fungus to express and secrete a heterologous polypeptide include a DNA sequence encoding a heterologous polypeptide and a DNA sequence encoding a signal sequence which is functional in a secretory system in a given filamentous fungus and which is operably linked to the sequence encoding the heterologous polypeptide. Such signal sequences may be the signal sequence normally associated with the heterologous polypeptides or may be derived from other sources. The vector may also contain DNA sequences encoding a promoter sequence which is functionally recognized by the filamentous fungus and which is operably linked to the DNA sequence encoding the signal sequence. Preferably functional polyadenylation sequences are operably linked to the 3' terminus of the DNA sequence encoding the heterologous polypeptides. Each of the above described vectors are used in novel processes to transform a filamentous fungus wherein the DNA sequences encoding the signal sequence and heterologous polypeptide are expressed. The thus synthesized polypeptide is thereafter secreted from the filamentous fungus.

14 Claims, 23 Drawing Sheets

OTHER PUBLICATIONS

Grant, D. M., et al., "Transformation of *Neurospora crassa* with Recombinant Plasmids Containing the Cloned Glutamate Dehydrogenase (am) Gene: Evidence for Autonomous Replication of the Transforming Plasmid," *Molecular and Cellular Biology*, 4(10):2041–2051 (1984).

Buxton, F. P., et al., "The transformation of mycelial spheroplasts of *Neurospora crassa* and the attempted isolation of an autonomous replicator," *Mol. Gen. Genet.*, 196:339–344 (1984).

Kinsey, J. A., et al., "Transformation of *Neurospora crassa* with the Cloned am (Glutamate Dehydrogenase) Gene," *Molecular and Cellular Biology*, 4(1):117–122 (1984).

Bull, J. H., et al., "Heavily methylated amplified DNA in transformants of *Neurospora crassa*," *Nature*, 310:701–704 (1984).

Miller, B. L., et al., "Direct and Indirect Gene Replacements in *Aspergillus nidulans*," *Molecular and Cellular Biology*, 5(7):1714–1721 (1985).

Weiss, R. L., et al., "Expression of Aspergillus Genes in Neurospora," *Gene Manipulation in Fungi*, (1985).

Johnstone, I. L., "Transformation of *Aspergillus nidulans*," *Microbiological Sciences*, 2(10):307–311 (1985).

Johnstone, I. L., et al., "Cloning an *Aspergillus nidulans* developmental gene by transformation," *The EMBO Journal*, 4(5):1307–1311 (1985).

Buxton, F. P., et al., "Transformation of *Aspergillus niger* using the argB gene of *Aspergillus nidulans*," *Gene*, 37:207–214 (1985).

Turner, G., et al., "Cloning and Transformation in Aspergillus," *Gene Manipulations in Fungi* (1985).

Ballance, D. J., et al., "Development of a high–frequency transforming vector for *Aspergillus nidulans*," *Gene*, 36:321–331 (1985).

Yelton, M. M., et al., "A cosmid for selecting genes by complementation in *Aspergillus nidulans*: Section of the developmentally regulared yA locus," *Proc. Natl. Acad. Sci. USA*, 82:834–838 (1985).

Kelly, J. M., et al., "Transformation of *Aspergillus niger* by the amdS gene of *Aspergillus nidulans*," *The EMBO Journal*, 4(2):475–479 (1985).

Akins, R. A., et al., "General Method for Cloning *Neurospora crassa* Nuclear Genes by Complementation of Mutants," *Molecular and Cellular Biology*, 5(9):2272–2278 (1985).

Paietta, J., et al., "Plasmid recovery from transformants and the isolation of chromosomal DNA segments improving plasmid replication in *Neurospora crassa*," *Current Genetics*, 9:383–388 (1985).

Kuiper, M.T. R., et al., "A recombinant plasmid carrying the mitochondrial plasmid sequence of *Neurospora intermedia* LaBelle yields new plasmid derivatives in *Neurospora crassa* transformants," *Current Genetics*, 9:471–477 (1985).

Dhawale, S. S., et al., "Transformation of *Neurospora crassa* with circular and linear DNA and analysis of the fate of the transforming DNA," *Current Genetics*, 10:205–212 (1985).

Wernars, K., et al., "Gene amplification in *Aspergillus nidulans* by transformation with vectors containing the amdS gene," *Current Genetics*, 9:361–368 (1985).

Saunders, G., et al., "Fungal cloning vectors," *Trends in Biotechnology*, 4:93–98 (1986).

Hynes, M. J., "Topical Review—Transformation of Filamentous Fungi," *Experimental Mycology*, 10:1–8 (1986).

Durrens, P., et al., "Heterologous insertion of transforming DNA and generation of new deletions associated with transformation in *Aspergillus nidulans*," *Mol. Gen. Genet.*, 203:544–549 (1986).

Barnes, D. E., et al., "Behavior of recombinant plasmids in *Aspergillus nidulans*: structure and stability," *Current Genetics*, 10:767–775 (1986).

Upshall, A., "Genetic and molecular characterization of argB+ transformants of *Aspergillus nidulans*," *Current Genetics*, 10:593–599 (1986).

Viebrock, A., et al., "The imported preprotein of the proteolipid subunit of the mitochondrial ATP synthase from *Neurospora crassa*. Molecular cloning and sequencing of the mRNA," *The EMBO Journal*, 1(5):565–571 (1982).

Alton, N. K., et al., "5'–Untranslated sequences of two structural genes in the qa gene cluster of *Neurospora crassa*," *Proc. Natl. Acad. Sci. USA*, 79:1655–1959 (1982).

Keesey, J. K., Jr., et al., "Cloning of the trp–1 Gene from *Neurospora crassa* by Complementation of a trpC Mutation in *Escherichia coli*," *Journal of Bacteriology*, 152(2):954–958 (1982).

Shoemaker, S., et al, "Molecular Cloning of Exo–Cellobiohydrolase I Derived From *Trichoderma Reesei* Strain L27," *Biotechnology*, 1:691–697 (1983).

Kinnaird, J. H., et al., "The complete nucleotide sequence of the *Neurospora crassa am* (NADP–specific glutamate dehydrogenase) gene," *Gene*, 26:253–260 (1983).

Berse, B., et al., "Cloning and characterization of the ornithine carbamoyltransferase gene from *Aspergillus nidulans*," *Gene*, 25:109–117 (1983).

Buxton, F. P., et al., "Cloning of the Structural Gene for Orotidine 5'–Phosphate Carboxylase of *Neurospora crassa* by Expression in *Escherichia coli*," *Mol. Gen. Genet*, 190:403–405 (1983).

Harris et al., *Nucleic Acids Res.*, 10(7):2177–2187 (Apr. 1982).

Woudt, L. P., et al., *Nucleic Acids Research*, 11:5353–6346 (1983).

Hynes, M. J., et al., "Isolation of Genomic Clones Containing the amdS Gene of *Aspergillus nidulans* and Their use in the Analysis of Structural and Regulatory Mutations," *Molecular and Cellular Biology*, 3(8):1430–1439 (1983).

Arends, H., et al., "Nucleotide sequence of the cloned mRNA and gene of the ADP/ATP carrier from *Neurospora crassa*," *The EMBO Journal*, 3(2):377–382 (1984).

Nunberg, J. H., et al., "Molecular Cloning and Characterization of the Glucoamylase Gene of *Aspergillus awamori*," *Molecular and Cellular Biology*, 4(11):2306–2315 (1984).

Boel, E., et al., "Two different types of intervening sequences in the glucoamylase gene from *Aspergillus niger*," *EMBO Journal*, 3:1581–1585 (1984).

Sebald, W., et al., "H+–ATPase (ATP Synthase):Structure, function, Boogenesis The $F_0$ $F_1$ Complex of Coupling Membranes," *Abteilung für Biotechnologische Forschung mbH.*, W. Germany, pp. 67–75 (1984).

Rutledge, B. J., "Molecular characterization of the qa–4 gene of *Neurospora crassa*," *Gene*, 32:275–287 (1984).

Doy, C. H., et al., "Genomic Clones of *Aspergillus nidulans* Containing alcA, the Structural Gene for Alcohol Dehydrogenase and alcR, a Regulatory Gene for Ethanol Metabolism," *DNA*, 4(2):105–114 (1985).

Legerton, T.L.K., et al., Cloning and characterization of the multifunctional his–3 gene of *Neurospora crassa*, *Gene*, 39:129–140 (1985).

Kos, A., et al., "Isolation and characterization of the *Aspergillus niger* trpC gene," *Gene*, 39:231–238 (1985).

Münger, K., et al., "Isolation and structural organization of the *Neurospora crassa* copper metallothionein gene," *The EMBO Journal*, 4(10):2665–2668 (1985).

Mullaney, E. J., et al., "Primary structure of the trpC gene from *Aspergillus nidulans*," *Mol. Gen. Genet.*, 199:37–45 (1985).

McKnight, G. L., et al., Nucleotide Sequence of the Triosephosphate Isomerase Gene from *Aspergillus nidulans*: Implications for a Differential Loss of Introns, *Cell*, 46:143–147 (1986).

Ballance, D. J., et al., "Gene cloning in *Aspergillus nidulans*: isolation of the isocitrate lyase gene (acuD)," *Mol. Gen. Genet.*, 202:271–275 (1986).

Orbach, M. J., et al., "Cloning and Characterization of the Gene for β–Tubulin from a Benomyl–Resistant Mutant of *Neurospora crassa* and Its Use as a Dominant Selectable Marker," *Molecular and Cellular Biology*, 6:2452–2461 (1986).

Caddick, M. X., et al., "Cloning of the regulatory gene areA mediating nitrogen metabolite repression in *Aspergillus nidulans*," *The EMBO Journal*, 5(5):1087–1090 (1986).

Vollmer, S. J., et al., "Efficient cloning of genes of *Neurospora crassa*," *Proc. Natl. Acad. Sci. USA*, 83:4869–4873 (1986).

Newbury, S. F., et al., "Sequence analysis of the pyr–4 (orotidine 5'–P decarboxylase) gene of *Neurospora crassa*," *Gene*, 43:51–58 (1986).

Huiet, L., et al., "The qa repressor gene of *Neurospora crassa*: Wild–type and mutant nucleotide sequences," *Proc. Natl. Acad. Sci. USA*, 83:3381–3385 (1986).

Clements, J. M., et al., "Transcription and processing signals in the 3–phosphoglycerate kinase (PGK) gene from *Aspergillus nidulans*," *Gene*, 44:97–105 (1986).

Upshall, A., "Filamentous Fungi in Biotechnology," *BioTechniques*, 4:158–166 (1986).

Penttilä, M. E., et al., "Cloning of *Aspergillus niger* genes in yeast. Expression of the gene coding Aspergillus β–glucosidase," *Mol. Gen. Genet.*, 194:494–499 (1984).

McKnight, G. L., "Lack of an Aspergillus Promoter Function and Intron Splicing in Saccharomyces," *J. Cell. Biochem. Suppl.*, 9c:137 (1985).

Innis, M.A., et al., Expression, Glycosylation, and Secretion of an Aspergillus Glucoamylase by *Saccharomyces cerevisiae*, *Science*, 228:21–26 (1985).

Briggs, M. S., et al., "Molecular Mechanisms of Protein Secretion: The Role of the Signal Sequence," *Advances in Protein Chemistry*, 38:109–180 (1986).

Nishimori, K., et al., "Expression of cloned calf prochymosin gene sequence in *Escherichia coli*," *Gene*, 19:337–344 (1982).

Beppu, T., "The cloning and expression of chymosin (rennin) genes in microorganisms," *Trends in Biotech.*, 1:85–89 (1983).

Emtage, J. S., et al., "Synthesis of calf prochymosin (prorennin) in *Escherichia coli*," *Proc. Natl. Acad. Sci. USA*, 80:3671–3675 (1983).

Martson, F. A. O., et al., "Purification of Calf Prochymosin (Prorennin) Synthesized in *Escherichia Coli*," *Biotechnology* 2:800–804 (1984).

Kawaguchi, Y., et al., Renaturation and activation of calf prochymosin produced in an insoluble form in *Escherichia coli*, *Journal of Biotechnology*, 1:307–315 (1984).

Nishimori, K., et al., "Expression of cloned calf prochymosin cDNA under control of the tryptophan promoter," *Gene*, 29:41–419 (1984).

McCaman, M. T., et al., Enzymatic properties and processing of bovine prochymosin synthesized in *Escherichia coli*, *Journal of biotechnology*, 2:177–190 (1985).

McGuire, J., "Cloning, Expression, Purification and Testing of Chymosin," from *Proceedings of Bio Expo 86. The American Commerical and Industrial Conference and Exposition in Biotechnology*, pp. 121–141 (1986).

Mellor, J., et al., Efficient synthesis of enzymatically active calf chymosin in *Saccharomyces cerevisiae*, *Gene*, 24:1–14 (1983).

Goff, C. G., et al., Expression of calf prochymosin in *Saccharomyces cerevisiae*, *Gene*, 27:35–46 (1984).

Smith, R. A., et al., "Heterologous Protein Secretion from Yeast," *Science*, 229:1219–1224 (1985).

Moir, D. T., et al., Production of Calf Chymosin by the Yeast *S. cerevisiae*, *Developments in Industrial Microbiology*, 26:75–85 (1985).

Tudzynski, U., et al., "Transformation to Senescence with Plasmid Like DNA in the Ascomycete *Podospora anserina*," *Current Genetics* 2:181–184 (1980).

Freer, S. N., "Fungal Nucleic Acids," In: *Agricultural Research Service, USDA*, Peoria, Illinois, pp. 175–193 (1983).

Stahl, U., et al., "Replication and expression of a bacterial–mitochondrial hybrid plasmid in the fungus *Podospora anserina*," *Proc. Natl. Acad. Sci. USA*, 79:3641–3645 (1982).

Bech, A. M., et al., "Partial primary structure of *Mucor miehei* protease," *Neth. Milk Dairy J.*, 35:275–280 (1981).

Moir, D., et al., "Molecular cloning and characterization of double–stranded cDNA coding for bovine chymosin," *Chemical Abstracts*, vol. 98, No. 15, p. 173, Abstract No. 120575m (1983).

Hayenga, K., et al., "Expression of Bovine Calf Chymosin by *Aspergillus nidulans*," *Journal of Cellular Biochemistry Supp.* vol. 0, No. 10, Part A, Abstract E109 (1986).

Cullen, D., et al., "Expression of bovine chymosin by *Aspergillus nidulans*," *Heredity*, vol. 57, p. 131, Abstract No. 20 (1986).

Case, M. E., et al., "Efficient transformation of *Neurospora crassa* by utilizing hybrid plasmid DNA," *Proc. Natl. Acad. Sci. USA* 76:5259–5263 (1979).

Nishimori, K., et al., "Cloning in *Escherichia coli* of the Structural Gene of Prorennin, the Precursor of Calf Milk–Clotting Enzyme Rennin," *J. Biochem.*, 90:901–904 (1981).

Moir, D. T., et al., "Molecular Cloning and Characterization of double–stranded cDNA coding for bovine chymosin," *Gene*, 19:127–138 (1982).

Nishimori, K. et al., Nucleotide Sequence of Calf Prorennin cDNA Cloned in *Escherichia coli*, *J. Biochem.*, 91:1085–1088 (1982).

Hidaka, M., et al., "Cloning and structural analysis of the calf prochymosin gene," *Gene*, 43:197–203 (1986).

Heyneker, H. L., et al., "Cloning strategies in Aspergillus for enzyme production: prochymosin as a model system," *Proc. of Bio Expo 86*, 86:145–149 (1986).

Berka et al. *Biotech ADV.* 7:127–154 (1989).

Hahm et al., *Agric. Biol. Chem.* 54:2513–2520 (1990).

* cited by examiner

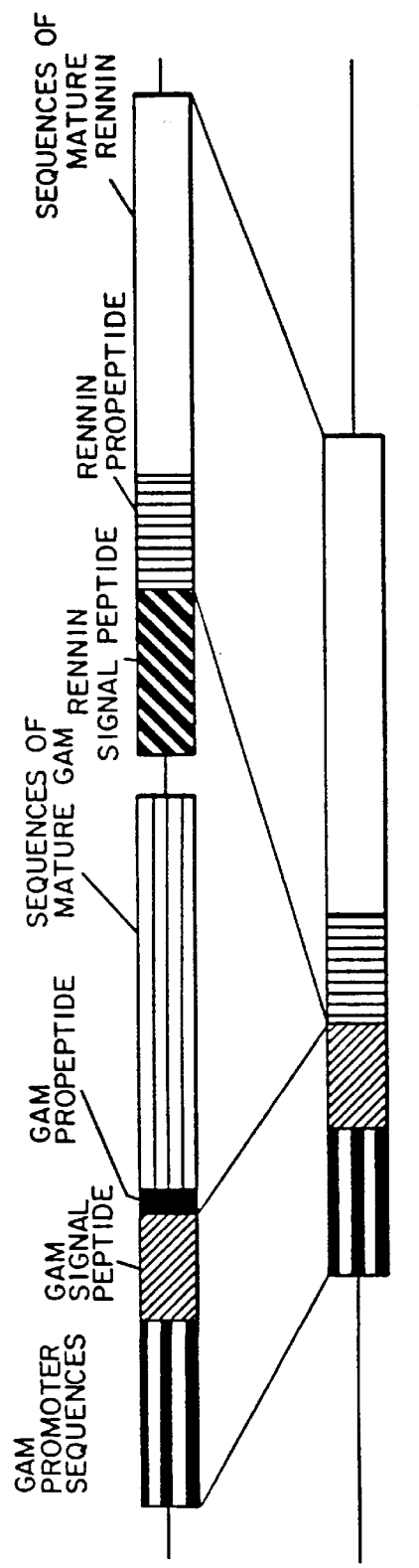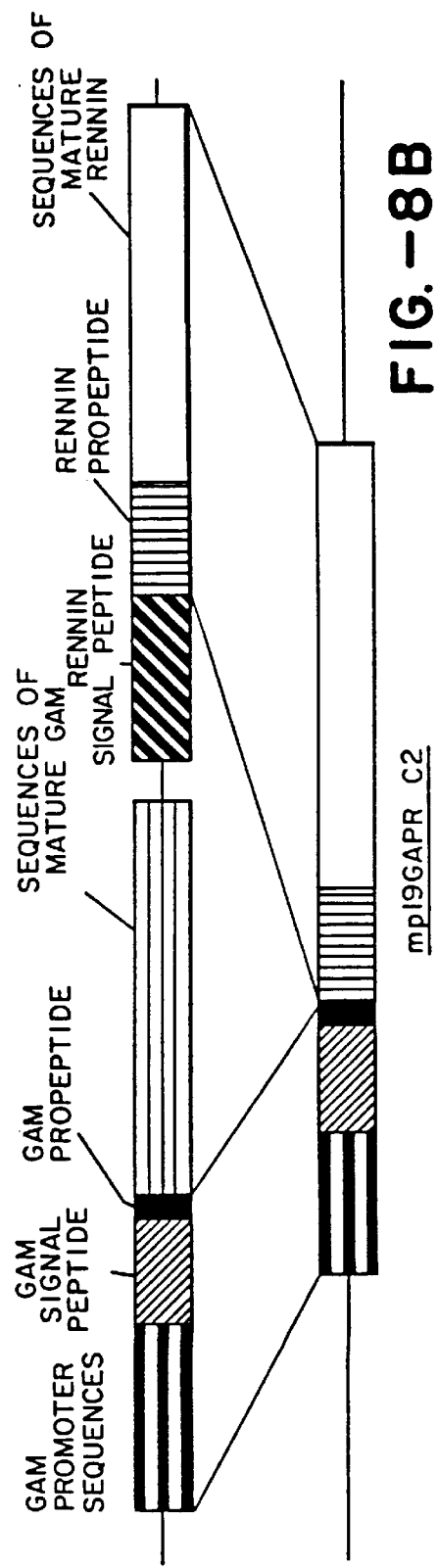
FIG.-8A
FIG.-8B

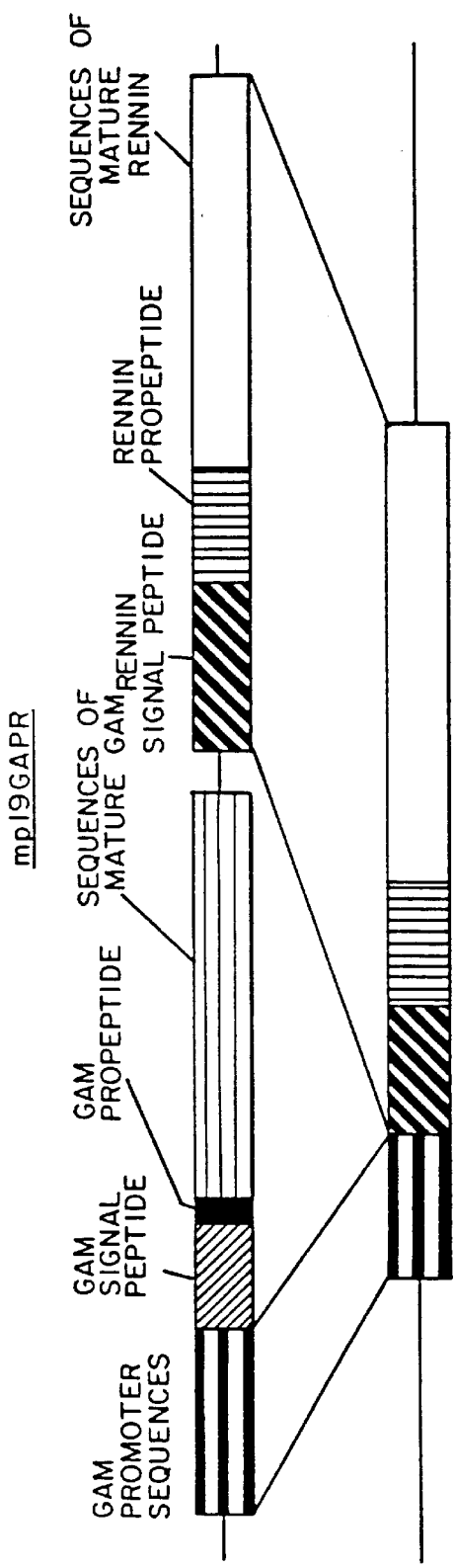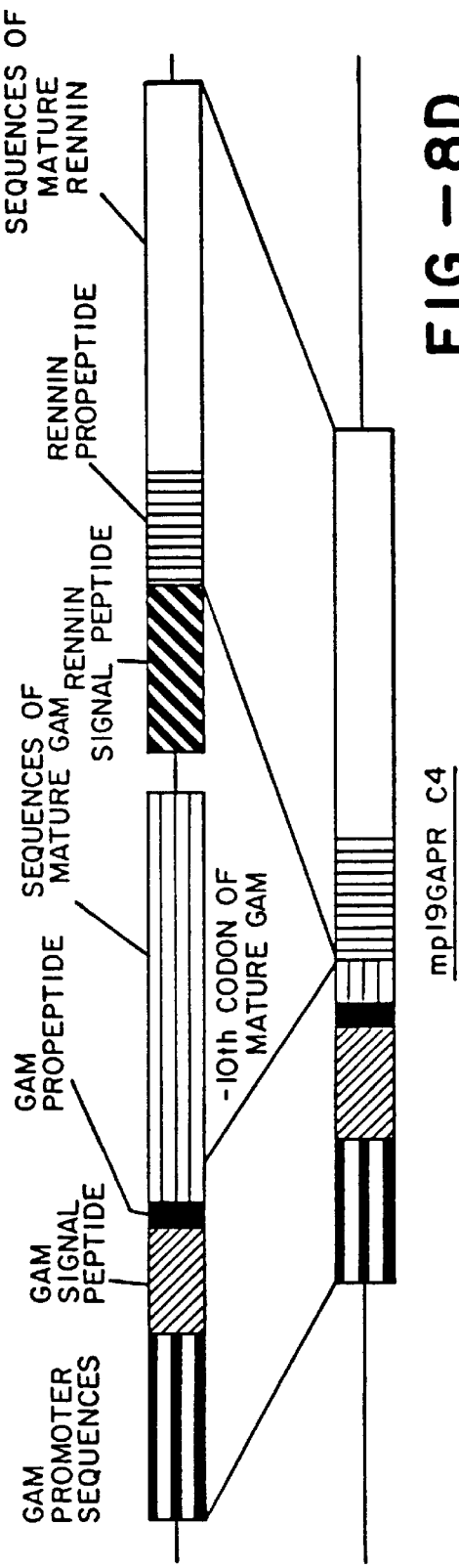

length: 1988

```
  1  AAGCTTCCAT TTCAGAAAAG AAAGCTCTCG GAGTTGTCAT TGAGGCATTT TTACAGCCTT

61  TTTCCGCTCT CACTCTGTAT TTCTATGAGA AAGAGAAAGA TAGGAATGTC ATGCATAAGA

121  TGCTACAAGA TCATGCCAAC GGTAGTACAC ACAATTCCTG CCTTTTATGA CCTTTTTATG

181  CTAAGTCTTT TTGGAAATTT ATCCCGCGGT CCTAGGTTGT ACCCAGTCGT TGCATCCACC

241  TTTCCTGGTA AAAACATACA ATTATGGACT AAATGGTTTC TTAAATGTCA ACACTCTAGA

301  CGGAAGGGCA CAAAGATCTT TAGTGCCTGG GCCAACTGTA GGTAGATCTT TTTTTCATAT

361  AAAACCAGAC GAGTGTGAAG GTTGCGAGAC TCCATCAGAT TCGACC ATG CTC TTC
                                                      Met Leu Phe

417  TCT CAG ATT ACT TCT GCG ATC CTT TTA ACA GCG GCT TCC TTG TCG CTT
             -61                                                -51
     Ser Gln Ile Thr Ser Ala Ile Leu Leu Thr Ala Ala Ser Leu Ser Leu

465  ACC ACT GCT CGC CCG GTA TCC AAG CAA TCC GAG TCC AAG GAC AAG CTT
                             -41
     Thr Thr Ala Arg Pro Val Ser Lys Gln Ser Glu Ser Lys Asp Lys Leu

513  CTG GCG CTT CCT CTC ACC TCG GTG TCC CGC AAG TTC TCT CAA ACC AAG
                 -31                                    -21
     Leu Ala Leu Pro Leu Thr Ser Val Ser Arg Lys Phe Ser Gln Thr Lys

561  TTC GGT CAG CAA CAA CTT GCT GAG AAG CTA GCA GGT CTC AAG CCC TTC
                                     -11
     Phe Gly Gln Gln Gln Leu Ala Glu Lys Leu Ala Gly Leu Lys Pro Phe

609  TCT GAA GCT GCC GCA GAC GGC TCC GTC GAT ACG CCC GGC TAT TAC GAC
             -1  1                                       11
     Ser Glu Ala Ala Ala Asp Gly Ser Val Asp Thr Pro Gly Tyr Tyr Asp

657  TTT GAT CTG GAG GAG TAT GCT ATT CCG GTC TCC ATT GGT ACT CCT GGT
                                 21
     Phe Asp Leu Glu Glu Tyr Ala Ile Pro Val Ser Ile Gly Thr Pro Gly
```

FIG.—11A

705 CAA GAC TTT TTG CTC TTG TTC GAC ACT GGC AGC TCC GAT ACT TGG GTT
    31                                          41
    Gln Asp Phe Leu Leu Leu Phe Asp Thr Gly Ser Ser Asp Thr Trp Val

753 CCA CAC AAG GGT TGC ACC AAG TCT GAA GGT TGT GTT GGC AGC CGA TTC
              51                                              61
    Pro His Lys Gly Cys Thr Lys Ser Glu Gly Cys Val Gly Ser Arg Phe

801 TTT GAT CCA TCG GCT TCC TCC ACT TTT AAA GCA ACT AAC TAC AAC CTA
                            71
    Phe Asp Pro Ser Ala Ser Ser Thr Phe Lys Ala Thr Asn Tyr Asn Leu

849 AAC ATC ACC TAC GGT ACT GGC GGC GCA AAC GGT CTT TAC TTT GAA GAC
              81                                              91
    Asn Ile Thr Tyr Gly Thr Gly Gly Ala Asn Gly Leu Tyr Phe Glu Asp

897 AGC ATC GCT ATC GGC GAC ATC ACC GTG ACC AAG CAA ATT CTG GCT TAC
                                101
    Ser Ile Ala Ile Gly Asp Ile Thr Val Thr Lys Gln Ile Leu Ala Tyr

945 GTC GAT AAT GTT CGC GGC CCA ACT GCT GAG CAG TCT CCT AAC GCT GAC
    111                                         121
    Val Asp Asn Val Arg Gly Pro Thr Ala Glu Gln Ser Pro Asn Ala Asp

993 ATT TTC CTT GAT GGT CTC TTT GGT GCA GCC TAC CCA GAC AAC ACG GCC
              131                                             141
    Ile Phe Leu Asp Gly Leu Phe Gly Ala Ala Tyr Pro Asp Asn Thr Ala

1041 ATG GAA GCA GAG TAT GGA TCG ACT TAT AAC ACT GTT CAC GTC AAC CTC
                                  151
     Met Glu Ala Glu Tyr Gly Ser Thr Tyr Asn Thr Val His Val Asn Leu

1089 TAC AAG CAA GGC TTG ATC TCT TCT CCT CTT TTC TCG GTC TAC ATG AAC
               161                                             171
     Tyr Lys Gln Gly Leu Ile Ser Ser Pro Leu Phe Ser Val Tyr Met Asn

1137 ACT AAC AGC GGC ACT GGA GAG GTC GTC TTT GGT GGA GTC AAC AAC ACG
                                   181
     Thr Asn Ser Gly Thr Gly Glu Val Val Phe Gly Gly Val Asn Asn Thr

1185 CTT CTC GGC GGC GAC ATT GCC TAC ACG GAC GTT ATG AGT CGT TAT GGT
     191                                         201
     Leu Leu Gly Gly Asp Ile Ala Tyr Thr Asp Val Met Ser Arg Tyr Gly

1233 GGT TAT TAC TTC TGG GAC GCA CCC GTC ACA GGT ATC ACC GTC GAT GGA
               211                                             221
     Gly Tyr Tyr Phe Trp Asp Ala Pro Val Thr Gly Ile Thr Val Asp Gly

FIG.—11B

1281 TCT GCT GCT GTC AGG TTC TCG AGA CCC CAA GCA TTC ACC ATC GAT ACT
                                    231
     Ser Ala Ala Val Arg Phe Ser Arg Pro Gln Ala Phe Thr Ile Asp Thr

1329 GGC ACC AAC TTT TTC ATT ATG CCC TCA AGC GCC GCT TCT AAG ATT GTC
                241                                     251
     Gly Thr Asn Phe Phe Ile Met Pro Ser Ser Ala Ala Ser Lys Ile Val

1377 AAA GCA GCT CTC CCT GAT GCC ACT GAA ACC CAG CAG GGC TGG GTT GTT
                                    261
     Lys Ala Ala Leu Pro Asp Ala Thr Glu Thr Gln Gln Gly Trp Val Val

1425 CCT TGC GCT AGC TAC CAG AAC TCC AAG TCG ACT ATC AGC ATC GTC ATG
     271                                             281
     Pro Cys Ala Ser Tyr Gln Asn Ser Lys Ser Thr Ile Ser Ile Val Met

1473 CAA AAG TCC GGC TCA AGC AGT GAC ACT ATT GAG ATC TCG GTT CCT GTC
                    291                                         301
     Gln Lys Ser Gly Ser Ser Ser Asp Thr Ile Glu Ile Ser Val Pro Val

1521 AGC AAA ATG CTT CTT CCA GTC GAC CAA TCG AAC GAG ACT TGC ATG TTT
                                    311
     Ser Lys Met Leu Leu Pro Val Asp Gln Ser Asn Glu Thr Cys Met Phe

1569 ATC ATT CTT CCC GAC GGT GGT AAC CAG TAC ATT GTT GGC AAC TTG TTC
                321                                         331
     Ile Ile Leu Pro Asp Gly Gly Asn Gln Tyr Ile Val Gly Asn Leu Phe

1617 CTG CGC TTC TTT GTC AAT GTT TAC GAC TTT GGC AAC AAC CGT ATC GGC
                                    341
     Leu Arg Phe Phe Val Asn Val Tyr Asp Phe Gly Asn Asn Arg Ile Gly

1665 TTT GCA CCT TTG GCC TCG GCT TAT GAA AAC GAG TAA      AGGGGCACCA A
     351                                     361
     Phe Ala Pro Leu Ala Ser Ala Tyr Glu Asn Glu OC*

1712 TTCTTCTTT AGCTGCTCAG ATAACTTTGT AACTCTCTGA TATACTCTTT ATAACCTTTA T

1772 TTCTCACTT TTTAACTGTA TTCCAATACA TTATTTGAAC TTACTAAATA TTACGCTTAT T

1832 CTTGTTTGG GTGAGTTGTA GAGTAAAAAA AATGCTTAGA AGCGGAATTG TATTTTGCAA G

1892 GAATGTACA

FIG.—11C

```
                                                              aluI
                                                              ahaIII
801   CTAAATTAAA  TATTTATAAT  AACTTCTATT  TTTATATAAT  TTAATCCTAA  TTAAGAAATA  ATTTTTAAAG  CTCCTTATATT
      GATTTAATTT  ATAAATATTA  TTGAAGTATT  AAATATATTA  AATTAGGATT  AATTCTTTAT  TAAAAATTTC  GACAATATAA
                                          rsaI                              ******
                                          scaI
881   AAACTAGACT  ACTAGAAAAA  TATTATAAAT  ATAGAATAAT  AATAAAGTAC  TATATTTTTA  TATTTATTAT  TTAAGAACTC
      TTTGATCTGA  TGATCTTTTT  ATAATATTTA  TATCTTATTA  TTATTTCATG  ATATAAAAAT  ATAATAATAA  AATTCTTGAG
                                                                 ****                     aluI
961   TCCCTGCAAA  ATATAATTAT  AAAATTTATA  TTAGTAATTA  TTAATAGCTT  AAAGTTTAG  AAATTAGAGC
      AGGGACGTTT  TATATTAATA  TTTTAAATAT  AATCATTAAT  AATTATCGAA  TTTCAAATC  TTTAATCTCG
      ahaIII
1041  TTATAAGTTT  AAAAAATTTT  ATTATTATTA  TAAATTTACTA  TACTTTACTA  TAATTAGATA  TTTTAATAAA
      AATATTCAAA  TTTTTTAAAA  TAATAATAAT  ATTTAAATGAT  ATGAAAATGAT  ATTAATCTAT  AAAATTATTT
                             ahaIII                                           aluI
                                                                              bamHI
                                                                    aluI      bbvI
1121  TAGTAAATAT  ATTAGACAGA  TATACTTAAT  TATTTTAATT  TATTTTAAAA  TATTAACTAG  GTAAGCTAGC  AGCTTTGCCT
      ATCATTTATA  TAATCTGTCT  ATATGAATTA  ATAAAATTAA  ATAAAATTTT  ATAATTGATC  CATTCGATCG  TCGAAACGGA
```

```
      aluI
      pvuII                                                        ddeI
  1   CAGCTGACTT GATAATTACA TTACTATAAA AAACTCTTAC TAAGTTACTA GATAAGAACT TTATTTATAT TAGTTACTTA
      GTCGACTGAA CTATTAATGT AATGATATTT TTTGAGAATG ATTCAATGAT CTATTCTTGA AATAAATATA ATCAATGAAT
      rsaI
      scaI
 81   TTTTATAGTAA CTTTAGTACT ACTTATAAAA AAGCTAGATA GAGATTATA GTTCTATACT AATTACTATG CCTTAAATAT
      AAATATCATT GAAATCATGA TGAATATTTT TTCGATCTAT CTCTAATAT CAAGATATGA TTAATGATAC GGAATTTATA
                                                      xbaI
161   TATTATTAAA AAAGATTATT ATCCCCTTTC TCTAATTAAT AAAACTCTAG AATTTATCTC TAAAATTAAA AATTACTATA
      ATAATAATTT TTTCTAATAA TAGGGGAAAG AGATTAATTA TTTTGAGATC TTAAATAGAG ATTTTAATTT TTAATGATAT
                                                                                    xbaII
                                                                                    xbaI     aluI
241   AACCTAATAT TATTACTATC TTTTATAAAA TCTAGATTTA TTTTAAAGAT AAATAGAAGA TAGCTTTCAG GATATATTTT
      TTGGATTATA ATAATGATAG AAAATATTTT AGATCTAAAT AAAATTTCTA TTTATCTTCT ATCGAAAGTC CTATATAAAA
                                                                                            sau3AI
                                                                                            dpnI
                                                                                            xbuII
                                                                                            bglII
321   AGGTTATATA AATAGTTAAT TACTTTTTTT AAGCTAGTAA ATATTCTAAG TATATTATAA TATTATATTA ACTAGATCTT
      TCCAATATAT TTATCAATTA ATGAAAAAAA TTCGATCATT ATATAAGATTC ATATAAT AT AATAATATAAT TGATCTAGAA
           xbaI                                   aluI                                   aluI
401   ACATAACTTT CTAGATAAAT TTGCCTTTAT ATACTTAGAT AATATATTAA TTTTTACTAA AAAAATGATT TAGCTTATTA AAAAAGTATT
      TGTATTGAAA GATCTATTTA AACGGAAATA TATGAATCTA TTATATAATT AAAAATGATT TTTTTACTAA ATCGAATAAT TTTTTCATAA
                                         xbaI                                                   ahaIII
481   ATAATTATAT ATTAATTAAT TTCTAGAAAT TTCTAGAAAC CTTAATATTA AGGACTATAG CTTAATATTA ATAAATAATA TTTTAAAATT
      TATTAATATA TAATTAATTA AAGATCTTTG AAGATCTTTG GAATTATAAT TCCTGATATC GAATTATAAT TATTTATTAT AAAATTTTAA
                                                                        sau3AI
                                                                        dpnI
      ddeI                                                              xbaII   ddeI        aluI
561   AACTAAGTCT TTAAGATTTA TTATTAATAT AAAGAAGGGT ATATAAATAG ATCCTAAGAA AATAAGCTAT CCTTAAATAA
      TTGATTCAGA AATTCTAAAT AATAATTATA TTTCTTCCCA TATATTTATC TAGGATTCTT TTATTCGATA GGAATTTATT
                                                                                            ddeI
641   TAAATCCTTA TATTAGTTAA CTTCTTTTTA AAAAAATATA AGATTTATAA ATTTTTATTA AAAAAGTATT AACTTCTTAG
      ATTTAGGAAT ATAATCAATT GAAGAAAAAT TTTTTTATAT TCTAAATATT TAAAAATAAT TTGAAGAATC TTGAAGAATC
                                                                                            ahaIII aluI
721   ACCTGATATA CCTACTTACT ATTCTAATAT AAAATTTTTA TAAATTTTTA TAGATTAAGAA TAGATTAAGAA GTTAAATAG
      TGGACTATAT GGATGAATGA TAAGATTATA TTTTAAAAAT ATTTAAAATT ATCTAATTCT TCATATGGAT CAAATTTATC
```

RESTRICTION MAP OF THE 3.7 KB INSERT OF pRSH I

SEQUENCE LISTING

<160> NUMBER OF SEQ ID NOS: 28

<210> SEQ ID NO 1
<211> LENGTH: 24
<212> TYPE: DNA
<213> ORGANISM: Artificial Sequence
<220> FEATURE:
<223> OTHER INFORMATION: phospharylated synthetic linker sequence

<400> SEQUENCE: 1
gatccatcga tctcgagatc gatg                                              24

<210> SEQ ID NO 2

-continued

```
<211> LENGTH: 1900
<212> TYPE: DNA
<213> ORGANISM: Rhizomucor miehei
<220> FEATURE:
<221> NAME/KEY: CDS
<222> LOCATION: (408)..(1700)
<223> OTHER INFORMATION:

<400> SEQUENCE: 2
aagcttccat ttcagaaaag aaagctctcg gagttgtcat tgaggcattt ttacagcctt      60
tttccgctct cactctgtat ttctatgaga aagagaaaga taggaatgtc atgcataaga    120
tgctacaaga tcatgccaac ggtagtacac acaattcctg cctttatga cctttttatg     180 ctaagtcttt ttggaaattt atcccgcggt cctaggttgt acccagtcgt tgcatccacc    240
tttcctggta aaacataca attatggact aaatggtttc ttaaatgtca acactctaga     300
cggaagggca caaagatctt tagtgcctgg gccaactgta ggtagatctt tttttcatat    360
aaaaccagac gagtgtgaag gttgcagac tccatcagat tccgacc atg ctc ttc      416
                                                  Met Leu Phe
                                                   1 tct cag att act tct gcg atc ctt tta aca gcg gct tcc ttg tcg ctt      464
Ser Gln Ile Thr Ser Ala Ile Leu Leu Thr Ala Ala Ser Leu Ser Leu
  5                  10                  15 acc act gct cgc ccg gta tcc aag caa tcc gag tcc aag gac aag ctt      512
Thr Thr Ala Arg Pro Val Ser Lys Gln Ser Glu Ser Lys Asp Lys Leu
 20                  25                  30                  35 ctg gcg ctt cct ctc acc tcg gtg tcc cgc aag ttc tct caa acc aag      560
Leu Ala Leu Pro Leu Thr Ser Val Ser Arg Lys Phe Ser Gln Thr Lys
                 40                  45                  50 ttc ggt cag caa caa ctt gct gag aag cta gca ggt ctc aag ccc ttc      608
Phe Gly Gln Gln Gln Leu Ala Glu Lys Leu Ala Gly Leu Lys Pro Phe
             55                  60                  65 tct gaa gct gcc gca gac ggc tcc gtc gat acg ccc ggc tat tac gac      656
Ser Glu Ala Ala Ala Asp Gly Ser Val Asp Thr Pro Gly Tyr Tyr Asp
         70                  75                  80 ttt gat ctg gag gag tat gct att ccg gtc tcc att ggt act cct ggt      704
Phe Asp Leu Glu Glu Tyr Ala Ile Pro Val Ser Ile Gly Thr Pro Gly
     85                  90                  95 caa gac ttt ttg ctc ttg ttc gac act ggc agc tcc gat act tgg gtt      752
Gln Asp Phe Leu Leu Leu Phe Asp Thr Gly Ser Ser Asp Thr Trp Val
100                 105                 110                 115 cca cac aag ggt tgc acc aag tct gaa ggt tgt gtt ggc agc cga ttc      800
Pro His Lys Gly Cys Thr Lys Ser Glu Gly Cys Val Gly Ser Arg Phe
                120                 125                 130 ttt gat cca tcg gct tcc tcc act ttt aaa gca act aac tac aac cta      848
Phe Asp Pro Ser Ala Ser Ser Thr Phe Lys Ala Thr Asn Tyr Asn Leu
            135                 140                 145 aac atc acc tac ggt act ggc ggc gca aac ggt ctt tac ttt gaa gac      896
Asn Ile Thr Tyr Gly Thr Gly Gly Ala Asn Gly Leu Tyr Phe Glu Asp
        150                 155                 160 agc atc gct atc ggc gac atc acc gtg acc aag caa att ctg gct tac      944
Ser Ile Ala Ile Gly Asp Ile Thr Val Thr Lys Gln Ile Leu Ala Tyr
    165                 170                 175 gtc gat aat gtt cgc ggc cca act gct gag cag tct cct aac gct gac      992
Val Asp Asn Val Arg Gly Pro Thr Ala Glu Gln Ser Pro Asn Ala Asp
180                 185                 190                 195 att ttc ctt gat ggt ctc ttt ggt gca gcc tac cca gac aac acg gcc     1040
Ile Phe Leu Asp Gly Leu Phe Gly Ala Ala Tyr Pro Asp Asn Thr Ala
                200                 205                 210 atg gaa gca gag tat gga tcg act tat aac act gtt cac gtc aac ctc     1088
```

-continued

```
Met Glu Ala Glu Tyr Gly Ser Thr Tyr Asn Thr Val His Val Asn Leu
            215                 220                 225 tac aag caa ggc ttg atc tct tct cct ctt ttc tcg gtc tac atg aac    1136
Tyr Lys Gln Gly Leu Ile Ser Ser Pro Leu Phe Ser Val Tyr Met Asn
        230                 235                 240 act aac agc ggc act gga gag gtc gtc ttt ggt gga gtc aac aac acg    1184
Thr Asn Ser Gly Thr Gly Glu Val Val Phe Gly Gly Val Asn Asn Thr
    245                 250                 255 ctt ctc ggc ggc gac att gcc tac acg gac gtt atg agt cgt tat ggt    1232
Leu Leu Gly Gly Asp Ile Ala Tyr Thr Asp Val Met Ser Arg Tyr Gly
260                 265                 270                 275 ggt tat tac ttc tgg gac gca ccc gtc aca ggt atc acc gtc gat gga    1280
Gly Tyr Tyr Phe Trp Asp Ala Pro Val Thr Gly Ile Thr Val Asp Gly
                280                 285                 290 tct gct gct gtc agg ttc tcg aga ccc caa gca ttc acc atc gat act    1328
Ser Ala Ala Val Arg Phe Ser Arg Pro Gln Ala Phe Thr Ile Asp Thr
            295                 300                 305 ggc acc aac ttt ttc att atg ccc tca agc gcc gct tct aag att gtc    1376
Gly Thr Asn Phe Phe Ile Met Pro Ser Ser Ala Ala Ser Lys Ile Val
        310                 315                 320 aaa gca gct ctc cct gat gcc act gaa acc cag cag ggc tgg gtt gtt    1424
Lys Ala Ala Leu Pro Asp Ala Thr Glu Thr Gln Gln Gly Trp Val Val
    325                 330                 335 cct tgc gct agc tac cag aac tcc aag tcg act atc agc atc gtc atg    1472
Pro Cys Ala Ser Tyr Gln Asn Ser Lys Ser Thr Ile Ser Ile Val Met
340                 345                 350                 355 caa aag tcc ggc tca agc agt gac act att gag atc tcg gtt cct gtc    1520
Gln Lys Ser Gly Ser Ser Ser Asp Thr Ile Glu Ile Ser Val Pro Val
                360                 365                 370 agc aaa atg ctt ctt cca gtc gac caa tcg aac gag act tgc atg ttt    1568
Ser Lys Met Leu Leu Pro Val Asp Gln Ser Asn Glu Thr Cys Met Phe
            375                 380                 385 atc att ctt ccc gac ggt ggt aac cag tac att gtt ggc aac ttg ttc    1616
Ile Ile Leu Pro Asp Gly Gly Asn Gln Tyr Ile Val Gly Asn Leu Phe
        390                 395                 400 ctg cgc ttc ttt gtc aat gtt tac gac ttt ggc aac aac cgt atc ggc    1664
Leu Arg Phe Phe Val Asn Val Tyr Asp Phe Gly Asn Asn Arg Ile Gly
    405                 410                 415 ttt gca cct ttg gcc tcg gct tat gaa aac gag taa aggggcacca         1710
Phe Ala Pro Leu Ala Ser Ala Tyr Glu Asn Glu
420                 425                 430 attcttcttt agctgctcag ataactttgt aactctctga tatactcttt ataacctta    1770 tttctcactt tttaactgta ttccaataca ttatttgaac ttactaaata ttacgcttat   1830
tcttgtttgg gtgagttgta gagtaaaaaa aatgcttaga agcggaattg tattttgcaa   1890
ggaatgtaca                                                          1900

<210> SEQ ID NO 3
<211> LENGTH: 430
<212> TYPE: PRT
<213> ORGANISM: Rhizomucor miehei

<400> SEQUENCE: 3

Met Leu Phe Ser Gln Ile Thr Ser Ala Ile Leu Leu Thr Ala Ala Ser
1               5                   10                  15

Leu Ser Leu Thr Thr Ala Arg Pro Val Ser Lys Gln Ser Glu Ser Lys
            20                  25                  30

Asp Lys Leu Leu Ala Leu Pro Leu Thr Ser Val Ser Arg Lys Phe Ser
        35                  40                  45
```

-continued

```
Gln Thr Lys Phe Gly Gln Gln Gln Leu Ala Glu Lys Leu Ala Gly Leu
    50                  55                  60

Lys Pro Phe Ser Glu Ala Ala Asp Gly Ser Val Asp Thr Pro Gly
 65                  70                  75                  80

Tyr Tyr Asp Phe Asp Leu Glu Glu Tyr Ala Ile Pro Val Ser Ile Gly
                 85                  90                  95

Thr Pro Gly Gln Asp Phe Leu Leu Phe Asp Thr Gly Ser Ser Asp
            100                 105                 110

Thr Trp Val Pro His Lys Gly Cys Thr Lys Ser Glu Gly Cys Val Gly
            115                 120                 125

Ser Arg Phe Phe Asp Pro Ser Ala Ser Ser Thr Phe Lys Ala Thr Asn
    130                 135                 140

Tyr Asn Leu Asn Ile Thr Tyr Gly Thr Gly Ala Asn Gly Leu Tyr
145                 150                 155                 160

Phe Glu Asp Ser Ile Ala Ile Gly Asp Ile Thr Val Thr Lys Gln Ile
                165                 170                 175

Leu Ala Tyr Val Asp Asn Val Arg Gly Pro Thr Ala Glu Gln Ser Pro
            180                 185                 190

Asn Ala Asp Ile Phe Leu Asp Gly Leu Phe Gly Ala Ala Tyr Pro Asp
    195                 200                 205

Asn Thr Ala Met Glu Ala Glu Tyr Gly Ser Thr Tyr Asn Thr Val His
    210                 215                 220

Val Asn Leu Tyr Lys Gln Gly Leu Ile Ser Ser Pro Leu Phe Ser Val
225                 230                 235                 240

Tyr Met Asn Thr Asn Ser Gly Thr Gly Glu Val Val Phe Gly Gly Val
                245                 250                 255

Asn Asn Thr Leu Leu Gly Gly Asp Ile Ala Tyr Thr Asp Val Met Ser
            260                 265                 270

Arg Tyr Gly Gly Tyr Tyr Phe Trp Asp Ala Pro Val Thr Gly Ile Thr
            275                 280                 285

Val Asp Gly Ser Ala Ala Val Arg Phe Ser Arg Pro Gln Ala Phe Thr
    290                 295                 300

Ile Asp Thr Gly Thr Asn Phe Phe Ile Met Pro Ser Ser Ala Ala Ser
305                 310                 315                 320

Lys Ile Val Lys Ala Ala Leu Pro Asp Ala Thr Glu Thr Gln Gln Gly
                325                 330                 335

Trp Val Val Pro Cys Ala Ser Tyr Gln Asn Ser Lys Ser Thr Ile Ser
            340                 345                 350

Ile Val Met Gln Lys Ser Gly Ser Ser Asp Thr Ile Glu Ile Ser
            355                 360                 365

Val Pro Val Ser Lys Met Leu Leu Pro Val Asp Gln Ser Asn Glu Thr
    370                 375                 380

Cys Met Phe Ile Ile Leu Pro Asp Gly Gly Asn Gln Tyr Ile Val Gly
385                 390                 395                 400

Asn Leu Phe Leu Arg Phe Phe Val Asn Val Tyr Asp Phe Gly Asn Asn
                405                 410                 415

Arg Ile Gly Phe Ala Pro Leu Ala Ser Ala Tyr Glu Asn Glu
            420                 425                 430
```

<210> SEQ ID NO 4
<211> LENGTH: 1864
<212> TYPE: DNA
<213> ORGANISM: Emericella nidulans

```
<400> SEQUENCE: 4
cagctgactt gataattaca ttactataaa aaactcttac taagttacta gataagaact      60
ttatttatat tagttactta tttatagtaa ctttagtact acttataaaa aagctagata     120
gagatttata gttctatact aattactatg ccttaaatat tattattaaa aaagattatt     180
atccccttc tctaattaat aaaactctag aatttatctc taaaattaaa taatttataa     240
aacttaatat tattactatc ttttataaaa tctagattta ttttaaagat aaatagaaga     300
tagctttcag gatatatttt aggttatata aatagttaat tacttttttt aagctagtaa     360
atattctaag tatattctaa tattatatta actagatctt acataacttt ctagataaat     420
ttgcctttat atacttagat aatatatta ttttactaa tagcttatta aaaaagtatt     480
ataattatat ataattaatt ttctagaaac taggcaaagc aggactatag cttaatatta     540
ataaatataa ttttaaaatt aactaagtct ttaagattta ttattaatat aaagaagggt     600
atataaatag atcctaagaa aataagctat ccttaaataa taaatcctta tattagttaa     660
aaaaaatata cttcttttta agatttataa attttatata atttatataa aacttcttag     720
acctgatata cctacttact attctaatat aaaaaattat taaattttta tagattaaga     780
agtataccta gtttaaatag ctaaattaaa tatttataat aacttctatt tttatataat     840
ttaatcctaa ttaagaaata attttaaag ctcttatatt aaactagact actagaaaaa     900
tattattata atataataat aataaagtac tatattttta tatttattat ttaagaactc     960
tccctgcaaa atataattat aaaatttata ataaaaatta ttagtaatta ttaatagctt    1020
aaaagtttag aaattagagc ttataagttt aaaaaatttt attattatta taaattataa    1080
aaacctacta tactttacta taattagata ttttaataaa tagtaaatat attagacaga    1140
tatacttaat tattttaatt ttatttaaa tattaactag gtaagctagc agctttgcct    1200
agatatatta ttatactata aataagatat actagccagg gtagacaata attaacttaa    1260
aatatataaa aaatagctac taaaactgaa taatattaaa gaatagtatt tatctaagta    1320
taacttaaat cttagtaata ctaagaatt taattaatta attaaaatat ataaatatag    1380
ttgaccttga aactgttact aaactttatt ataatattat taattataat aactaagcta    1440
agaataaatt acttaagaaa ctataaaaaa tagtctagga gaataataaa gctctataaa    1500
aaattattaa gattattaag aagaatagat agagcttcct aagagattac aaatatatat    1560
cttattttct aaatatttaa tattatctag agataatttt ttttattctt aattttaggt    1620
cctgggaagt aaacctttaa aaacctaaat tatatagatc tggattaact agctacccctg    1680
ggcaaaacag cctatatatt atatatatta attcttaata atctagtagt atatcttttt    1740
tacctattat agatcaagag attaaaacta gctagggcta atatataata aaatttgttt    1800
ttacttagtt acttattagt ttgtcaatcc gcaccgcaac ccgcagcggg tcaccacact    1860
gcag                                                                 1864

<210> SEQ ID NO 5
<211> LENGTH: 28
<212> TYPE: DNA
<213> ORGANISM: Aspergillus niger

<400> SEQUENCE: 5
atgtcgttcc gatctctact cgccctga                                        28

<210> SEQ ID NO 6
<211> LENGTH: 10
```

```
<212> TYPE: PRT
<213> ORGANISM: Aspergillus niger

<400> SEQUENCE: 6

Met Ser Phe Arg Ser Leu Leu Ala Leu Ser
1               5                   10

<210> SEQ ID NO 7
<211> LENGTH: 7
<212> TYPE: DNA
<213> ORGANISM: Unknown
<220> FEATURE:
<223> OTHER INFORMATION: eukaryotic promoter sequence

<400> SEQUENCE: 7 tataaat                                                              7

<210> SEQ ID NO 8
<211> LENGTH: 4
<212> TYPE: DNA
<213> ORGANISM: Unknown
<220> FEATURE:
<223> OTHER INFORMATION: eukaryotic promoter sequence

<400> SEQUENCE: 8 caat                                                                 4

<210> SEQ ID NO 9
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 9
gctcggggtt ggcagctgag atcaccag                                      28

<210> SEQ ID NO 10
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 10
actcccccac cgcaatgagg tgtctcgt                                      28

<210> SEQ ID NO 11
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 11
gatccatcga tctcgagatc gatc                                          24

<210> SEQ ID NO 12
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 12
tgatttccaa gcgcgctgag atcaccag                                      28
```

<210> SEQ ID NO 13
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 13
tgagcaacga agcggctgag atcaccag                                          28

<210> SEQ ID NO 14
<211> LENGTH: 5
<212> TYPE: PRT
<213> ORGANISM: Rhizomucor miehei

<400> SEQUENCE: 14

Tyr Tyr Phe Trp Asp
1               5

<210> SEQ ID NO 15
<211> LENGTH: 17
<212> TYPE: DNA
<213> ORGANISM: Rhizomucor miehei

<400> SEQUENCE: 15
gcrtcccara artarta                                                      17

<210> SEQ ID NO 16
<211> LENGTH: 18
<212> TYPE: PRT
<213> ORGANISM: Humicola grisea
<220> FEATURE:
<221> NAME/KEY: MISC_FEATURE
<222> LOCATION: (15)..(15)
<223> OTHER INFORMATION: the x at position 15 can be any amino acid.

<400> SEQUENCE: 16

Ala Ala Val Asp Thr Phe Ile Asn Thr Glu Lys Pro Ser Ala Xaa Asn
1               5                   10                  15

Ser Leu

<210> SEQ ID NO 17
<211> LENGTH: 26
<212> TYPE: PRT
<213> ORGANISM: Humicola grisea
<220> FEATURE:
<221> NAME/KEY: MISC_FEATURE
<222> LOCATION: (14)..(14)
<223> OTHER INFORMATION: the x at position 14 can be any amino acid.
<221> NAME/KEY: MISC_FEATURE
<222> LOCATION: (24)..(24)
<223> OTHER INFORMATION: the x at position 24 can be any amino acid.

<400> SEQUENCE: 17

Pro Leu Trp Ser Ile Thr Val Pro Ile Lys Ala Thr Gly Xaa Ala Val
1               5                   10                  15

Gln Tyr Lys Tyr Ile Lys Val Xaa Gln Leu
            20                  25

<210> SEQ ID NO 18
<211> LENGTH: 25
<212> TYPE: PRT
<213> ORGANISM: Humicola grisea
<220> FEATURE:
<221> NAME/KEY: MISC_FEATURE

```
<222> LOCATION: (17)..(17)
<223> OTHER INFORMATION: the x at position 17 can be any amino acid.

<400> SEQUENCE: 18

Ala Ala Val Arg Pro Leu Ile Asn Pro Glu Lys Pro Ile Ala Trp Asn
1               5                   10                  15
Xaa Leu Lys Ala Asn Ile Gly Pro Asn
            20                  25

<210> SEQ ID NO 19
<211> LENGTH: 39
<212> TYPE: PRT
<213> ORGANISM: Humicola grisea

<400> SEQUENCE: 19

Ile Asn Thr Glu Lys Pro Ile Ala Trp Asn Lys Leu Leu Ala Asn Ile
1               5                   10                  15
Gly Pro Asn Gly Lys Ala Ala Pro Gly Ala Ala Ala Gly Val Val Ile
            20                  25                  30
Ala Ser Pro Ser Arg Thr Asp
            35

<210> SEQ ID NO 20
<211> LENGTH: 17
<212> TYPE: DNA
<213> ORGANISM: Artificial Sequence
<220> FEATURE:
<223> OTHER INFORMATION: synthetic oligonucleotide probes

<400> SEQUENCE: 20
cartayaart ayathaa                                                  17

<210> SEQ ID NO 21
<211> LENGTH: 6
<212> TYPE: PRT
<213> ORGANISM: Artificial Sequence
<220> FEATURE:
<223> OTHER INFORMATION: synthetic oligonucleotide probes

<400> SEQUENCE: 21

Gln Tyr Lys Tyr Ile Lys
1               5

<210> SEQ ID NO 22
<211> LENGTH: 17
<212> TYPE: DNA
<213> ORGANISM: Artificial Sequence
<220> FEATURE:
<223> OTHER INFORMATION: synthetic oligonucleotide probes

<400> SEQUENCE: 22
cartayaart atattaa                                                  17

<210> SEQ ID NO 23
<211> LENGTH: 17
<212> TYPE: DNA
<213> ORGANISM: Artificial Sequence
<220> FEATURE:
<223> OTHER INFORMATION: synthetic oligonucleotide probes

<400> SEQUENCE: 23
cartayaart acattaa                                                  17

<210> SEQ ID NO 24
```

```
<211> LENGTH: 17
<212> TYPE: DNA
<213> ORGANISM: Artificial Sequence
<220> FEATURE:
<223> OTHER INFORMATION: synthetic olibonucleotide probe

<400> SEQUENCE: 24
cartayaart atatcaa                                              17

<210> SEQ ID NO 25
<211> LENGTH: 17
<212> TYPE: DNA
<213> ORGANISM: Artificial Sequence
<220> FEATURE:
<223> OTHER INFORMATION: synthetic oligonucleotide probe

<400> SEQUENCE: 25
cartayaart acatcaa                                              17

<210> SEQ ID NO 26
<211> LENGTH: 17
<212> TYPE: DNA
<213> ORGANISM: Artificial Sequence
<220> FEATURE:
<223> OTHER INFORMATION: synthetic oligonucleotide probe

<400> SEQUENCE: 26
cartayaart atataaa                                              17

<210> SEQ ID NO 27
<211> LENGTH: 17
<212> TYPE: DNA
<213> ORGANISM: Artificial Sequence
<220> FEATURE:
<223> OTHER INFORMATION: synthetic oligonucleotide probe

<400> SEQUENCE: 27
cartayaart acataaa                                              17

<210> SEQ ID NO 28
<211> LENGTH: 17
<212> TYPE: DNA
<213> ORGANISM: Artificial Sequence
<220> FEATURE:
<223> OTHER INFORMATION: oligonucleotide probe

<400> SEQUENCE: 28
cagtacaagt atatcaa                                              17
```

HETEROLOGOUS POLYPEPTIDES EXPRESSED IN FILAMENTOUS FUNGI, PROCESSES FOR MAKING SAME, AND VECTORS FOR MAKING SAME

This is a continuation of U.S. patent application Ser. No. 08/484,384, filed Jun. 7, 1995, now U.S. Pat. No. 6,004,785; which is a continuation of U.S. patent application Ser. No. 08/284,942, filed Aug. 2, 1994, now U.S. Pat. No. 5,578,463; which is a continuation of U.S. patent application Ser. No. 07/413,010, filed Sep. 25, 1989, now U.S. Pat. No. 5,364,770; which is a continuation of U.S. patent application Ser. No. 07/163,219, filed Feb. 26, 1988, abandoned; which is a continuation of U.S. patent application Ser. No. 06/882,224, filed Jul. 7, 1986, abandoned; which is a continuation-in-part of U.S. patent application Ser. No. 06/771,374, filed Aug. 29, 1985, abandoned.

FIELD OF THE INVENTION

The present invention is directed to heterologous polypeptides expressed and secreted by filamentous fungi and to vectors and processes for expressing and secreting such polypeptides. More particularly, the invention discloses transformation vectors and processes using the same for expressing and secreting biologically active bovine chymosin and heterologous glucoamylase by a filamentous fungus.

BACKGROUND OF THE INVENTION

The expression of DNA sequences encoding heterologous polypeptides (i.e., polypeptides not normally expressed and secreted by a host organism) has advanced to a state of considerable sophistication. For example, it has been reported that various DNA sequences encoding pharmacologically desirable polypeptides [e.g., human growth hormone (1), human tissue plasminogen activator (2), various human interferons (6), urokinase (5), Factor VIII (4), and human serum albumin (3)] and industrially important enzymes [e.g., chymosin (7), alpha amylases (8), and alkaline proteases (9)] have been cloned and expressed in a number of different expression hosts. Such expression has been achieved by transforming prokaryotic organisms [e.g., *E. coli* (10) or *B. subtilis* (11)] or eukaryotic organisms [e.g., *Saccharomyces cerevisiae* (7), *Kluyveromyces lactis* (12) or Chinese Hamster Ovary cells (2)] with DNA sequences encoding the heterologous polypeptide.

Some polypeptides, when expressed in heterologous hosts, do not have the same level of biological activity as their naturally produced counterparts when expressed in various host organisms. For example, bovine chymosin has very low biological activity when expressed by *E. coli* (13) or *S. cerevisiae* (7). This reduced biological activity in *E. coli* is not due to the natural inability of *E. coli* to glycosylate the polypeptide since chymosin is not normally glycosylated (14). Such relative inactivity, both in *E. coli* and *S. cerevisiae*, however, appears to be primarily due to improper folding of the polypeptide chain as evidenced by the partial post expression activation of such expressed polypeptides by various procedures. In such procedures, expressed chymosin may be sequentially denatured and renatured in a number of ways to increase biological activity: e.g., treatment with urea (13), exposure to denaturing/renaturing pH (13) and denaturation and cleavage of disulfide bonds followed by renaturation and regeneration of covalent sulfur linkages (15). Such denaturation/renaturation procedures, however, are not highly efficient [e.g., 30% or less recovery of biological activity for rennin (13)], and add considerable time and expense in producing a biologically active polypeptide.

Other heterologous polypeptides are preferably expressed in higher eukaryotic hosts (e.g., mammalian cells). Such polypeptides are usually glycopoly-peptides which require an expression host which can recognize and glycosylate certain amino acid sequences in the heterologous polypeptide. Such mammalian tissue culture systems, however, often do not secrete large amounts of heterologous polypeptides when compared with microbial systems. Moreover, such systems are technically difficult to maintain and consequently are expensive to operate.

Transformation and expression in a filamentous fungus involving complementation of aroD mutants of *N. crassa* lacking biosynthetic dehydroquinase has been reported (16). Since then, transformation based on complementation of glutamate dehydrogenase deficient *N. crassa* mutants has also been developed (17). In each case the dehydroquinase (ga2) and glutamate dehydrogenase (am) genes used for complementation were derived from *N. crassa* and therefore involved homologous expression. Other examples of homologous expression in filamentous fungi include the complementation of the auxotrophic markers trpC, (18) and argB (19) in *A. nidulans* and the transformation of *A. nidulans* to acetamide or acrylamide utilization by expression of the *A. nidulans* gene encoding acetamidase (20).

Expression of heterologous polypeptides in filamentous fungi has been limited to the transformation and expression of fungal and bacterial polypeptides. For example, *A. nidulans*, deficient in orotidine-5'-phosphate decarboxylase, has been transformed with a plasmid containing DNA sequences encoding the pyr4 gene derived from *N. crassa* (21,32). *A. niger* has also been transformed to utilize acetamide and acrylamide by expression of the gene encoding acetamidase derived from *A. nidulans* (22).

Examples of heterologous expression of bacterial polypeptides in filamentous fungi include the expression of a bacterial phosphotransferase in *N. crassa* (23) Dictyostelium discoideum (24) and *Cephalosporium acremonium* (25).

In each of these examples of homologous and heterologous fungal expression, the expressed polypeptides were maintained intracellularly in the filamentous fungi.

Accordingly, an object of the invention herein is to provide for the expression and secretion of heterologous polypeptides by and from filamentous fungi including vectors for transforming such fungi and processes for expressing and secreting such heterologous polypeptides.

SUMMARY OF THE INVENTION

The inventor includes novel vectors for expressing and secreting heterologous polypeptides from filamentous fungi. Such vectors are used in novel processes to express and secrete such heterologous polypeptides. The vectors used for transforming a filamentous fungus to express and secrete a heterologous polypeptide include a DNA sequence encoding a heterologous polypeptide and a DNA sequence encoding a signal sequence which is functional in a secretory system in a given filamentous fungus and which is operably linked to the sequence encoding the heterologous polypeptide. Such signal sequences may be the signal sequence normally associated with the heterologous polypeptides or may be derived from other sources.

The vector may also contain DNA sequences encoding a promoter sequence which is functionally recognized by the filamentous fungus and which is operably linked to the DNA sequence encoding the signal sequence. Preferably functional polyadenylation sequences are operably linked to the 3' terminus of the DNA sequence encoding the heterologous polypeptides.

Each of the above described vectors are used in novel processes to transform a filamentous fungus wherein the DNA sequences encoding the signal sequence and heterologous polypeptide are expressed. The thus synthesized polypeptide is thereafter secreted from the filamentous fungus.

BRIEF DESCRIPTION OF THE DRAWINGS

FIG. 8A–D show the strategy used to generate mp 19 GAPR$^A$C1–$^A$C4 from mp 19 GAPR.

FIGS. 11A, B and C (SEQ ID NOS: 2 and 3)is the DNA sequence of *Mucor miehei*, carboxyl protease including the entire coding sequence and 5' and 3' flanking sequences.

FIGS. 13A-1, A-2 and B (SEQ ID NO: 4)are a partial nucleotide and restriction map of ANS-1.

DETAILED DESCRIPTION

Figure 1:
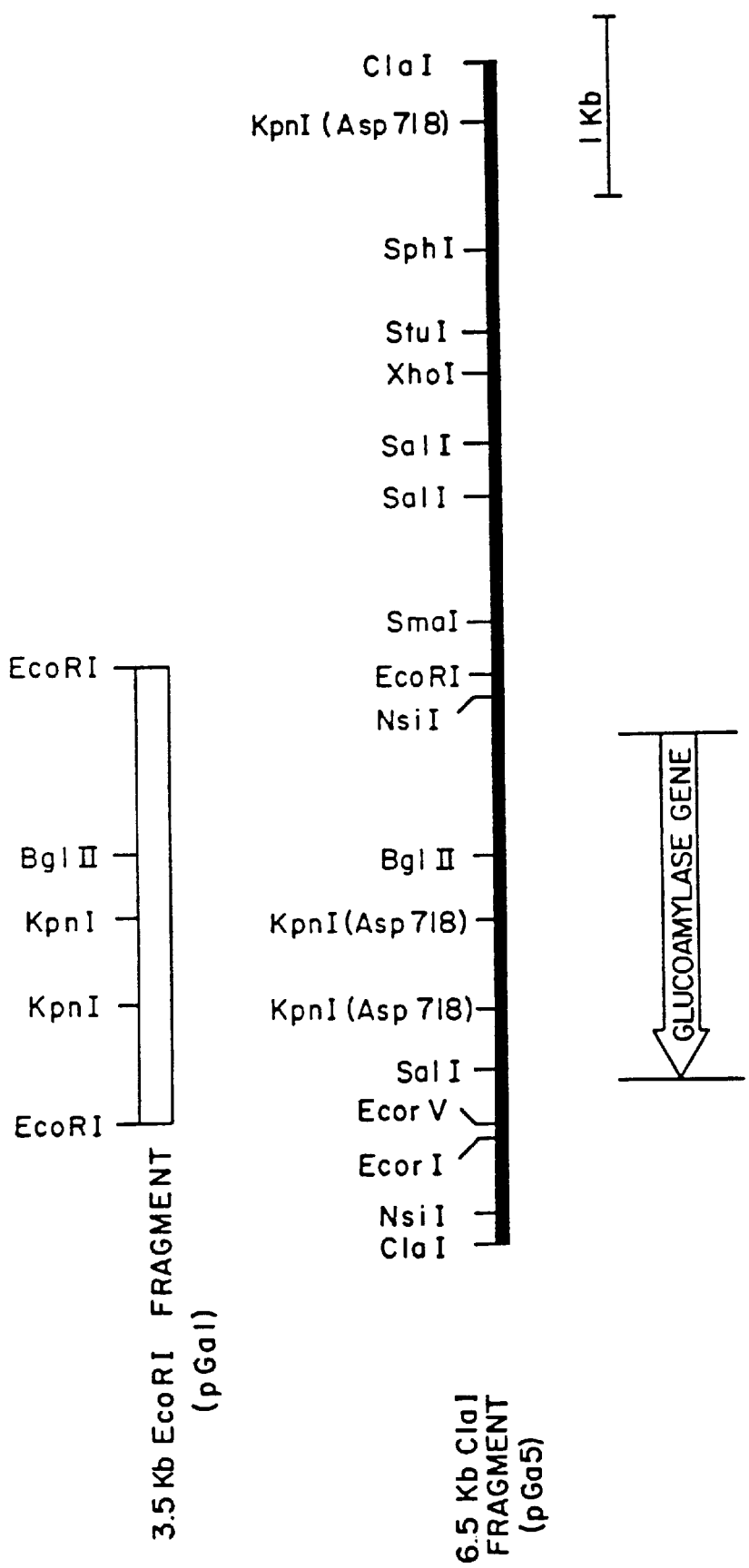
FIG. 1 is a restriction map of the *Aspergillus niger* glucoamylase inserts in pGa1 and pGa5.

The inventors have demonstrated that heterologous polypeptides from widely divergent sources can be expressed and secreted by filamentous fungi. Specifically, bovine chymosin, glucoamylase from *Aspergillus niger* and *Humicola grises* and the carboxyl protease from *Mucor miehei* have been expressed in and secreted from *A. nidulans*. In addition, bovine chymosin has been expressed and secreted from *A. awamori* and *Trichoderma reesei*. Biologically active chymosin was detected in the culture medium without further treatment. This result was surprising in that the vectors used to transform *A. nidulans* were constructed to secrete prochymosin which requires exposure to an acidic environment (approximately pH 2) to produce biologically active chymosin.

In general, a vector containing DNA sequences encoding functional promoter and terminator sequences (including polyadenylation sequences) are operably linked to DNA sequences encoding various signal sequences and heterologous polypeptides. The thus constructed vectors are used to transform a filamentous fungus. Viable transformants may thereafter be identified by screening for the expression and secretion of the heterologous polypeptide.

Alternatively, an expressible selection characteristic may be used to isolate transformants by incorporating DNA sequences encoding the selection characteristic into the transformation vector. Examples of such selection characteristics include resistance to various antibiotics, (e.g., aminoglycosides, benomyl etc.) and sequences encoding genes which complement an auxotrophic defect (e.g. pyr4 complementation of pyr4 deficient *A. nidulans, A. awamori* or *Trichoderma reesei* or AraB complementation of ArgB deficient *A. nidulans* or *A. awamori*) or sequences encoding genes which confer a nutritional (e.g., acetamidase) or morphological marker in the expression host.

In the preferred embodiments disclosed a DNA sequence encoding the ANS-1 sequence derived from *A. nidulans* is included in the construction of the transformation vectors of the present invention. This sequence increases the transformation efficiency of the vector. Such sequences, however, are not considered to be absolutely necessary to practice the invention.

In addition, certain DNA sequences derived from the bacterial plasmid pBR325 form part of the disclosed transformation vectors. These sequences also are not believed to be necessary for transforming filamentous fungi. These sequences instead provide for bacterial replication of the vectors during vector construction. Other plasmid sequences which may also be used during vector construction include pBR322 (ATCC 37017), RK-2 (ATCC 37125), pMB9 (ATCC 37019) and pSC101 (ATCC 37032).

The disclosed preferred embodiments are presented by way of example and are not intended to limit the scope of the invention.

DEFINITIONS

By "expressing polypeptides" is meant the expression of DNA sequences encoding the polypeptide.

"Polypeptides" are polymers of α-amino acids which are covalently linked through peptide bonds. Polypeptides include low molecular weight polymers as well as high molecular weight polymers more commonly referred to as proteins. In addition, a polypeptide can be a phosphopolypeptide, glycopolypeptide or metallopolypeptide. Further, one or more polymer chains may be combined to form a polypeptide.

As used herein a "heterologous polypeptide" is a polypeptide which is not normally expressed and secreted by the filamentous fungus used to express that particular polypeptide. Heterologous polypeptides include polypeptides derived from prokaryotic sources (e.g., α-amylase from Bacillus species, alkaline protease from Bacillus species, and various hydrolytic enzymes from Pseudomonas, etc.), polypeptides derived from eukaryotic sources (e.g., bovine chymosin, human tissue plasminogen activator, human growth hormone, human interferon, urokinase, human serum albumin, factor VIII etc.), and polypeptides derived from fungal sources other than the expression host (e.g., glucoamylase from *A. niger* and *Humicola grisea* expressed in *A. nidulans*, the carboxyl protease from *Mucor miehei* expressed in *A. nidulans*, etc.).

Heterologous polypeptides also include hybrid polypeptides which comprise a combination of partial or complete polypeptide sequences derived from at least two different polypeptides each of which may be homologous or heterologous with regard to the fungal expression host. Examples of such hybrid polypeptides include: 1) DNA sequences encoding prochymosin fused to DNA sequences encoding the *A. niger* glucoamylase signal and pro sequence alone or in conjunction with various amounts of amino-terminal mature glucoamylase codons, and 2) DNA sequences encoding fungal glucoamylase, or any fungal carboxy protease, human tissue plasminogen activator or human growth hormone fused to DNA sequences encoding a functional signal sequence alone or in conjunction with various amounts of amino-terminal propeptide condons or mature codons associated with the functional signal.

Further, the heterologous polypeptides of the present invention also include: 1) naturally occuring allellic variations that may exist or occur in the sequence of polypeptides derived from the above prokaryotic, eukaryotic and fungal sources as well as those used to form the above hybrid polypeptides, and 2) engineered variations in the above heterologous polypeptides brought about, for example, by way of site specific mutagenesis wherein various deletions, insertions or substitutions of one or more of the amino acids in the heterologous polypeptides are produced.

A "biochemically active heterologous polypeptide" is a heterologous polypeptide which is secreted in active form as evidenced by its ability to mediate: 1) the biochemical activity mediated by its naturally occurring counterpart, or 2) in the case of hybrid polypeptides, the biochemical activity mediated by at least one of the naturally occurring counterparts comprising the hybrid polypeptides.

Each of the above defined heterologous polypeptides is encoded by a heterologous DNA sequence which contains a stop signal which is recognized by the filamentous fungus in which expression and secretion occurs. When recognized by the host, the stop signal terminates translation of the mRNA encoding the heterologous polypeptide.

The "filamentous fungi" of the present invention are eukaryotic microorganisms and include all filamentous forms of the subdivision Eumycotina (26). These fungi are characterized by a vegatative mycelium composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism is obligately aerobic. In contrast, vegetative growth by yeasts such as *S. cerevisiae* is by budding of a unicellular thallus, and carbon catabolism may be fermentative. *S. cerevisiae* has a prominent, very stable diploid phase whereas, diploids exist only briefly prior to meiosis in filamentous fungi like Aspergilli and Neurospora. *S. cervisiae* has 17 chromosomes as opposed to 8 and 7 for *A. nidulans* and *N. crassa* respectively. Recent illustrations of differences between *S. cerevisiae* and filamentous fungi include the inability of *S. cerevisiae* to process Asperaillus and Trichoderma introns and the inability to recognize many transcriptional regulators of filamentous fungi (27).

Various species of filamentous fungi may be used as expression hosts including the following genera: Asperaillus, Trichoderma, Neurospora, Podospora, Endothia Mucor, Cochiobolus and Pyricularia. Specific expression hosts include *A. nidulans* (18, 19, 20, 21, 61), *A. niger* (22), *A. awomari*, e.g., NRRL 3112, ATCC 22342 (NRRL 3112), ATCC 44733, ATCC 14331 and strain UVK 143f, *A. oryzae*, e.g., ATCC 11490, *N. crassa* (16, 17, 23), *Trichoderma reesei*, e.g. NRRL 15709, ATCC 13631, 56764, 56765, 56466, 56767, and *Trichoderma viride*, e.g., ATCC 32098 and 32086.

As used herein, a "promotor sequence" is a DNA sequence which is recognized by the particular filamentous fungus for expression purposes. It is operably linked to a DNA sequence encoding the above defined polypeptides. Such linkage comprises positioning of the promoter with respect to the initiation codon of the DNA sequence encoding the signal sequence of the disclosed transformation vectors. The promoter sequence contains transcription and translation control sequences which mediate the expression of the signal sequence and heterologous polypeptide. Examples include the promoter from *A. niger* glucoamylase (39,48), the *Mucor miehei* carboxyl protease herein, and *A. niger* α-glucosidase (28), *Trichoderma reesei* cellobiohydrolase I (29), *A. nidulans* trpC (18) and higher eukaryotic promoters such as the SV40 early promoter (24).

Likewise a "terminator sequence" is a DNA sequence which is recognized by the expression host to terminate transcription. It is operably linked to the 3' end of the DNA encoding the heterologous polypeptide to be expressed. Examples include the terminator from *A. nidulans* trpC (18), *A. niger* glucoamylase (39,48), *A. niger* α-glucosidase (28), and the *Mucor miehei* carboxyl protease herein, although any fungal terminator is likely to be functional in the present invention.

A "polyadenylation sequence" is a DNA sequence which when transcribed is recognized by the expression host to add polyadenosine residues to transcribed mRNA. It is operably linked to the 3' end of the DNA encoding the heterologous polypeptide to be expressed. Examples include polyadenylation sequences from *A. nidulans* trpC (18), *A. niger* glucoamylase (39,48), *A. niger* α-glucosidase (28), and the *Mucor miehei* carboxyl protease herein. Any fungal polyadenylation sequence, however, is likely to be functional in the present invention.

A "signal sequence" is an amino acid sequence which when operably linked to the amino-terminus of a heterologous polypeptide permits the secretion of such heterologus polypeptide from the host filamentous fungus. Such signal sequences may be the signal sequence normally associated with the heterologous polypeptide (i.e., a native signal sequence) or may be derived from other sources (i.e., a foreign signal sequence). Signal sequences are operably linked to a heterologous polypeptide either by utilizing a native signal sequence or by joining a DNA sequence encoding a foreign signal sequence to a DNA sequence encoding the heterologous polypeptide in the proper reading frame to permit translation of the signal sequence and heterologous polypeptide. Signal sequences useful in practicing the present invention include signals derived from bovine preprochymosin (15), *A. niger* glucoamylase (39), the *Mucor miehei* carboxyl protease herein and *Trichoderma reesei* cellulases (29). However, any signal sequence capable of permitting secretion of a heterologous polypeptide is contemplated by the present invention.

A "propeptide" or "pro sequence" is an amino acid sequence positioned at the amino terminus of a mature biologically active polypeptide. When so positioned the resultant polypeptide is called a zymogen. Zymogens, generally, are biologically inactive and can be converted to mature active polypeptides by catalytic or autocatalytic cleavage of the propeptide from the zymogen.

In one embodiment of the invention a "transformation vector" is a DNA sequence encoding a heterologous polypeptide and a DNA sequence encoding a heterologous or homologous signal sequence operably linked thereto. In addition, a transformation vector may include DNA sequences encoding functional promoter and polyadenylation sequences. Each of the above transformation vectors may also include sequences encoding an expressible selection characteristic as well as sequences which increase the efficiency of fungal transformation.

"Transformation" is a process wherein a transformation vector is introduced into a filamentous fungus. The methods of transformation of the present invention have resulted in the stable integration of all or part of the transformation vector into the genome of the filamentous fungus. However, transformation resulting in the maintenance of a self-replicating extra-chromosomal transformation vector is also contemplated.

GENERAL METHODS

"Digestion" of DNA refers to catalytic cleavage of the DNA with an enzyme that acts only at certain locations in the DNA. Such enzymes are called restriction enzymes, and the sites for which each is specific is called a restriction site. "Partial" digestion refers to incomplete digestion by a restriction enzyme, i.e., conditions are chosen that result in cleavage of some but not all of the sites for a given restriction endonuclease in a DNA substrate. The various restriction enzymes used herein are commercially available and their reaction conditions, cofactors and other requirements as established by the enzyme suppliers were used. In general, about 1 microgram of plasmid or DNA fragment is used with about 1 unit of enzyme and about 20 microliters of buffer solution. Appropriate buffers and substrate amounts with particular restriction enzymes are specified by the manufacturer. Incubation times of about one hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme may be followed by bacterial alkaline phosphatase hydrolysis of the terminal 5' phosphates to prevent the two ends of a DNA fragment from forming a closed loop that would impede insertion of another DNA fragment at the restriction site upon ligation.

"Recovery" or "isolation" of a given fragment of DNA from a restriction digest means separation of the digest by a polyacrylamide gel electrophoresis, identification of the fragment of interest, removal of the gel section containing the desired fragment, and separation of the DNA from the gel generally by electroelution (30).

"Ligation" refers to the process of forming phosphodiester bonds between two double-stranded nucleic acid fragments (30). Unless otherwise stated, ligation was accomplished using known buffers in conditions with one unit of T4 DNA ligase ("ligase") per 0.5 microgram of approximately equal molar amounts of the DNA fragments to be ligated.

"Oligonucleotides" are short length single or double stranded polydeoxynucleotides which were chemically synthesized by the method of Crea et al., (31) and then purified on polyacrylamide gels.

"Transformation" means introducing DNA in to an organism so that the DNA is maintained, either as an extrachromosomal element or chromosomal integrant. Unless otherwise stated, the method used herein for transformation of *E. coli* was the $CaCl_2$ method (30).

*A. nidulans* strain G191 (University of Glasgow culture collection) was transformed by incubating *A. nidulans* sphaeroplasts with the transformation vector. The genotype of strain G191 is pabaA1 (requires p-aminobenzoic acid), fwA1 (a color marker), mauA2 (monoamine non-utilizing), and pyrG89 (deficient for orotidine phosphate decarboxlase). Sphaeroplasts were prepared by the cellophane method of Ballance et al. (21) with the following modifications. To digest *A. nidulans* cell walls, Novozyme 234 (Novo Industries, Denmark) was first partially purified. A 100 to 500 mg sample of Novozyme 234 was dissolved in 2.5 ml of 0.6M KCl. The 2.5 ml aliquot was loaded into a PD10 column (Pharmacia-Upsulla, Sweden) equilibrated with 0.6M KCl. The enzymes were eluted with 3.5 ml of the same buffer.

Cellophane discs were incubated in Novozyme 234 (5 mg/ml) for 2 hours, then washed with 0.6M KCl. The digest and washings were combined, filtered through miracloth (Calbiochem-Behring Corp., La Jolla, Calif.), and washed as described (21). Centrifugations were in 50 or 15 ml conical tubes at ca. 1000Xg for 10 min. Following incubation on ice for 20 min, 2 ml of the polyethylene glycol 4000 solution (250 mg/ml) was added, incubated at room temperature for 5 min. followed by the addition of 4 ml of 0.6M KCl, 50 mM $CaCl_2$. Transformed protoplasts were centrifuged, resuspended in 0.6M KCl, 50mM $CaCl_2$, and plated as described (21). Zero controls comprised protoplasts incubated with 20 µl of 20 mM Tris-HCl, 1 mM EDTA, pH7.4 without plasmid DNA. Positive controls comprised transformation with 5 µg of pDJB3 constructed as described herein. Regeneration frequencies were determined by plating dilutions on minimal media supplemented with 5–10 ppm paba and 500 ppm uridine. Regeneration ranged from 0.5 to 5%.

Because of the low transformation frequencies associated with pDJBl, the derivative containing the Mucor acid protease gene (pMeJB1-7) was expected to give extremely low transformation frequencies. Consequently, to obtain pmeJB11-7 transformants of *A. nidulans*, cotransformation was used. This was accomplished by first constructing a non-selectable vector containing ANS-1, and then transforming sphaeroplasts with a mixture of pmeJB1-7 and the non-selectable vector containing the ANS-1 fragment. The rationale for this approach was that the ANS-1 bearing vector would integrate in multiple copies and provide regions of homology for pMeJB1-7 integration. The ANS-1 vector was prepared by subcloning the PstI-PvuII fragment of ANS-1 (FIGS. 12A and 13B) from pDJB-3 into pUC18 (33).

The two plasmids (pMeJB1-7 and the ANS-1 containing vector) were mixed (2.5 µg each) and the above mentioned transformation protocol followed.

Transformants obtained with vectors PGRG1-pGRG4 and pDJB-gam were transferred after 3 or 4 days incubation at 37° C. Minimal media agar plates supplemented with 5 ppm p-aminobenzoic acid were centrally inoculated with mycelial transfers from transformants. Three to five days following inoculation of minimal medium plates, spore suspensions were prepared by vortexing a mycelial fragment in 1 ml distilled $H_2O$, 0.02% tween-80. Approximately $5 \times 10^4$ spores were inoculated into 250 ml baffled flasks containing 50 ml of the following medium: (g/l) Maltodextrin M-040 (Grain Processing Corp., Muscatine, Iowa) 50 g, $NaNO_3$ 6 g, $MgSO_4.7H20$ 0.5 g, KCl 0.52 g, $KH_2PO_4$, 68 g, 1 ml trace element solution (34), 1 ml MAZU DF-60P antifoam (Mazer Chemicals, Inc., Gurnee, Ill.), 10 ppm p-aminobenzoic acid, and 50 ppm streptomycin sulfate. Alternatives to MAZU, such as bovine serum albumin or other appropriate surfactant may be used. Mucor acid protease secretion was tested in Aspergillus complete medium (20 g dextrose, 1 g peptone, 20 g malt extract per liter). Carbon source regulation of chymosin secretion by *Aspergillus nidulans* transformants was assessed by measuring secretion in the above-mentioned starch medium relative to the same medium supplemented with 1% fructose, sucrose, or dextrose instead of 5% starch. In all cases, the media were incubated at 37°

C. on a rotary shaker (150 rpm). A pDJB3-derived transformant was included as a control.

Western blots of the various secreted chymosins and *Mucor miehei* carboxyl protease were performed according to Towbin, et. al (35). Due to the high concentration of salt in chymosin culture broths and the effect this salt has on gel electrophoresis a desalting step was necessary. Pre-poured G-25 columns (Pharmacia, PD10) were equilibrated with 50 mM $Na_2HPO_4$, pH 6.0. A 2.5 ml aliquot of culture broth was applied to the column. The protein was eluted with 3.5 ml of the same buffer. The heterologous polypeptides present on the blots were detected by contacting the nitrocellulose blots first with rabbit anti-chymosin (36) or rabbit anti-*Mucor miehei* carboxy protease serum (36). The blots were next contacted with goat-anti-rabbit serum conjugated with horseradish peroxidase (Bio-Rad, Richmond, Calif.) and developed. Prior to loading on the gels, 50 μl of medium (desalted in the case of chymosin) was mixed with 25 μl of SDS sample buffer. β-mercaptoethanol was added to a final concetration of 1%. The sample was heated in a 95° C. bath for 5 minutes after which 40–50 μl of sample was loaded on the gel. Each gel was also loaded with 2 μl each of 650, 65 and 6.5 μg/ml chymosin standards and molecular weight markers. Western blots of pmeDJ1-7 transformants were similarly analyzed except that gel permeation was not performed.

Protease activity was detected as described by Sokol, et. al. (37). Luria broth was supplemented with 1–1.5% skim milk (Difco) and 30–35 ml was poured into a 150 mm petri dish. An aliquot of 2 to 5 μl of culture medium was spotted on the plate. The plate was incubated over night at 37° C. in a humidity box. The activity was determined based on the amount of milk clotting occurring on the plate measured in mm. The plates were co-spotted with dilutions of 100 CHU/ml or 16.6 CHU/ml rennin (CHU-Chr Hansen Unit, Chr Hansen's Laboratorium, A./S., Copenhagen). The relationship between the diameter of the coagulation zone (mm) and the centration of enzyme is logarithmic.

In order to distinguish between types of proteases, pepstatin, an inhibitor of the chymosin type of carboxyl protease, was used to inhibit protease activity attributable to chymosin. Samples of chymosin mutants and control broths were preincubated with a 1:100 dilution of 10 mM pepstatin in DMSO for 5 minutes before analyzing for protease activity.

Glucoamylase secretion by pDJB-gam-1 transformants in 5% starch media was assessed using an assay based on the ability of glucoamylase to catalyze the conversion of p-nitrophenol-a-glucopyranoside (PNPAG) (38) to free glucose and p-nitrophenoxide. The substrate, PNPAG, was dissolved in DMSO at 150 mg/ml and 3 to 15 μl aliquots were diluted to 200 μl with 0.2 M sodium acetate, 1 mM calcium chloride at pH 4.3. A 25 μl sample was placed into a microtitre plate well. An equal volume of standards ranging from 0 to 10 Sigma *A. niger* units/ml (Sigma Chemical Co., St. Louis, Mo.) were placed in separate wells. To each well, 200 μl of PNPAG solution at 2.25 to 11.25 mg/ml was added. The reaction was allowed to proceed at 60° C. for 0.5 to 1 hour. The time depended upon the concentration of enzyme. The reaction was terminated by the addition of 50 μl of 2 M trizma base. The plate was read at 405 nm. The concentration of enzyme was calculated from a standard curve.

Unless otherwise stated, chromosomal DNA was extracted from filamentous fungi by the following procedure. The filamentous fungus was grown in an appropriate medium broth for 3 to 4 days. Mycelia were harvested by filtering the culture through fine cheesecloth. The mycelia were rinsed thoroughly in a buffer of 50mM tris-HCl, pH7.5, 5 mM EDTA. Excess liquid was removed by squeezing the mycelia in the cheesecloth. About 3 to 5 grams of wet mycelia were combined with an equivalent amount of sterile, acid-washed sand in a mortar and pestle. The mixture was ground for five minutes to form a fine paste. The mixture was ground for another five minutes after adding 10 ml of 50 mM tris-HCl, pH 7.5, 5 mM EDTA. The slurry was poured into a 50 ml capped centrifuge tube and extracted with 25 ml of phenol-chloroform (equilibrated with an equal volume of 50 mM tris-HCl, pH 7.5, 5 mM EDTA). The phases were separated by low speed centrifugation. The aqueous phase was saved and reextracted three times. The aqueous phases were combined (about 20 ml total volume) and mixed with 2 ml of 3 M sodium acetate, pH 5.4 in sterile centrifuge tubes. Ice cold isopropanol (25 ml) was added and the tubes were placed at −20° C. for one hour. The tubes were then centrifuged at high speed to pellet the nucleic acids, and the supernatant fluid was discarded. Pellets were allowed to air dry for 30 minutes before resuspending in 400 μl of 10 mM tris-HCl, pH 7.5, 1 mM EDTA (TE buffer). Pancreatic ribonuclease (Sigma Chemical Co., St. Louis, Mo.) was added to a final concentration of 10 μg per ml, and the tubes were incubated for 30 minutes at room temperature (30). Ribonuclease was then removed by extraction with phenol-chloroform. The aqueous layer was carefully removed and placed in a tube which contained 40 μl of 3M sodium acetate, pH 5.4. Ice cold ethanol was layered into the solution. The DNA precipitated at the interface and was spooled onto a glass rod. This DNA was dried and resuspended in a small volume (100 to 200 μl) of TE buffer. The concentration of DNA was determined spectrophotometrically at 260 nm (30).

To confirm the chromosomal integration of chymosin DNA sequences in selected transformants Southern hybridizations were performed (30). Spore suspensions of transformants were inoculated into Aspergillus complete medium and incubated at 37° C. on a rotary shaker for 24–48 hrs. The medium was non-selective in that it was supplemented with 5 ppm p-aminobenzoic acid and contained sufficient uracil for growth of the auxotrophic parent. In effect, these Southerns also tested for the stability of the transformants. The mycelium was filtered, ground in sand, and the DNA purified as previously described. Transformant DNA was then digested with various restriction enzymes and fragments separated by agarose gel electrophoresis. Control lanes included digested pDJB3 transformant DNA and undigested DNA. Gels were stained with ethidium bromide, photographed, blotted to nitrocellulose or nytran (Schleicher and Schuell, Keene, N.H.), and probed with radiolabeled plasmids or specific fragments.

EXAMPLE 1

Expression and Secretion of *Aspergillus niger* Glucoamylase By *Aspergillus nidulans*

A. Construction of pGA1

*Aspergillus niger* (Culture #7, Culture Collection Genencor, Inc., South San Francisco, Calif.) was grown in potato dextrose broth (Difco, Detroit, Mich.) at 30° C. for 3 days with vigorous aeration. Chromosomal DNA was extracted as previously described.

A synthetic oligonucleotide was used as a hybridization probe to detect the glucoamylase gene from *Aspergillus niger*. The oligonucleotide was 28 bases in length (28 mer)

and corresponded to the first 9⅓ codons of the published glucoamylase coding sequence (39):

MetSerPheArgSerLeuLeuAlaLeuSer (SEQ ID NO: 5)
5'ATGTCGTTCCGATCTCTACTCGCCCTGA 3' (SEQ ID NO: 6)

The oligonucleotide was synthesized on a Biosearch automated DNA synthesizer (Biosearch, San Rafael, Calif.) using the reagents and protocols specified by the manufacturer.

Genomic DNA from *Aspergillus niger* was analyzed for the presence of glucoamylase sequences by the method of Southern (30). Briefly, 10 μg of *Aspergillus niger* DNA was digested with EcoR1 restriction endonuclease. The digested DNA was subjected to electrophoresis on a 1% agarose gel according to standard methods (30). DNA was transferred from the gel to a nitrocellulose membrane (Schleicher & Schuell, Inc., Keene, N.H.) by blotting in 10×SSC (1.5 M NaCl, 0.15 M trisodium citrate) (30). DNA was fixed to the nitrocellulose by baking in an 80° C. vacuum oven, followed by hybridization at low stringency (2,40) with radiolabeled oligonucleotide probe. Radiolabeling of the synthetic oligonucleotide was done at 37° C. in a 50μl reaction that contained 70 mM tris-HCl, pH 7.5, 10 mM $MgCl_2$, 5 mM dithiothreitol, 30 pmoles of synthetic oligonucleotide, 20 pmoles of gamma-[32P]ATP (Amersham, Chicago, Ill.; specific activity 5000 Ci/mmol), and 5 units of T4 polynucleotide kinase (New England Biolabs). After hybridization, the filters were washed 15 minutes in 2×SSC, 0.1% sodium dodecylsulfate (SDS) and twice in 2×SSC at 37° C. Filters were air dried, wrapped in Saran-Wrap (Dow Chemical) and applied to Kodak X0mat-AR X-ray film at −70° C. to obtain an autoradiographic image. After developing the autoradiogram, a band of hybridization was clearly visible corresponding to a 3.5 kilobase-pair EcoR1 fragment.

Genomic DNA from *Aspergillus niger* was digested with EcoR1 and size-fractionated by polyacrylamide gel electrophoresis according to standard methods (30). DNA fragments 3 to 4 kb in size were excised and eluted from the gel (30). This DNA fraction was used to generate a library of clones in the *Escherichia coli* cloning vector pBR322 (ATCC 37017). The cloning vector was cleaved with EcoR1 and dephosphorylated with bacterial alkaline phosphatase (Bethesda Research Labs). A typical dephosphorylation reaction consisted of 1 μg of digested vector DNA and 1 unit of alkaline phosphatase in 50 μl of 50 mM tris-HCl, pH 8.0, 50 mM NaCl. The reaction was incubated at 65° C. for one hour. The phosphatase was removed by extraction with phenol-chloroform. The EcoR1, size-selected *Aspergillus niger* DNA was then ligated with EcoR1 cleaved and dephosphorylated pBR322. A typical ligation reaction contained the following: 100 ng each of vector and insert DNAs, 1 unit of T4 DNA ligase (Bethesda Research Labs), 25 mM tris-HCl, pH 7.5, 10 mM $MgCl_2$, 10 mM dithiothreitol, and 1 mM ATP in a 10 μl volume. Ligation reactions were incubated at 16° C. for 18 to 24 hours. The ligated DNA was used to transform competent *E. coli* 294 cells (ATCC 31446) prepared by the method of Morrison (41). Transformants were selected on LB agar plates (30) which contained carbenecillin at a final concentration of 50 μg per ml. Transformants which harbored glucoamylase gene sequences were identified by colony hybridization methods (30) using the glucoamylase-specific 28 mer as a probe. Hybridizing colonies were purified, and plasmid DNAs were isolated from each by the alkaline-SDS miniscreen procedure (30). The plasmids selected in this manner all contained a 3.5 kb EcoR1 fragment which hybridized to the synthetic glucoamylase probe. One such plasmid, designated pGa1, was selected for further analysis. A 1.1 kb EcoR1-BglII fragment from the insert in pGa1 was subcloned into M13 mp9 (42) and partially sequenced by the dideoxy chain termination method (43) to confirm that the cloned DNA encoded the glucoamylase gene. A restriction endonuclease cleavage map of the 3.5 kb EcoR1 fragment contained in pGa1 is depicted in FIG. 1. It was generated by single and double restriction digests followed by orientation of the DNA fragments with respect to known restriction sites in pBR322 (44).

B. Construction of pGa5

The nucleotide sequence and restriction map of pGa1 indicated that pGa1 contained the entire glucoamylase coding region and 221 nucleotides of 5' flanking DNA. The sequences in this 5' region were strikingly similar to typical eukaryotic promoter sequences with TATAAAT (SEQ ID NO: 7) and CAAT (SEQ ID NO: 8) boxes located upstream of the ATG start codon (48).

However, to insure that possible upstream activation sites of the *Aspergillus niger* glucoamylase gene were included in the final transformation vector a larger genomic fragment which contained at least 1000 bp of 5' flanking DNA was cloned. Southern blotting experiments similar to those already described identified a 6.5 kb ClaI fragment which hybridized to a radiolabeled EcoRI glucoamylase fragment from pGa1. The EcoRI fragment was radiolabeled by nick translation (30) with alpha-[32P]dCTP (Amersham; specific activity 3000 Ci/mmol). A nick translation kit (Bethesda Research Labs) was used for the labeling reaction by following the instructions supplied by the manufacturer. Filters were hybridized and washed under stringent conditions (30).

The 6.5 kb ClaI fragment identified by hybridization was cloned in a manner similar to that described previously. *Aspergillus niger* DNA was digested with ClaI and size-fractionated by polyacrylamide gel electrophoresis. DNA fragments migrating between 5.5 and 8 kb were excised and eluted from the gel. This fraction was ligated to ClaI cleaved and dephosporylated pBR325 (45). The ligation mixture was used to transform competent *E. coli* 294 cells. Transformants were selected on LB agar plates containing carbenecillin (50 μg/ml). Colonies which contained glucoamylase gene sequences were identified by colony hybridization (30). Plasmid DNA extracted from hybridizing colonies contained a 6.5 kb ClaI fragment which included the 3.5 kb EcoR1 fragment cloned previously in pGa1. These recombinant plasmids encoded the *Aspergillus niger* glucoamylase gene as confirmed by supercoil-DNA sequencing (46) with the synthetic oligonucleotide (28 mer) as a sequencing primer. A restriction endonuclease cleavage map of the 6.5 kb ClaI fragment was constructed using single and double digests of the DNA cloned in pBR325. Restriction sites in the vector DNA were used as reference points to orient the fragment. This restriction map is shown in FIG. 1. Location of the glucoamylase gene was deduced by comparing restriction sites of pGa5 to those of the previously published glucoamylase genes (39, 47, 48). From the mapping data it was estimated that approximately 3.3 kb of the 5'-flanking DNA and about 1 kb of 3'-flanking DNA were contained within the cloned fragment.

Plasmid pGa5 was deposited with the ATCC on Aug. 28, 1985 in *E. coli* 294 and has been assigned number 53249.

C. Vector for Expression and Secretion of *Aspergillus niger* Glucoamylase

Figure 2:
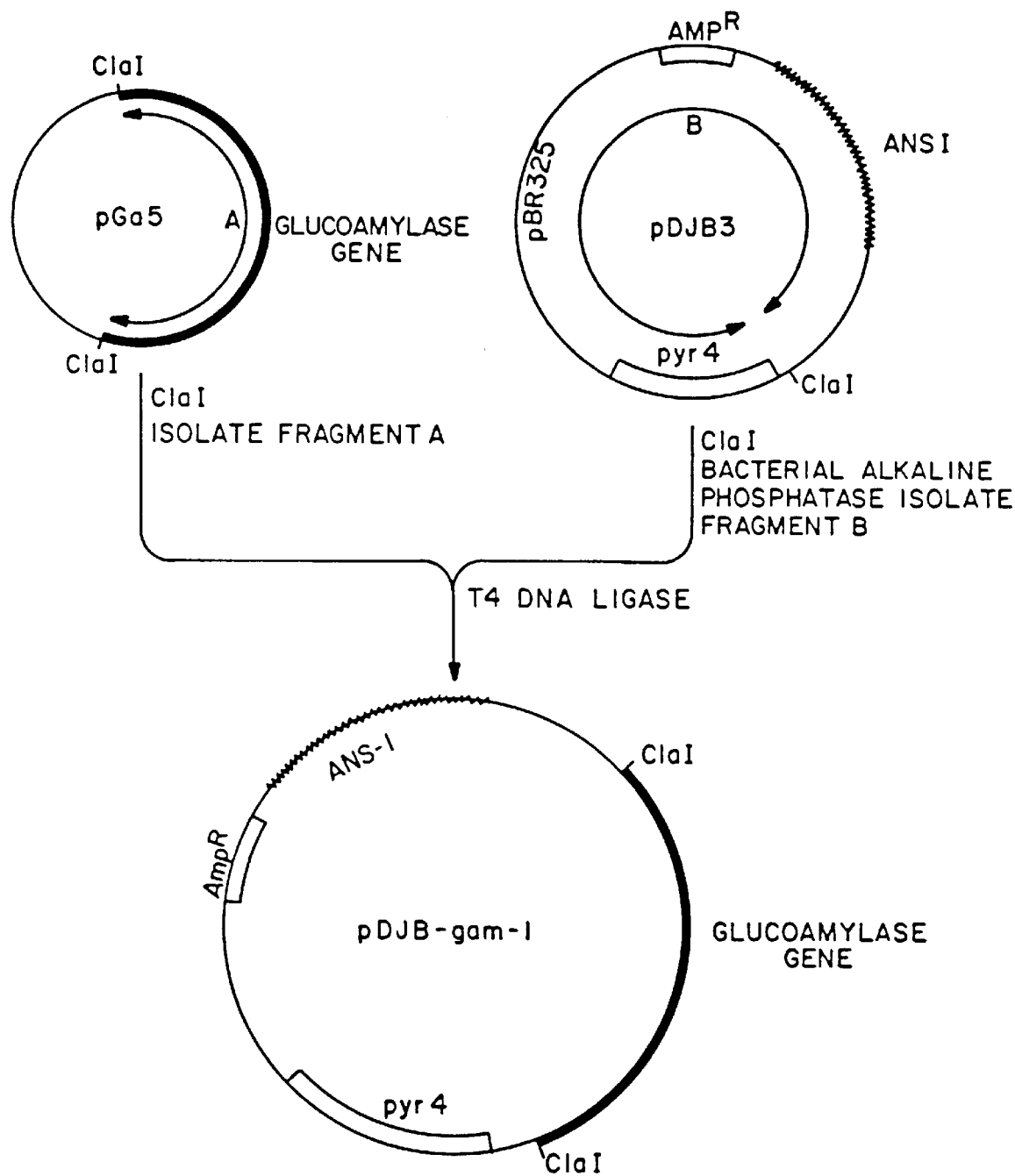
FIG. 2 depicts the construction of pDJB-gam-1.
Figure 13B:
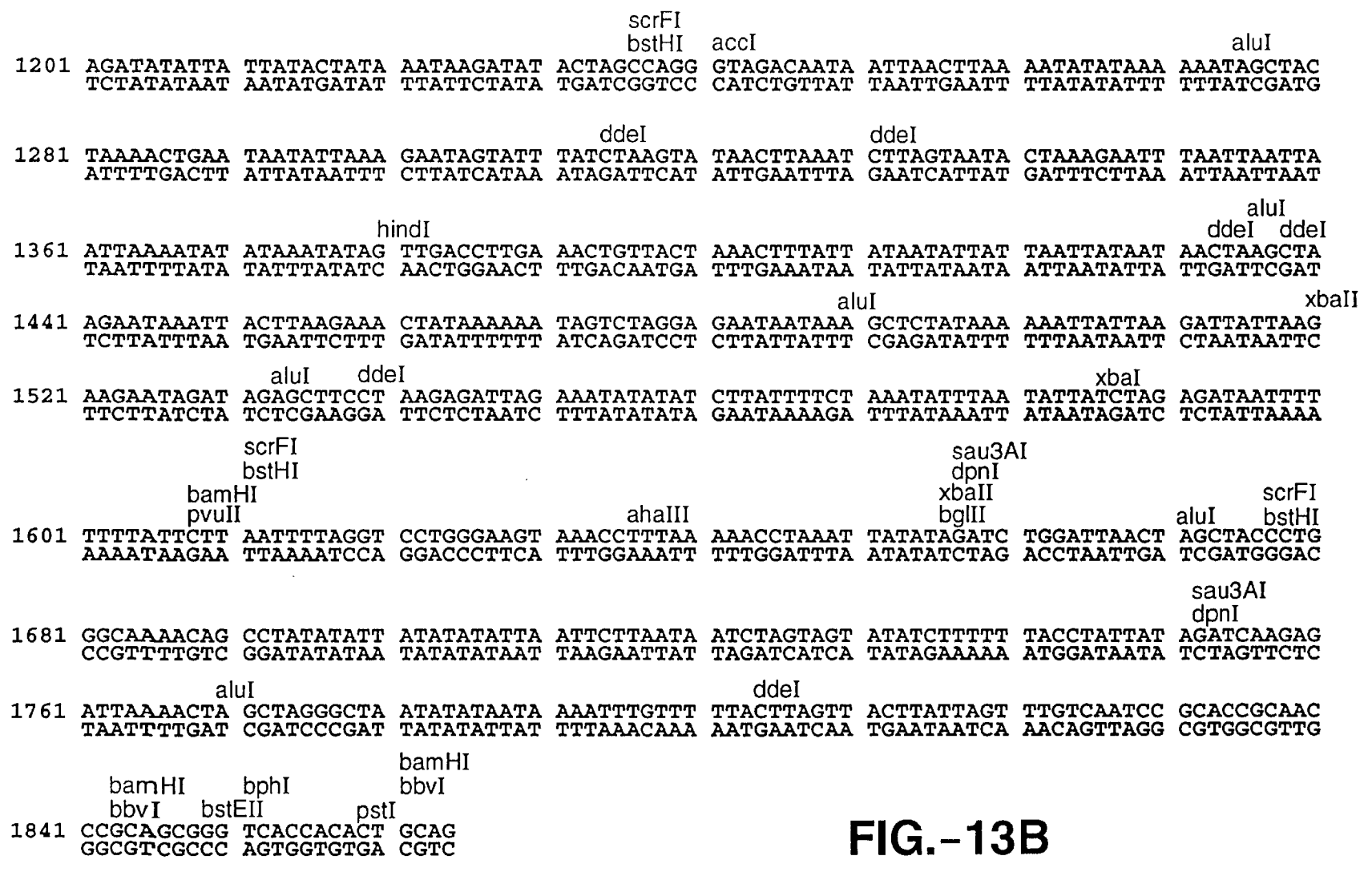
Figure 14:
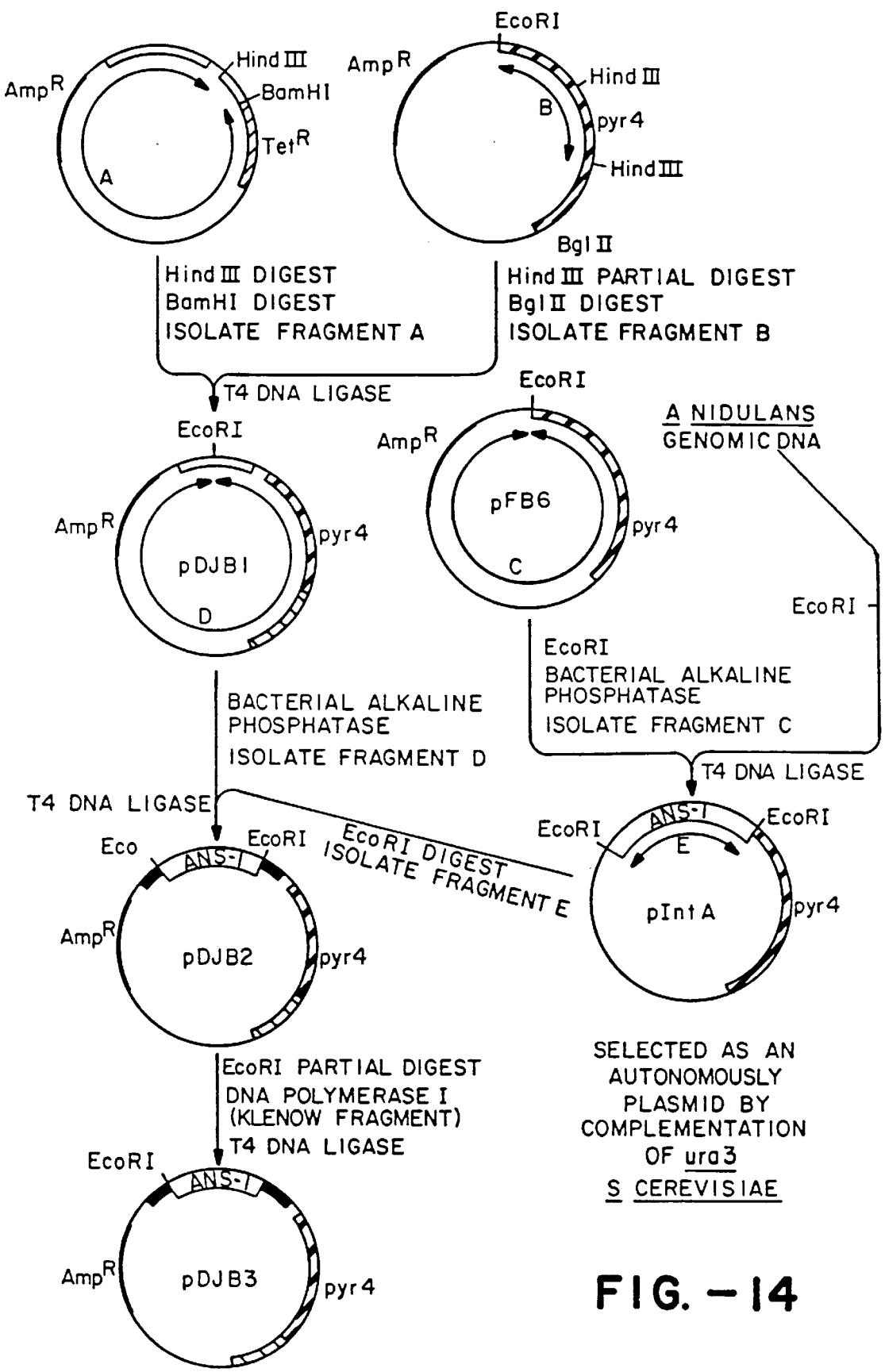
FIG. 14 depicts the construction of pDJB-3.

The 6.5 kb ClaI fragment from PGa5 containing the glucoamylase gene was cloned into the *E. coli.*—*Aspergillus nidulans* shuttle vector pDJB3 as depicted in FIG. 2. The pDJB3 shuttle vector possesses a selectable beta-lactamase gene and origin or replication from *E. coli* plasmid pBR325, the pyr4 gene from *Neuospora crassa* which relieves the auxotrophic requirement for uridine in *Aspergillus nidulans* strain G191, a sequence know as ANS1 from *Aspergillus nidulans* which promotes a high frequency of stable integrative transformants in *Aspergillus nidulans*, unique EcoR1 and ClaI restriction sites for cloning. pDJB is constructed as depicted in FIG. 14. Plasmid pFB6 (32) is digested to completion with BgrlII and partially digested with HindIII. Fragment B containing the pyr4 gene (ca. 2 Kb) is purified by gel electrophoresis and ligated into HindIII/Bam HI digested pBR325 (fragment A) yielding plasmid pDJB1. The ANS-1 sequence is cloned by ligating EcoRI digested *A. nidulans* genomic DNA (strain G191 or other FGSC#4-derived strains) into EcoR1 cleaved pFB6. The resulting pool of EcoRI fragments in pFB6 is used to transform a ura3 *S. cerevisiae* (E.G. ATCC 44769, 44770 etc.). An autonomously replicating plasmid, pINtA, is purified from the *S. cerevisiae* transformant. pIntA is digested with EcoRI, the ANS-1 fragment is purified by gel electrophoresis and ligated into EcoRI digested pDJB1, yielding plasmid pDJB2. pDJB2 is partially digested with EcoRI, treated with DNA polymerase I (Klenow), and re-ligated to yield plasmid pDJB3. The partial nucleotide sequence and restriction map of the ANS-1 fragment is shown in FIGS. 13A and 13B (SEQ ID NO: 4).

Plasmid pGa5 was digested with ClaI and the large fragment (fragment A) was separated from the vector by agarose gel electrophoresis. This fragment was ligated with pDJB3 which had been cleaved with ClaI and dephosphorylated (fragment B). The ligation mixture was used to transform competent *E. coli* 294 cells. Transformants were selected on LB agar supplemented with carbenecillin (50 μg/ml). Analysis of plasmid DNAs from these transformants indicated that the glucoamylase fragment had been inserted as expected. Both orientations of the glucoamylase fragment were obtained by screening various transformants. One plasmid, designated pDJB-gam1 was arbitrarily chosen for transformation of *Aspergillus nidulans* protoplasts.

D. Expression and Secretion of Glucoamylase

*Aspergillus nidulans* Strain G191 was transformed with pDJB-gam-1 as previously described. Five transformants designated pDJB-gam-1-4, 9, 10, 11 & 13 were analyzed for glucoamylase activity as previously described. The results are shown in Table I.

TABLE I

| Sample | Glucoamylase Activity (Sigma Units/ml) |
|---|---|
| pDJB3 | 0.129 |
| ppJB-gam-1-4 | 0.684 |
| pDJB-gam-1-9 | 0.662 |
| PDJB-gam-1-10 | 0.131 |
| pDJB-gam-1-11 | 0.509 |
| pDJB-gam-1-13 | 0.565 |
| A. niger | 2.698 |

As can be seen, each pDJB-gam-1 transformant produced more glucoamylase activity than the control indicating that biologically active glucoamylase was expressed and secreted from the transformed fungi.

EXAMPLE 2

Expression and Secretion of Bovine Chymosin from *Asperaillus nidulans*

Expression vectors were constructed encoding either a natural precursor of bovine chymosin (preprochymosin) or a fusion precursor in which DNA sequences for *Aspergillus niger* glucoamylase and prochymosin were precisely fused. The strategy for the construction of these vectors involved the following steps. First, a DNA sequence containing a portion of the glucoamylase promoter and a portion of the glucoamylase 5'-coding region was cloned upstream from a DNA sequence corresponding to the amino-terminal portion of preprochymosin. Next, nucleotides between the DNA fragments were deleted by M13 site-specific mutagenesis (40) using specific primer sequences. Finally, a segment of DNA containing the fused sequences was incorporated with the remaining portion of the prochymosin sequence into an expression vector which employed the 5'- and 3'-regulatory sequences of the *Aspergillus niger* glucoamylase gene. These steps are outlined in FIGS. 3 through 7.

A. Construction of mp19 GAPR

Figure 3:
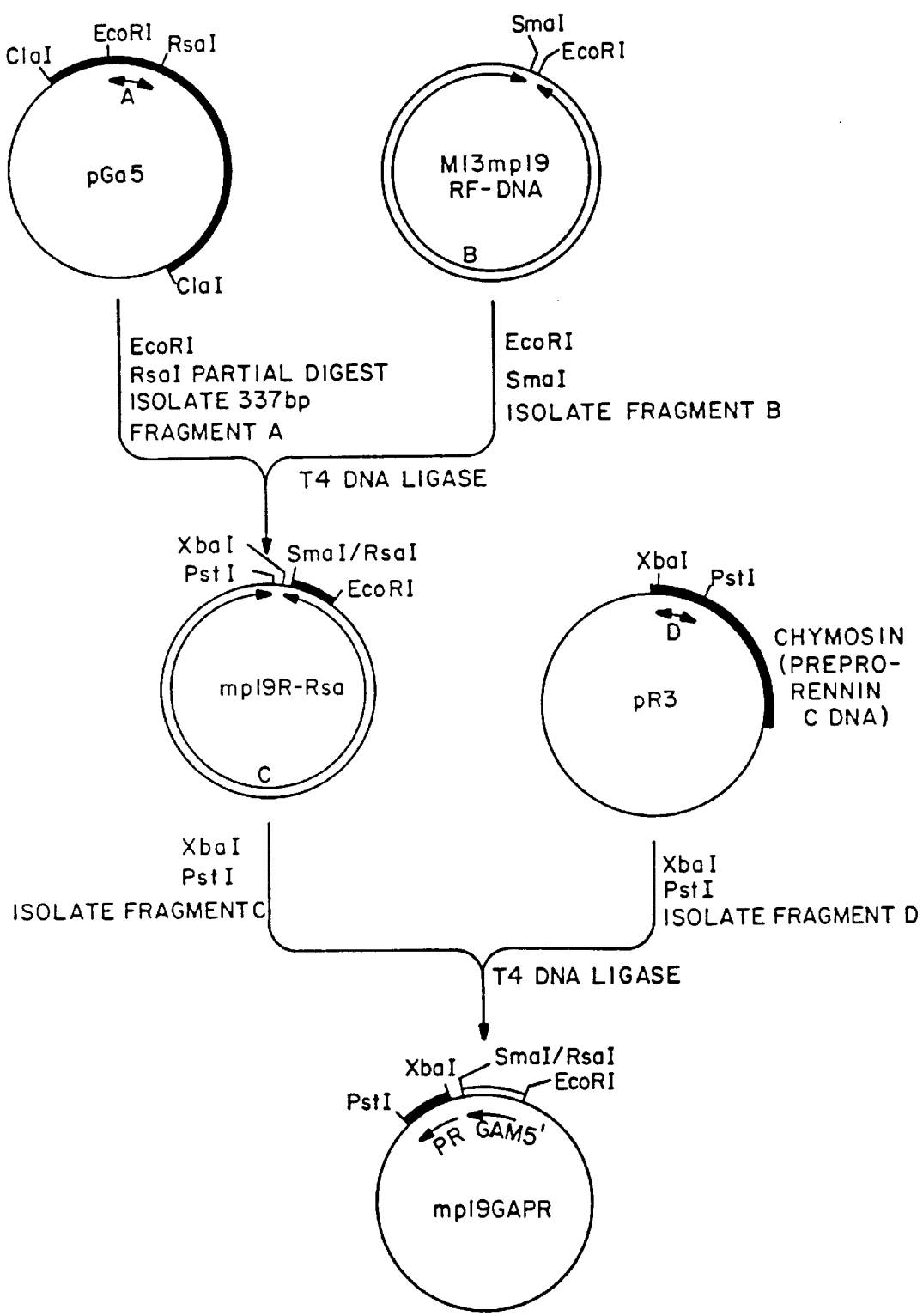
FIG. 3 depicts the construction of mp19GAPR.

Plasmid pGa5 is used to derive a 337 bp EcoR1-RsaI DNA fragment (fragment A) bearing a portion of the glucoamylase promoter and an amino-terminal segment of the coding region. Fragment A was ligated with EcoR1 and SmaI digested M13mp19 RF-DNA (fragment B). The ligation mixture was used to transform *E. coli*. JM101 (ATCC 33876). Clear plaques were analyzed for the presence of fragment A by restriction analysis of the corresponding RF-DNA. One isolate containing fragment A, designated mp19R-Rsa was digested with PstI and XbaI and the large fragment (fragment C) was isolated. A small XbaI-PstI sequence (fragment D) derived from pR3 (49) containing 5' preprochymosin sequences; was purified by electrophoresis and ligated to fragment C to produce the phage template mp19GAPR as shown in FIG. 3.

B. Site Specific Deletion Mutagenesis

As shown in FIG. 8 mp19GAPRΔC1 was derived from mp19 GAPR by deleting the nucleotides between the glucoamylase signal peptide codons and the codons for prochymosin by site-specific mutagenesis. Thus, in mp19GAPRΔC1 the glucoamylase signal peptide codons are precisely fused to the first codon of prochymosin. Site-specific mutagenesis was done as previously described (40) except that only one oligonucleotide was used to prime second strand synthesis on the single-stranded M13 template (FIG. 4) (40). The synthetic oligonucleotide used to derive mp19GAPRΔC1 (primer 1) was 5' GCTCGGGGTTG-GCAGCTGAGATCACCA G 3' (SEQ ID NO: 9). Plaques containing the desired deletion were identified by hybridization with the primer radio-labeled as previously described.

In mp19GAPRΔC3 the nucleotides between those immediately preceding the initiation codon of glucoamylase and the ATG start codon of preprochymosin were joined by site-specific mutagenesis using the synthetic oligonucleotide (primer 3)

5' ACTCCCCCACCGCAATGAGGTGTCTCGT 3' (SEQ ID NO: 10).

The resulting mutation linked the glucoamylase promoter region precisely to the initiation codon of preprochymosin as depicted in FIG. 8.

C. Construction of Vectors for the Expression and Secretion of Bovine Chymosin

Figure 4:
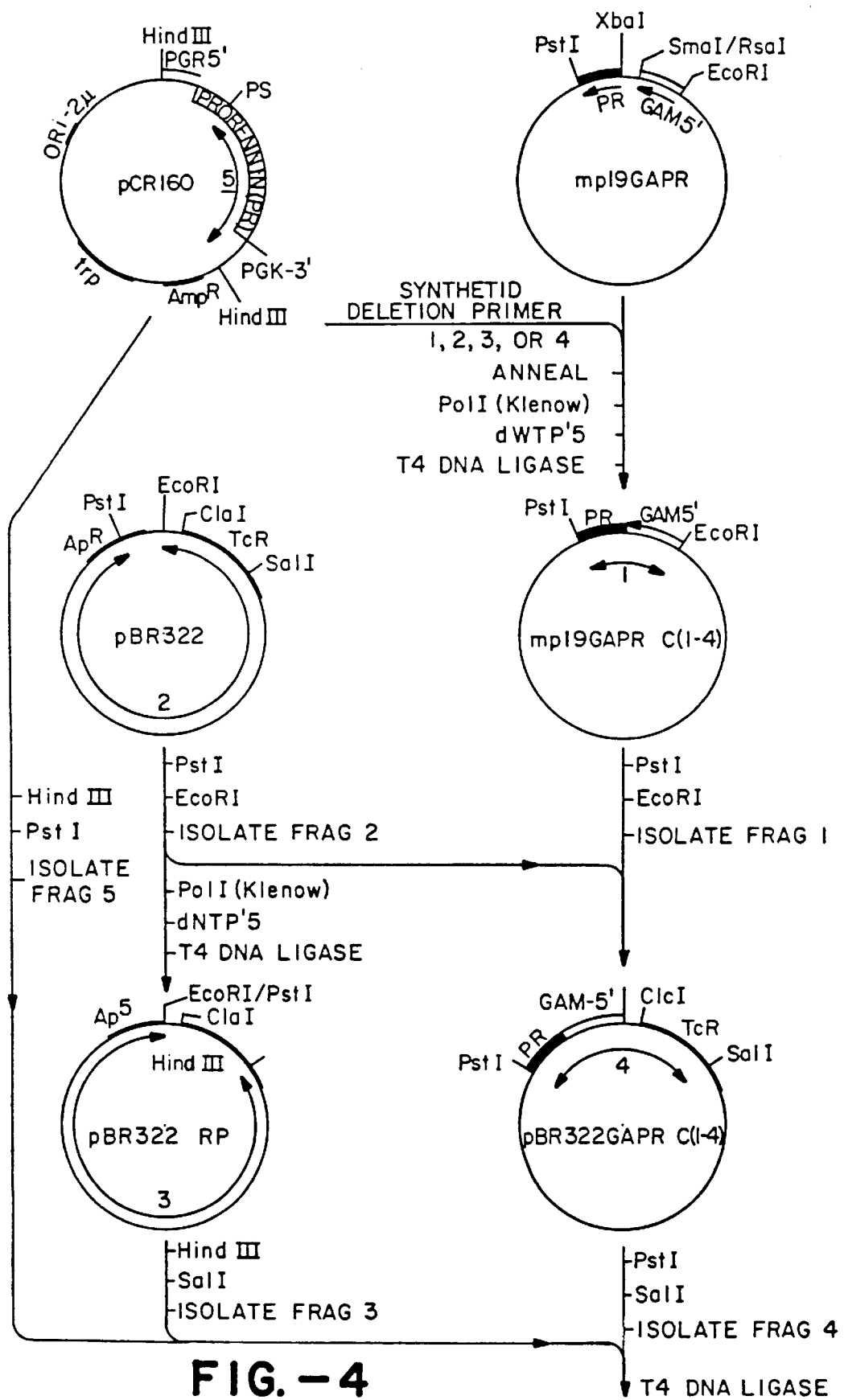
FIGS. 4, 5, 6 (SEQ ID NO:1), and 7 depict the construction of pGRG1, pGRG2, pGRG3, and pGRG4.
Figure 5:
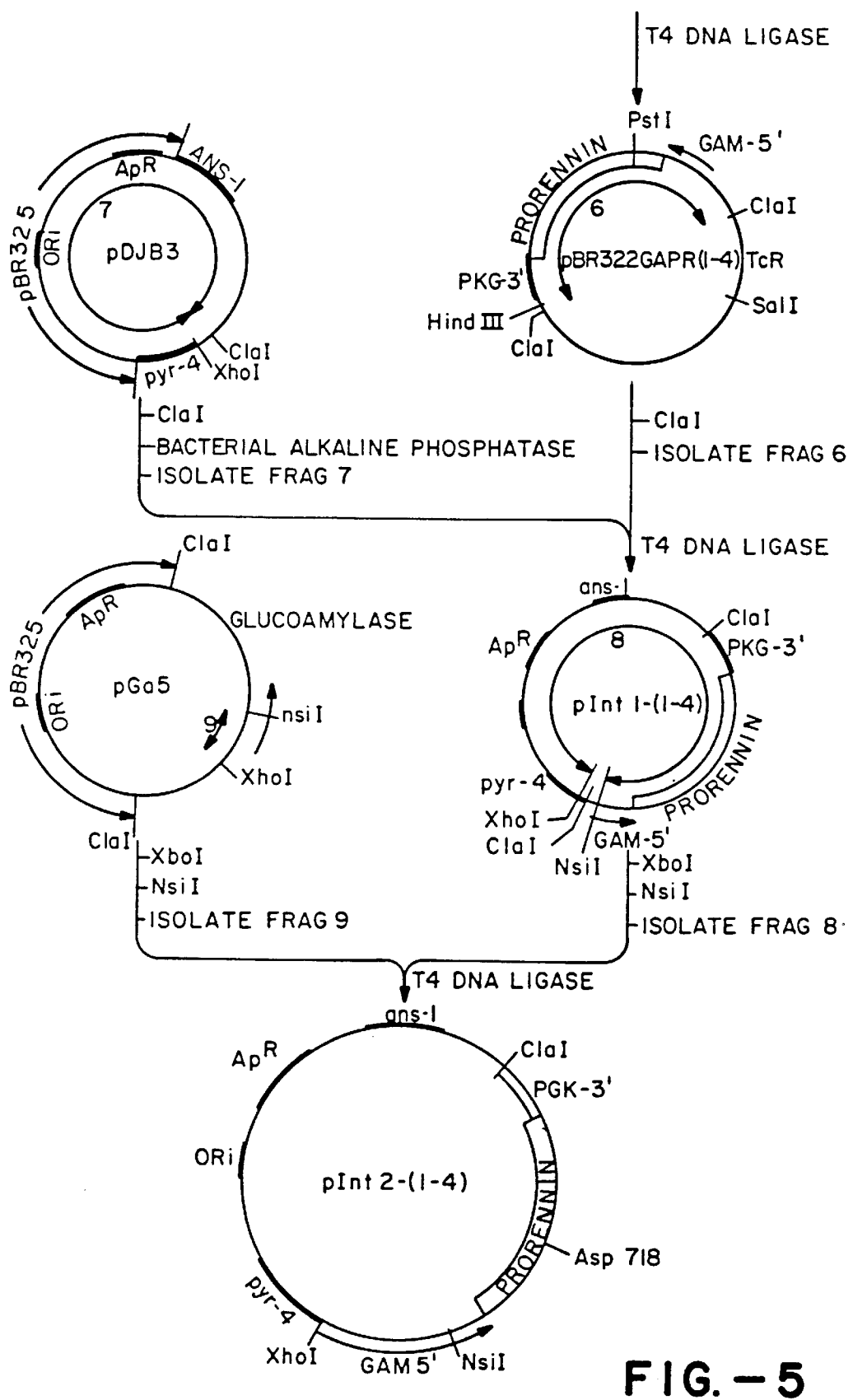

As further depicted in FIG. 4 each of the fusions between the glucoamylase sequences and 5' prochymosin sequences (m19GAPRΔC1 and mp19GAPRΔC3) were combined with the 3' prochymosin sequences and the *Saccharomyces cerevisiae* phosphoglyceratekinase (PGK) terminator in the *Aspergillus nidulans* transformation vector pDJB3. The replicative form of mp19GAPRΔC1 and mp19GAPRΔC3 was digested with EcoR1 and PstI. The smaller fragment (fragment 1) was isolated. Plasmid pBR322 was also digested with EcoR1 and PstI and the larger vector fragment (fragment 2) was isolated. Fragments 1 and 2 were joined by ligation and used to transform E. coli. 294. A tetracycline resistant colony containing either plasmid pBR322GAPRΔC1, or pBR322GAPRΔC3 was isolated. Fragment 2 was also treated with E. coli. polymerase I (Klenow fragment). The resulting blunt ended fragment was circularized by ligation and used to transform E. coli 294. One tetracycline resistant colony containing plasmid pBR322ΔRP was isolated and then digested with HindIII and SalI. The larger vector fragment (fragment 3) was isolated. The plasmid pCR160 was digested with HindIII and PstI and fragment 5 (containing the yeast PGK terminator fused to 3' prochymosin codons) was isolated. Fragments 3, 4, and 5 were joined by ligation and used to transform E. coli 294. A tetracycline resistant transformant containing plasmid pBR322GAPR$^\Delta$C1 or pBR322GAPR$^\Delta$C3 was isolated.

Figure 9:
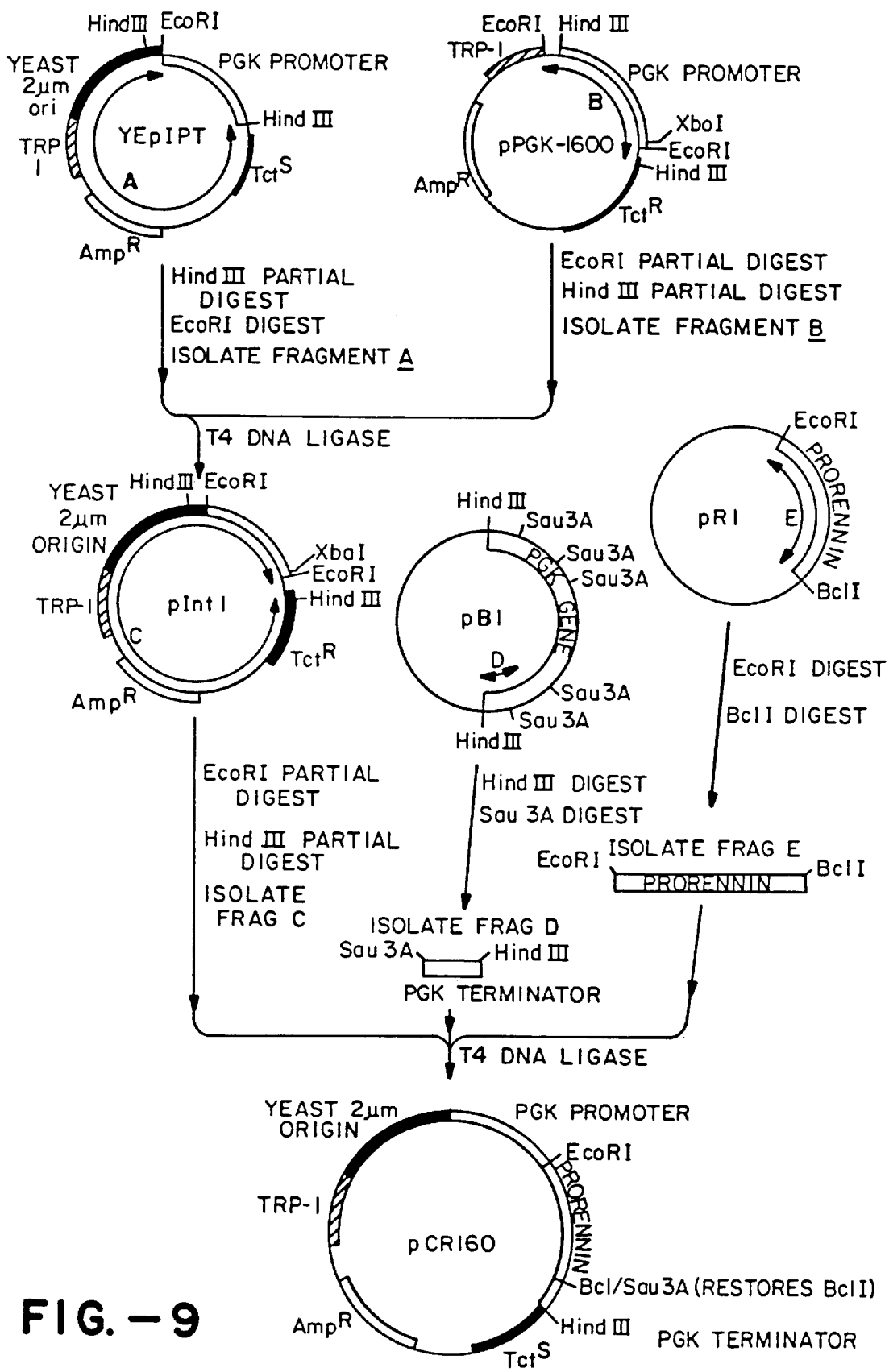
FIG. 9 depicts the construction of pCR160.

Plasmid pCR160 contains the yeast 2 μm origin of replication to allow its maintenance as a plasmid in yeast, the yeast TRP-1 gene as a yeast selection marker, an E. coli origin or replication and ampicillin resistance gene from the plasmid pBR322, and a prorennin expression unit. The prorennin expression unit contained the promoter from the yeast PGK gene, the prorennin coding region, and the terminator from the PGK gene. construction of this plasmid was accomplished as depicted in FIG. 9 in the following manner: Plasmid YEpIPT (50) was partially digested with HindIII followed by a complete EcoR1 digestion, and the vector fragment A was isolated. A second plasmid pPGK-1600 (51) was partially digested with both EcoR1 and HindIII, and the PGK promoter fragment B was isolated. Fragments A and B were ligated to give the intermediate pInt1 which was again partially digested with EcoR1 and the HindIII, and the vector fragment C was isolated. The PGK terminator fragment D was isolated following HindIII and Sau3A digestion of the plasmid pBl (52). The prorennin fragment E was isolated by cleaving pRl (49) DNA with EcoR1 and BclI. Fragments C, D, and E were then ligated to produce the yeast expression plasmid pCR160. The nucleotide sequence of the PGK promoter, structural gene and terminator have been reported (53).

Plasmids pBR322GAPRΔC1 and pBR322GAPRΔC3 contain a complete transcriptional unit for each of the forms of prochymosin. This transcriptional unit contains a precursor prochymosin coding sequence, the glucoamylase promoter, and the yeast PGK terminator. However, derivatives of these plasmids and plasmids pBR322GAPRΔC2 and pBR322GAPRΔ4, described hereinafter, [designated pInt1 (1–4) FIG. 5)] produced no detectable chymosin when used to transform A. nidulans G191. It is not understood why these derivative plasmids failed to express and secrete chymosin. However, in light of subsequent results it appears that the yeast PKG terminator and/or the short glucoamylase promotor sequence in these plasmids is not recognized by A. nidulans G191. Based on these results, the pBR322GAPRΔC plasmids were further modified.

In the following steps the transcriptional unit was moved onto the Asperaillus nidulans transformation vector pDJB3. Additional glucoamylase 5' flanking sequences were incorporated just 5' of the promoter to insure the presence of possible upstream activation sites which could be involved in regulating expression. Further, the PKG terminator was replaced with the A. niger glucoamylase terminator from pGa5. Specifically, in FIG. 5 each plasmid (pBR322GAPRΔC1 or pBR322GAPRΔC2) was digested with ClaI and fragment 6 was isolated. Plasmid pDJB3 was also digested with ClaI and treated with bacterial alkaline phosphatase in order to minimize self-ligation. This digested plasmid (fragment 7) was joined to fragment 6 and one ampicillin resistant colony containing plasmid pINTI-1 or pIntI-3 was isolated. These plasmids were digested with XhoI and NsiI and the larger vector fragment (fragment 8) was isolated. Plasmid pGa5 which contains the entire glucoamylase gene as well as extensive 5' and 3' flanking sequences was digested with XhoI and NsiI and the smaller fragment (fragment 9, containing approximately 1700 bp of these 5' sequences) was isolated. Fragments 8 and 9 were joined by ligation and used to transform E. coli 294. One ampicillin resistant colony containing plasmid pInt2-1 or plnt2-3 was isolated. These plasmids differ most significantly from the final vectors (see FIG. 7) in that they contain the yeast PGK terminator rather than the glucoamylase terminator.

Figure 6:
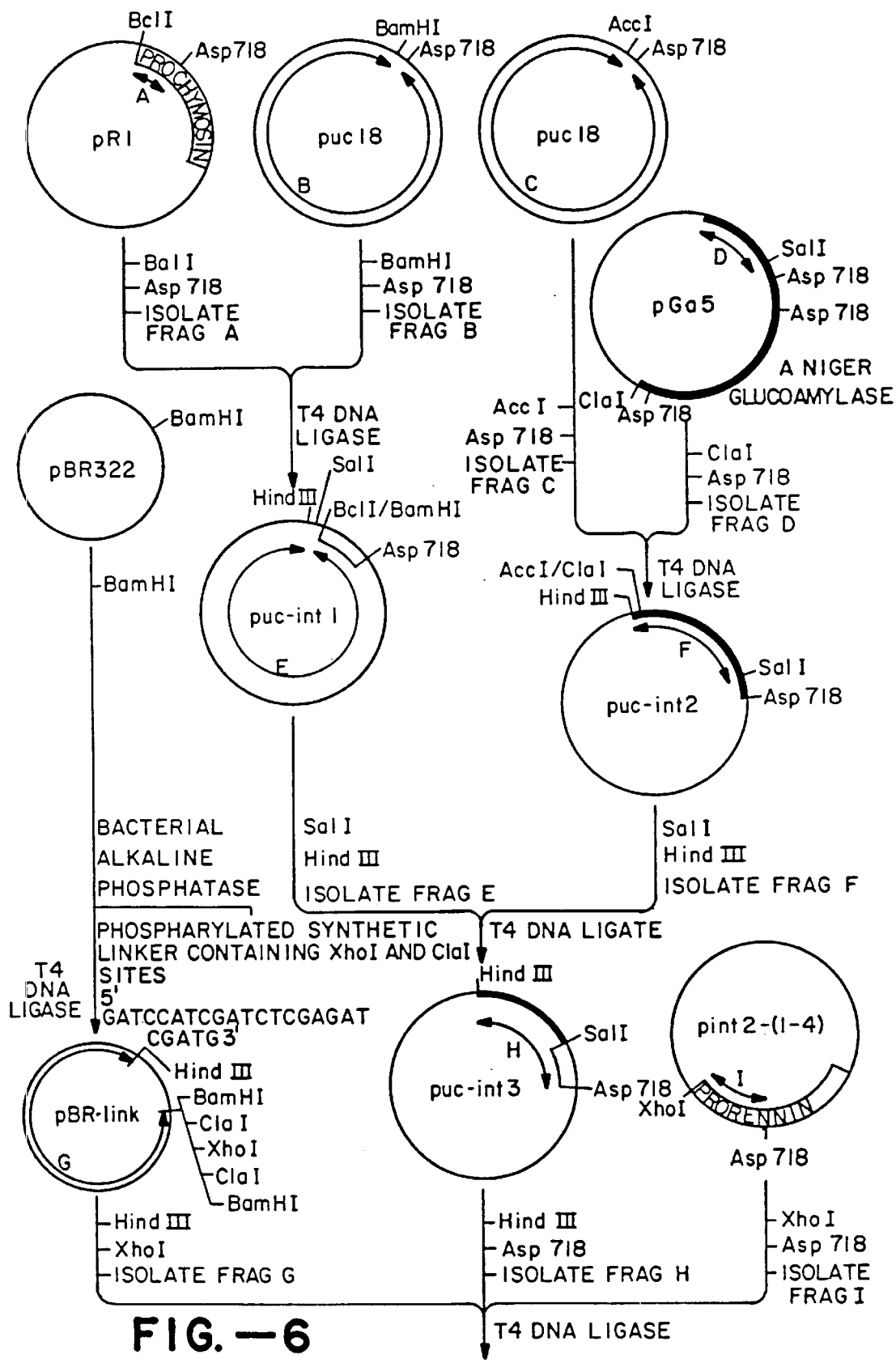
Figure 7:
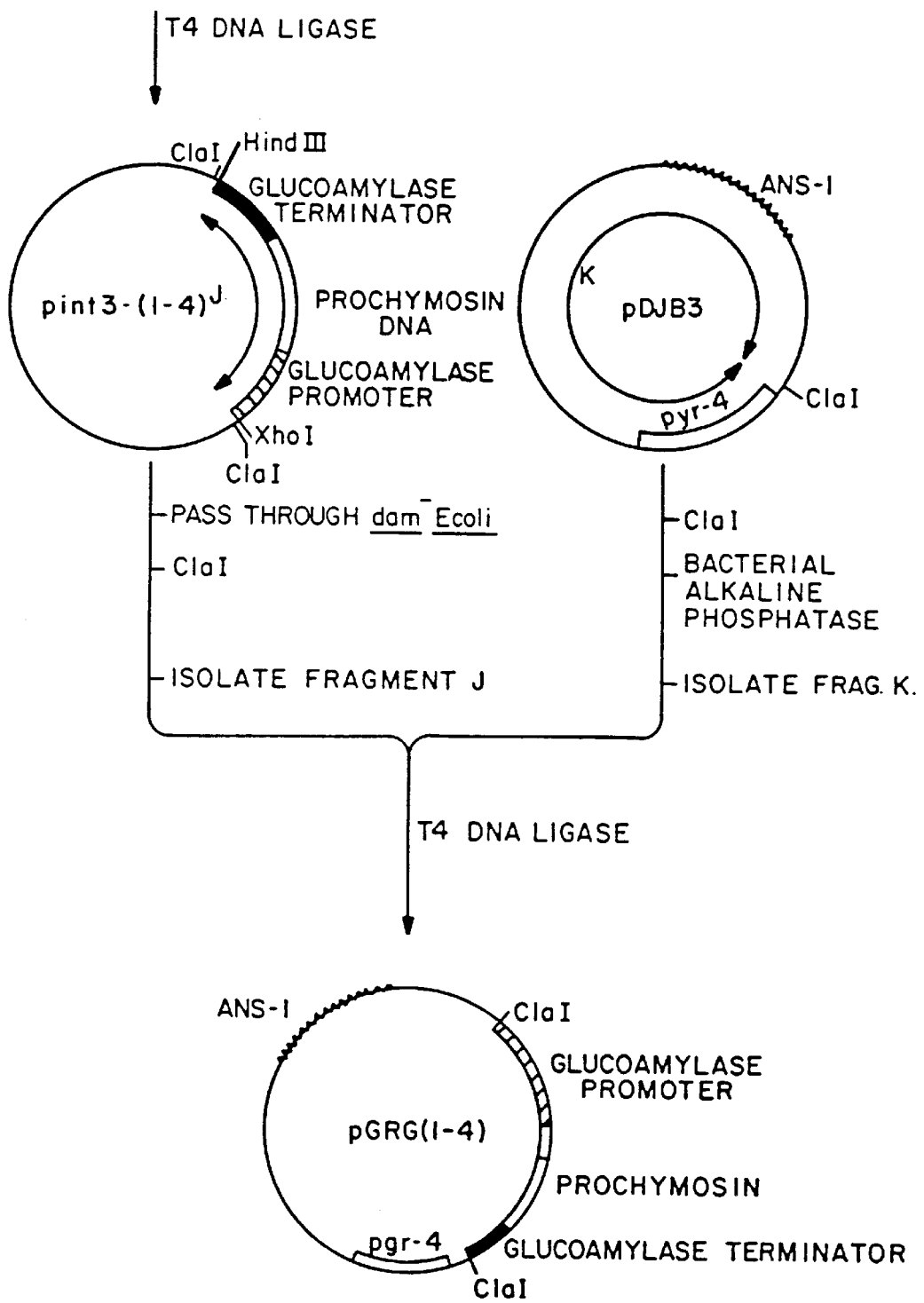

Additional steps in the construction of chymosin expression vectors are outlined in FIG. 6. Plasmid pRl (49) was used to isolate a small BclI-Asp718 DNA fragment (fragment A) which comprised the 3'- end of prochymosin cDNA. Fragment A was subsequently cloned into pUC18 (33) that was digested with Asp718 and BamHI (fragment B). Similarly, a 1.2 kb ClaI-Asp718 DNA fragment (fragment D) was isolated from plasmid pGa5, and cloned into AccI and Asp718 cleaved pUC18 (fragment C). The resulting intermediate plasmids, pUC-int1 and pUC-int2, were digested with SalI and HindIII, and fragments E and F were isolated. These fragments were then ligated to produce pUC-int3 which contained the 3' end of prochymosin followed by the glucoamylase terminator sequences on a HindIII-Asp718 fragment (fragment H).

A new cloning vector, designated pER-link, was created by inserting a synthetic oligonucleotide linker (containing XhoI and ClaI sites) into the unique BamHI site of pBR322. This linker connoted the following sequence:

5' GATCCATCGATCTCGAGATCGATC 3' (SEQ ID NO: 11)

3' GTAGCTAGAGCTCTAGCTACCTAG 5' (SEQ ID NO: 1)

The larger HindIII-XhoI fragment of this vector (fragment G) was purified by electrophoresis. Similarly, the XhoI-Asp718 restriction fragments (fragments I) of plasmids pInt2-1 and pInt2-3 were isolated electrophoretically. Fragments G and H were ligated with each of the different I-fragments in a series of three-way ligations to produce the intermediates pInt3-1 and pInt3-3. These key intermediates contained the glucoamylase promoter regions, various signal and propeptide fusions to the prochymosin (or preprochymosin) sequences followed by the glucoamylase terminator region all within convenient ClaI restriction sites. Because certain ClaI sites, such as those in the linker of pBR-link, are inhibited by E. coli. DNA methylation, the plasmids pInt3-1 through pInt3-4 were transformed into a dam-strain of E. coli, designated GM48, (ATCC 39099) from which the plasmids were re-isolated. The unmethylated DNA was digested with ClaI and fragment J was purified by electrophoresis. Fragment J from each of the glucoamylase-pro-chymosin fusions was subsequently cloned into the unique ClaI site of pDJB3 (fragment K) to produce the final expression vectors pGRG1 and pGRG3.

D. Expression and Secretion of Bovine Chymosin

Aspergillus nidulans G191 was transformed with pGRG1 and pGRG3 as previously described.

Five pGRG1 and five pGRG3 transformants were analyzed. Western analysis (not shown) indicated that each transformant secreted a protein which reacted with anti-chymosin and which migrated at the same or slightly higher molecular weight of bovine chymosin. The higher molecular weight species may be due to incorrect processing, media effects, or glycosylation. Integration was confirmed for one transformant of pGRG3 by Southern hybridization (results not shown). Each transformant was also assayed for chymosin activity. The results of this assay are shown in Table II.

TABLE II

| Transformant | No. of Transformants Tested | Range of Chymosin Activity µg/ml |
|---|---|---|
| pDJB3 | 1 | 0–0.13 |
| pGRG1 | 5 | 0–1.5 |
| pGRG3 | 5 | 0.05–7.0 |

These results indicate that pGRG2 and pGRG3 both secrete a protease, at various levels, above the pDJB3 control. occasionally, background proteolytic activity was detected in pDJB3 control broths. As will be shown hereinafter this protease activity of transformants is associated with the aspartic acid family of carboxyl proteases of which chymosin is a member.

EXAMPLE 3

Expression and Secretion of Fusion Polypeptides from *Aspergillus nidulans*

Two fusion polypeptides were constructed for expression and secretion from *A. nidulans*. One fusion polyp eptide contained an amino-terminal portion consisting of the pro sequence and first ten amino acids of *Aspergillus niger* glucoamylase and a carboxyl-terminal portion consisting of bovine prochymosin. The second fusion polypeptide contained an amino-terminal portion consisting of the pro sequence only of *Aspergillus niger* glucoamylase and a carboxyl-terminal portion consisting of bovine prochymosin.

A. Vectors for Expressing and Secreting Fusion Polypeptides

Vectors encoding the above fusion polypeptides were constructed by deleting specific sequences from mp19GAPR followed by the same manipulations as described above for constructing pGRG1 and pGRG3. As shown in FIG. 8, in mp19GAPRΔC2 the nucleotides between the glucoamylase propeptide codons and the codons of prochymosin were deleted using the site-specific mutagenesis method described above. The sequence of the oligonucleotide synthesized for this mutagenesis (primer 2) was

5' TGATTTCCAAGCGCGCTGAGATCACCAG 3' (SEQ ID NO: 12).

This mutation was intended to fuse the glucoamylase promoter, signal peptide, and propeptide codons to the first codon of prochymosin. In mp19GAPRΔC4 the nucleotide sequences between the tenth codon of mature glucoamylase and the codons of prochymosin were deleted by M13 site-specific mutagenesis with the synthetic oligonucleotide (primer 4)

5' TGAGCAACGAAGCGGCTGAGATCACCAG 3' (SEQ ID NO: 13).

This deletion fused the glucoamylase promoter region, signal peptide sequence, propeptide sequence, plus ten codons of the mature glucoamylase to the codons of pro-chymosin as shown in FIG. 8. These expression and secretion vectors designated as pGRG2 and pGRG4 were used to transform *A. nidulans*.

B. Expression and Secretion of Chymosin from *Aspergillus nidulans* Transformed with PGRG2 and PGRG4 pGRG2 and pGRG4 transformants were cultured as previously described. The culture medium was assayed for chymosin activity by Western blot and gave results similar to those obtained for pGRG1 and pGRG3. Integration of one pGRG2 transformant was confirmed by Southern Analysis (results not shown). The results of the chymosin assay are presented in Table III.

TABLE III

| Transformant | No. of Transformants Tested | Range of Chymosin Activity µg/ml |
|---|---|---|
| pDJ33 | 1 | 0–0.13 |
| PGRG2 | 1 | 0.001–0.42 |
| PGRG4 | 6 | 0.004–0.75 |

Again each of the transformants demonstrated protease activity above the pDJB3 control indicating that a protease was expressed and secreted by the transformants. As with pGRG1 and pGRG3, these proteases belong to the aspartic acid family of carboxyl proteases as evidenced by the pepstatin inhibition. Significantly, these results indicate that hybrid polypeptides have been expressed in a filamentous fungus.

EXAMPLE 4

Pepstatin Inhibition Study

Three of the above vectors containing the various constructions involving chymosin were analyzed in the pepstatin inhibition assay as described supra. The results are shown in Table IV.

TABLE IV

| Sample | Chymosin Activity (µg/ml) |
|---|---|
| pDJB3 | 0 |
| pDJB3 pepstatin | 0 |
| pGRG1 | 0.2 |
| pGRG1 pepstatin | 0.05 |
| PGRG2 | 0.1 |
| pGRG2 pepstatin | 0 |
| PGRG3 | 3 |
| pGRG3 pepstatin | 0.6 |

The samples preincubated with pepstatin show a marked decrease in activity indicating that the protease produced by the transformants is of the aspartic acid family of acid proteases to whic chymosin is a member. This data together with the results from the Western analysis indicates that biologically active chymosin is expressed and secreted by *A. nidulans* G191 transformed with pGRG1, pGRG2, pGRG3 and pGRG4.

The variation in the amount of chymosin activity detected for different vector constructions in Example II and Example III may reflect differences in the recognition of the various signals incorporated in each transformation vector. Within a particular construction, the variation in chymosin activity may be related to the copy number of the vector incorporated into the fungal genome and/or to the location of such integration.

EXAMPLE 5

Carbon Source Studies

One vector, pGRG4, was used to transform *A. nidulans* G191 which was thereafter grown on the various carbon sources previously described. The results of this assay are shown in Table V.

Table V

Amount of chymosin activity produced on various carbon sources ($\mu$g/ml)

|       | starch | glucose | fructose | sucrose |
|-------|--------|---------|----------|---------|
| pDJB3 | 0      | 0       | 0        | 0       |
| PGRG4 | 3.5    | 3.5     | 0.9      | 1.75    |

These results clearly show that chymosin is secreted regardless of the carbon source. This suggests that transcriptional regulation of the glucoamylase promotor is unlike that in *A. niger*, i.e. not strongly inducible by starch.

EXAMPLE 6

Expression and Secretion of *Mucor meihei* Carboxyl Protease

A. Carboxyl Protease Genomic Probe

The partial primary structure of *Mucor miehei* acid protease (54) was inspected for the region of lowest genetic redundancy. Residues 187–191 (using the pig pepsin numbering system), tyr-tyr-phe-trp-asp (SEQ ID NO: 14), were selected. Oligonucleotides complementary to the coding sequence corresponding to this amino acid sequence,

5'-GC(G/A)TCCCA(G/A)AA(G/A)TA(G/A)TA-3' (SEQ ID NO: 15), were synthesized (31) and labelled using gamma 32P-ATP and T4 polynucleotide kinase (30).

B. Cloning of *Mucor meihei* Carboxyl Protease

Figure 10:
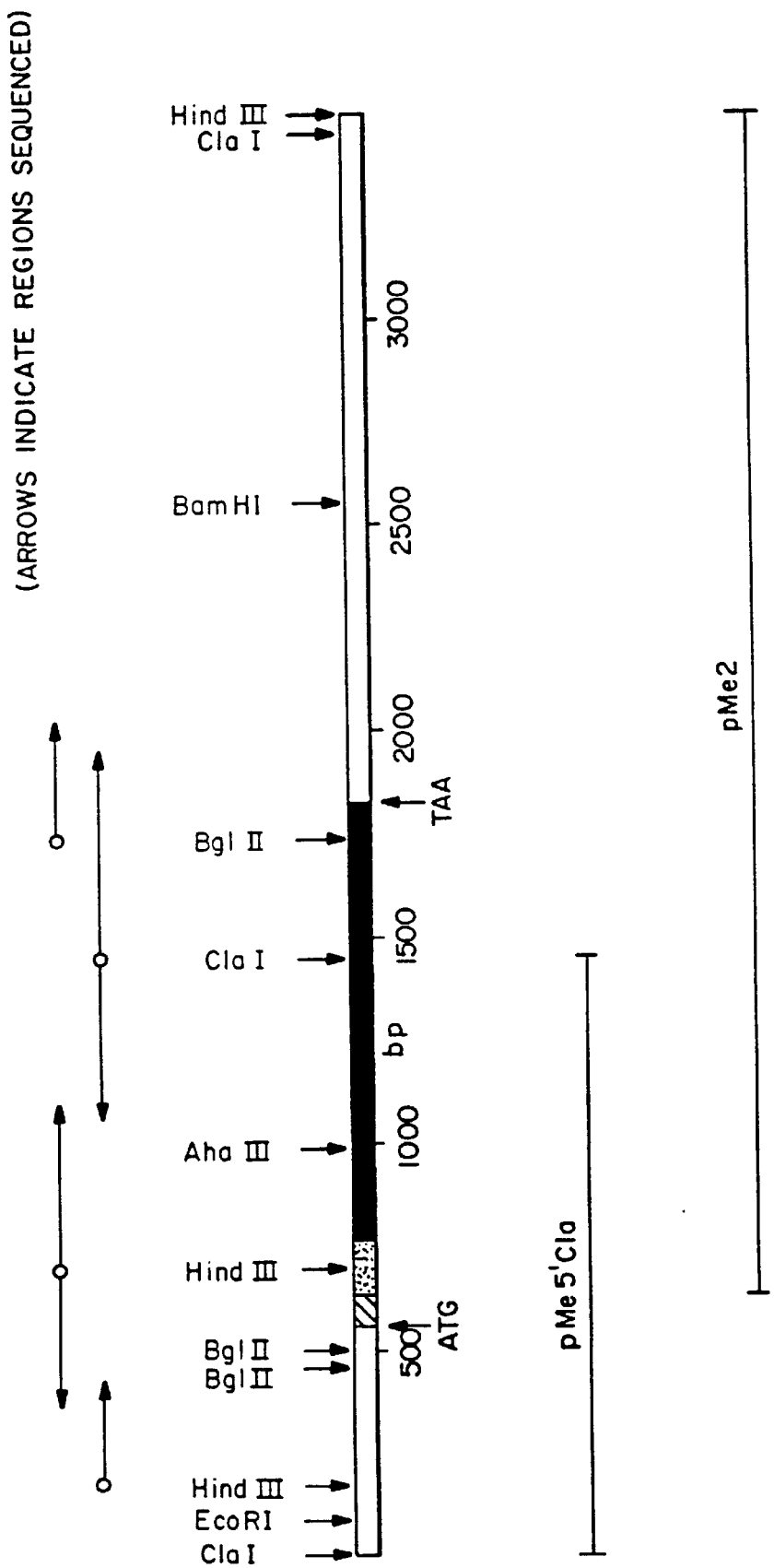
FIG. 10 is a partial restriction map of the *Mucor miehei* carboxyl protease gene including 5' and 3' flanking sequences.

Genomic DNA from *Mucor miehei* (Centraal Bureau Voor Schimmelcultures, Holland 370.75) was prepared as follows. Cells grown in YMB medium (3 g/l yeast extract, 3 g/l malt extract, 5 g/l peptone, 10 g/l glucose) were collected by centrifugation, washed twice with 0.5M NaCl, and lyophilized. Cell walls were then disrupted by adding sand to the cells and grinding the mixture with a mortar and pestle. The resulting powder was suspended (15 ml. per gram dry weight) in a solution containing 25% sucrose, 50 mM Tris-HCl (pH 8.0), and 10 mM EDTA. SDS was added to a final concentration of 0.1% and the suspension was extracted once with a half-volume of phenol and three times with half volumes of chloroform. The final aqueous phase was dialysed extensively against 10 mm Tris-HCl, pH 8.0 and 1 mM EDTA. The DNA was then precipitated by the addition of sodium acetate, pH 5.5, to a concentration of 0.3 M. followed by the addition of 2.5 volumes of cold ethanol. Aliquots of this DNA were digested with a variety of restriction endonucleases according to the manufacturers' directions and then analyzed for sequences complementary to sequences of the probes described above, using the method of Southern. A positively hybridizing band of approximately 2.5 kb (kilobases) was identified in the HindIII digested DNA. HindIII digested genomic DNA was separated by polyacrylamide gel electrophoresis and a gel fragment containing DNA of 2.0–3.0 kb was electroeluted as previously described. The electroeluted DNA, presumed to be enriched for sequences corresponding to the *Mucor miehei* acid protease gene, was ethanol precipitated. The cloning vector pBR322 (ATCC 37017) was digested with HindIII and dephosphorylated using bacterial alkaline phosphatase. In a typical 10 ul reaction 100 ng of vector and 100 mg of the size enriched DNA were joined in the presence of ATP and T4 DNA ligase. The reaction was used to transform *E. coli* 294 (ATCC 31446) by the calcium shock procedure (30). About $2.0 \times 10^4$ ampicillin resistant clones were obtained. Approximately 98% of these contained cloned inserts as indicated by their failure to grown on tetracycline containing medium. These colonies were tested by a standard colony hybridization procedure for the presence of sequences complementary to those of the DNA probes. One positively hybridizing colony, containing plasmid pMe5'muc, was found to contain a HindIII insert of the expected 2.5 kb size. The termini of this fragment were subcloned into M13 sequencing vectors (33) and their sequences determined by the dideoxy chain termination method. One terminus contained sequences corresponding to the known amino terminal amino acid sequence of the acid protease gene. The adjacent 3' region was sequenced in order to obtain more C terminal coding sequences. The sequencing strategy is shown in FIG. 10. In this way the entire coding sequence for the mature form of the protein was obtained. The 5' end of the fragment was found to occur 112 bp (base pairs) upstream of the codon corresponding the mature amino terminus. Since this upstream region contained no in frame initiation codons it was presumed to be part of a propeptide.

In order to obtain DNA containing the initiation codon as well as 5' untranslated sequences a more 5' clone was isolated as follows. A HindIII-ClaI 813 bP 5' subfragment of the pMe5'Cla Hind III insert was isolated and labelled by the nick translation method (30). This labelled fragment was used to probe ClaI digested *Mucor miehei* genomic DNA by the method of Southern. This experiment revealed a single band of hybridization corresponding to a molecular weight of approximately 1300 bp. Size enriched DNA of this size was isolated and cloned into ClaI digested and dephosphorylated pBR322 as described above.

Approximately 9000 ampicillin resistant colonies were obtained. About 90% of these contained cloned inserts as indicated by their failure to grow on tetracycline containing medium. These colonies were tested by a standard colony hybridization procedure for the presence of sequences complementary to those of the nick translated probe. One positively hybridizing colony, containing plasmid pMe2, was found to contain a ClaI insert of the expected 1.3 kb size. Sequencing of the ends of this fragment showed that one terminus corresponded to sequences near the ClaI site of the Hind III fragment in pMe5'Cla and thus permitted orientation of the fragment which is shown in FIG. 10. Further sequencing of the ClaI fragment disclosed the initiation codon and 5' untranslated sequences. The entire coding sequence and the 5' and 3' flanking sequences are shown in FIG. 10. Comparison of the deduced primary structure with that determined by direct amino acid sequencing indicates that the Mucor protein is made as a precursor with an amino-terminal extension of 69 residues. Based on the structural features generally present in leader peptides it is likely that residues −21 to −1 comprise a leader peptide and that residues 21–69 comprise a propeptide analogous to that found in the zymogen forms of other acid proteases including chymosin and pepsin (55).

C. *Mucor meihei* Carboxyl Protease Expression and Secretion Vector

A vector for expressing and secreting *Mucor miehei* carboxy protease includes the entire native *Mucor miehei* acid protease transcriptional unit including the coding sequence, 5' flanking sequences (promoter), and 3' flanking sequences (terminator and polyadenylation site).

Figure 12:
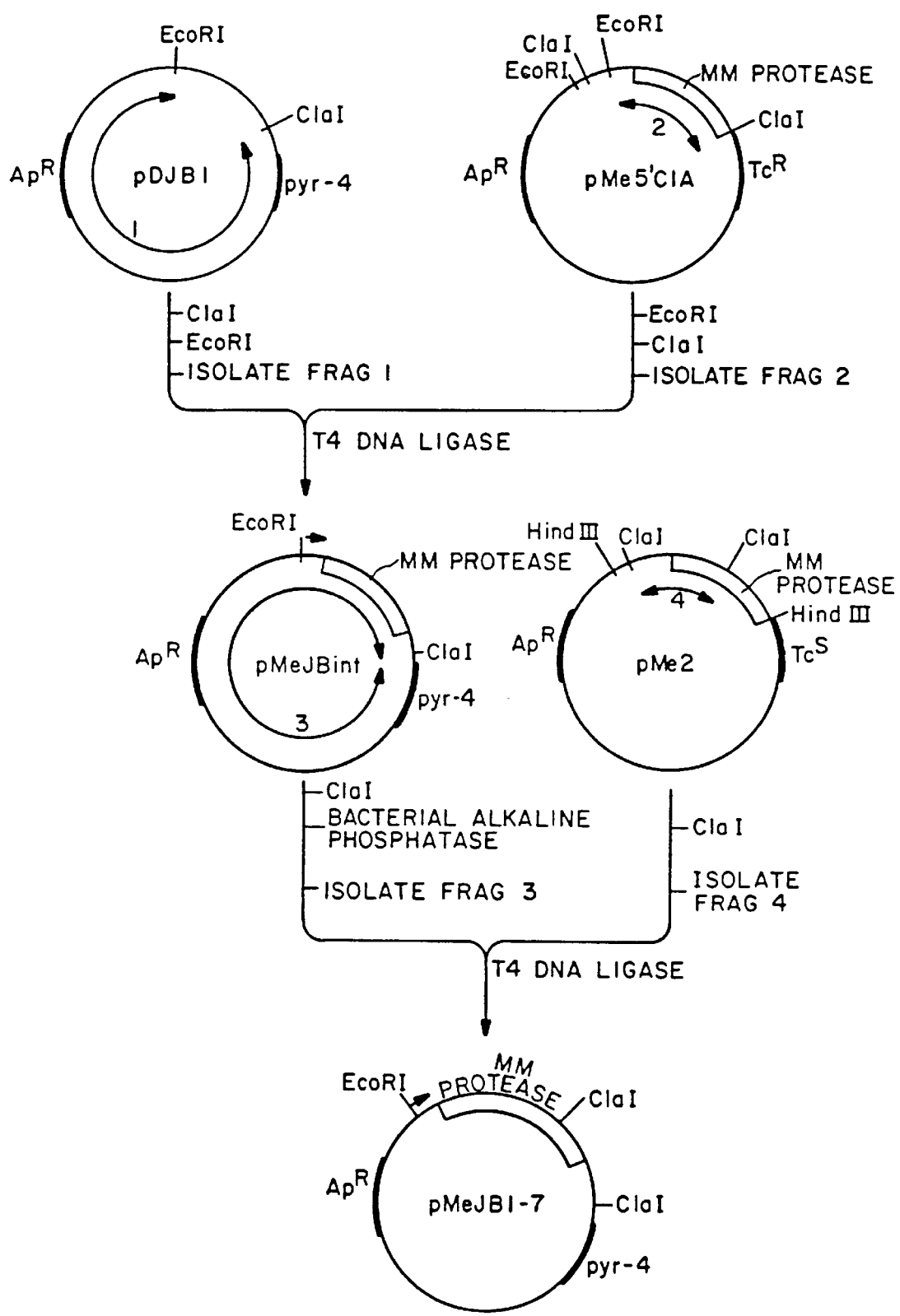
FIG. 12 depicts the construction of pMeJB1-7.

The overall strategy for making this vector is depicted in FIG. 12. The *Aspergillus nidulans* transformation vector pDJB1 was digested with ClaI and EcoR1 and the larger vector fragment (fragment 1) was isolated. The plasmid pMe5'Cla was digested with EcoR1 and ClaI and fragment 2 was isolated. This fragment contains the 5' codons of the acid protease together with about 500 bp of 5' flanking sequences. Fragments 1 and 2 were joined by ligation and used to transform *E. coli* 294. One ampicillin resistant colony containing plasmid pMeJBint was isolated. This plasmid was digested with ClaI and treated with bacterial alkaline phosphatase in order to reduce self ligation and is designated fragment 3. Plasmid pMe2 was digested with ClaI and the smaller fragment (fragment 4) was isolated. This fragment contains the *Mucor miehei* acid protease 3' codons and about 1800 bp of 3' flanking sequences. Fragments 3 and 4 were joined by ligation and used to transform *E. coli* 294. One ampicillin resistant colony containing plasmid pMeJB1-7 was isolated. This vector was used to transform *Aspergillus nidulans*.

Expression and Secretion of *Micor miehei* Carboxyl Protease by *Aspergillus nidulans*

Southern blot analysis of six transformants indicated the presece of the entire *Mucor miehei* acid protease gene in the *Aspergillus nidulans* genome (results not shown). In addition, each of the transformants were analyzed by Western blots (results not shown) and for acid protease activity. The results of the protease assay are shown Table VI.

TABLE VI

| Transformant | Protease Activity (mg/ml) |
| --- | --- |
| 1 | 0.003 |
| 2 | 0.007 |
| 3 | 0.003 |
| 4 | 0.005 |
| 5 | 0.005 |
| 6 | 0.012 |

These experiments demonstrate expression and secretion of a protein that reacts with specific antibody to *Mucor miehei* carboxyl protease and which has milk clotting activity. The protein has an apparent molecular weight by electrophoretic analysis that is slightly greater than that of the authentic (*Mucor miehei* derived) protein. This may indicate that *Aspergillus nidulans* glycosylates this glycoprotein to a different extent than *Mucor miehei*. Because the *Aspergillus nidulans* derived *Mucor meihei* acid protease appears to have the same specific activity as the authentic material it appears that it has been processed (by the cell or autocatalytically) to the mature from. The unprocessed forms of other acid protease such as chymosin and pepsin are zymogens which require processing (autocatalytic) before activityis obtained.

The varying levels of expression in the various transformants may reflect the position or copy number of the protease gene in the *Aspergillus nidulans* genome. However, the expression and secretion of biologically active carboxyl protease indicates the *A. nidulans* recognizes the promoter, signal and terminator signals of *Mucor miehei* carboxyl protease.

EXAMPLE 7

Expression and Secretion of Chymosin Encoded by pGRG1–4 from *A. awamori* and *Trichoderma reesei* pyrG Auxotrophic mutants The plasmids pGRG1 through pGRG4 (pGRG1–4) were also used to transform orotidine-5'-phosphate decarboxylase (OMPCase) deficient mutants of *A. awamori* and *Trichoderma reesei*. The pyr4 gene from *N. crassa* encoded by the pGRG1–4 plasmid complements these OMPCase mutants in the absence of uridine to permit the isolation of successful transformants. The thus transformed mutants of *A. awamori* and *T. reesei* secreted detectable amounts of bichemically active chymosin into the culture medium.

A. Production of pyrG Auxotrophs

The method used to obtain pyrG auxotrophic mutants of *A. awamori* and *T. reesei* involved selection on the pyrimidine analog 5-fluoro-orotic acid (FOA) (56). The mechanism by which FOA kills wild-type cells is unknown. However, in view of the resistance of OMPCase-deficient mutants to FOA, it is likely that the toxicity occurs through conversion of FOA to 5-fluoro-UMP. Whether cell death is caused by a flouoridated ribonucleotide or deoxyribonucleotide is uncertain.

The following methods describe the isolation of OMPCase-deficient (FOA-resistant) mutants of *T. reesei* and *A. awamori*:

1. *Trichoderma reesei*

A fresh spore suspension of *T. reesei* strain P37 (NRRL 15709) was washed three times in sterile distilled water containing 0.01% Tween-80. Fifteen milliliters of this spore suspension (1–$10^7$ spores per ml) were placed in a sterile petri dish (100×20 mm) with a sterile magnetic stirring bar. The lid was removed and the spores were exposed to ultraviolet (UV) light at 254 nm (7000 uW per cm2), in the dark at a distance of 25 cm from the UV light source. The spores were stirred constantly. UV exposure continued for three minutes (sufficient to give 70% killed spores). The irradiated spore suspension was collected in a 50 ml centrifuge tube and stored in the dark for one hour to prevent photoreactivation. Spores were pelleted by centrifugation and the pellet was resuspended in 200 ul of sterile water containing 0.01% Tween-80.

The suspension was diluted and plated onto YNB agar medium (0.7% yeast nitrogen base without amino acids, 2% glucose, 10 mM uridine, 2% agar) (56) containing 0.15% FOA (SCM Specialty Chemicals, Gainsville, Fla.). After 4 days incubation at 30° C., 75 colonies were picked to fresh YNB agar that contained FOA. Sixty-two of the 75 colonies grew and were toothpicked to minimal agar (6 g/l $NaNO_3$, 0.52 g/l KCl, 1.52 g/l $KH_2PO_4$, 1 ml/l trace elements solution, 1% glucose, 0.1% $MgSO_4$, 20 g/l agar) and minimal agar plus 1 mg/ml uridine to determine uridine requirements. All of the 62 isolates grew on minimal agar with uridine, but 9 isolates failed to grow on minimal agar alone. These 9 strains were repicked to minimal agar and minimal agar with uridine. Two of the strains grew only on minimal agar supplemented with uridine. One of these, designated *T. reesei* pyrG29, grew well on minimal medium with uridine with no background growth on minimal medium alone.

2. *Aspergillus awamori*

(i) Production of *A. awamori* Strain UVK 143f- a Hyperproducer of Glucoamylase

Spores of *A. awamori* strain NRRL 3112 were obtained after 5–7 days growth on Potato Dextrose Agar (PDA, Difco Co.) at 30° C. Spores were harvested by washing the surface of the plate with sterile 0.1% Tween-80 in distilled $H_2O$ and gently scraping the spores free. Spores were washed by centrifugation and resuspended in the same buffer to give a final concentration of between $1 \times 10^7$ to $2 \times 10^8$ spores/ml. Preparations were stored at 4° C.

Two ml of spores was added to a sterile petri plate. The top of the dish was removed and spores were exposed to an ultraviolet (UV) lamp (15 watt, germicidal). Conditions of time exposure and distance from the lamp were adjusted such that 90 to 99.9% of the spores were killed. Surviving spores were plated onto PDA medium and grown to form discrete independent colonies.

Spores from individual mutagenized colonies were inoculated into 50 ml of screening media consisting of 5% corn meal, 0.5% yeast extract, 2% corn steep liquor, adjusted to pH 4.5 prior to sterilization in 250 ml flasks. However, any number of media containing corn or corn starch as the carbon source would be expected to give similar results. Cultures were grown for 4–5 days at 30–35° C. with constant shaking. Samples were removed either daily or at the end of the run for assays.

Estimates of glucoamylase activity were made by measuring the release of a color producing group (para-nitro-phenol) from a colorless substrate (para-nitro-phenyl-alpha-glucoside, PNPAG).

The following protocol was utilized:

Substrate—180 mg PNPAG was dissolved in 250 ml of 0.1M NaAcetate buffer, pH 4.7. Store at 4° C.

Assay—1 ml of substrate was equilibrated at 40° C. in a water bath. 0.2 ml of sample (or diluted sample) was added and incubated for 30 minutes at 40° C. 9 ml of 0.1M $Na_2Co_3$ was added with the mixture being kept at room temperature for 15 minutes for color development. The mixture was filtered through Wattman 42 filter paper and the absorbance at 420 nm was read in a suitable spectrophotometer. All mutant PNPAG levels were compared to the standard amount produced by the parent strain and were reported as percent of PNPAG hyrolysis of the parent.

One glucoamylase-hyperproducing strain designated UVK 143f was selected for auxotrophic mutagenesis.

(ii) Auxotrophic Mutagenesis

Preparation of spores from *A. awamori* strain UVK143f, UV mutagenesis, and mutant analysis were the same as for *T. reesei* with the following modifications:

a. 2.5 minutes was required to give 70% killing with UV light.

b. Minimal medium was used instead of YNB agar.

c. The FOA concentration was 0.1%.

Fifteen pyrG mutants were found. Three of these isolates, designated pyr4-5, pyr4-7, and pyr4-8 were selected for transformation experiments.

B. Transformation of *A. awamori* and *T. reesei* pyr Auxotrophs

*A. awamori* and *T. reesei* auxotrophs were transformed by a modification of the procedure previously described for *A. nidulans*. Approximately $1 \times 10^8$ spores were inoculated into yeast extract glucose (YEG) medium which is 2% glucose, 0.5% yeast extract supplemented with 1 mg/ml uridine. The cultures were incubated on a 37° C. shaker (200 rpm) for 12 to 15 hours [*T. reesei* was incubated at 30° C.]. Germlings were harvested by centrifugation, washed once with sterile YEG medium, then incubated at 30° C. in 50% YEG medium containing 0.6 M KCl, 0.5% Novozyme 234 (Novo Industries, Denmark), 0.5% $MgSO_4.7H_2O$, 0.05% bovine serum albumin in a sterile 200 ml plastic bottle (Corning Corp., Corning, N.Y.). After 30 minutes of shaking at 150 rpm, the protoplast suspension was vigorously pipetted up and down five times with a 10 ml pipette to disperse the clumps. The protoplast suspension was further incubated as above for one hour then filtered through sterile miracloth (Calbiochem-Behring Corp., LaJolla, Calif.) that was wet with 0.6 M KCl. The filtered protoplasts were centrifuged, washed, and transformed with each of the plasmids pGRG1–4 as described previously.

The following modifications were made for *A. awamori* transformation:

1. 0.7 M KCl was used instead of 0.6 M KCl.
2. 1.2 M sorbitol was used instead of 0.6 M KCl to osmotically stabilize the transformation and regeneration medium.

C. Analysis of *A. awamori* and *T. reesei* Transformants

Both *A. awamori* and *T. reesei* transformants secreted chymosin polypeptides into the culture medium. This was determined by analyzing culture filtrates (results not shown) for both enzymatically active chymosin (milk clotting assay) and chymosin polypeptides that reacted with specific chymosin antibodies (enzyme immunoassays and Western immunoblotting techniques).

EXAMPLE 8

Expression and Secretion of Heterologous Polypeptides from argB Auxotrophic Mutants of Asperaillus Species The expression and secretion of heterologous polypeptides from argB auxotrophs of Aspergillus species has also been achieved.

This example describes the complementary transformation of *A. nidulans* and *A. awamori* argB auxotrophs with vectors containing the argB gene from *A. nidulans* and DNA sequences encoding the heterologous polypeptides of plasmids pGRG1–4. The argB gene encodes ornithine transcarbamylase (OTC).

The *A. nidulans* argB auxotroph containing the genetic markers biA1, argB2, metGL used herein was obtained from Dr. P. Weglenski, Department of Genetics, Warsaw University, Al. Ujazdowskie 4,00-478 Warsaw, Poland. The *A. awamori* arqB mutant was derived as follows.

A. Isolation of *Asperaillus awamori* argB Auxotrophic Mutants

A fresh suspension of *A. awamori* strain UVK 143k spores was prepared and UV mutagenesis was performed as described above except that the exposure time was sufficient to kill 95% of the spores. The spores were then centrifuged, washed with sterile water, and resuspended in 25 ml of sterile minimal medium. These suspensions were incubated in a 37° C. shaker with vigorous aeration. Under these conditions, wild-type spores will germinate and grow into vegetative mycelia, but auxotrophic mutants will not. The culture was aseptically filtered through sterile miracloth every six to eight hours for three days. This step removes most of the wild-type mycelia while the ungerminated auxotrophs pass through the miracloth filter (i.e., filtration enrichment). At each filtration step the filtered spores were centrifuged and resuspended in fresh minimal medium. After three days of enrichment the spores were diluted and plated on minimal agar supplemented with 50 mM citrulline. The plates were incubated at 37° C. for two to three days. Individual colonies were toothpicked from these plates to two screening plates—one plate that contained minimal agar plus 10 mM orhithine and one plate that contained minimal agar plus 50 mM citrulline. The rationale for picking colonies to these screening plates is as follows. OTC (the argB gene product) catalyzes the conversion of ornithine to citrulline in the arginine biosynthetic pathway. Thus argB mutants (deficient in OTC) will grow on minimal medium plus citrulline but not on minimal medium with ornithine. Screening of approximately 4000 colonies by this method yielded 15 possible argB mutants. One of these strains, designated *A. awamori* argB3, gave no background growth on minimal medium and grew very well on minimal medium supplemented with either arginine or citrulline. Assays to determine the level of OTC activity (57) indicated that the arqB3 mutant produced at least 30-fold less OTC activity than wild-type. On the basis of these data the *A. awamori* argB3 strain was selected for transformation experiments.

Figure 15:
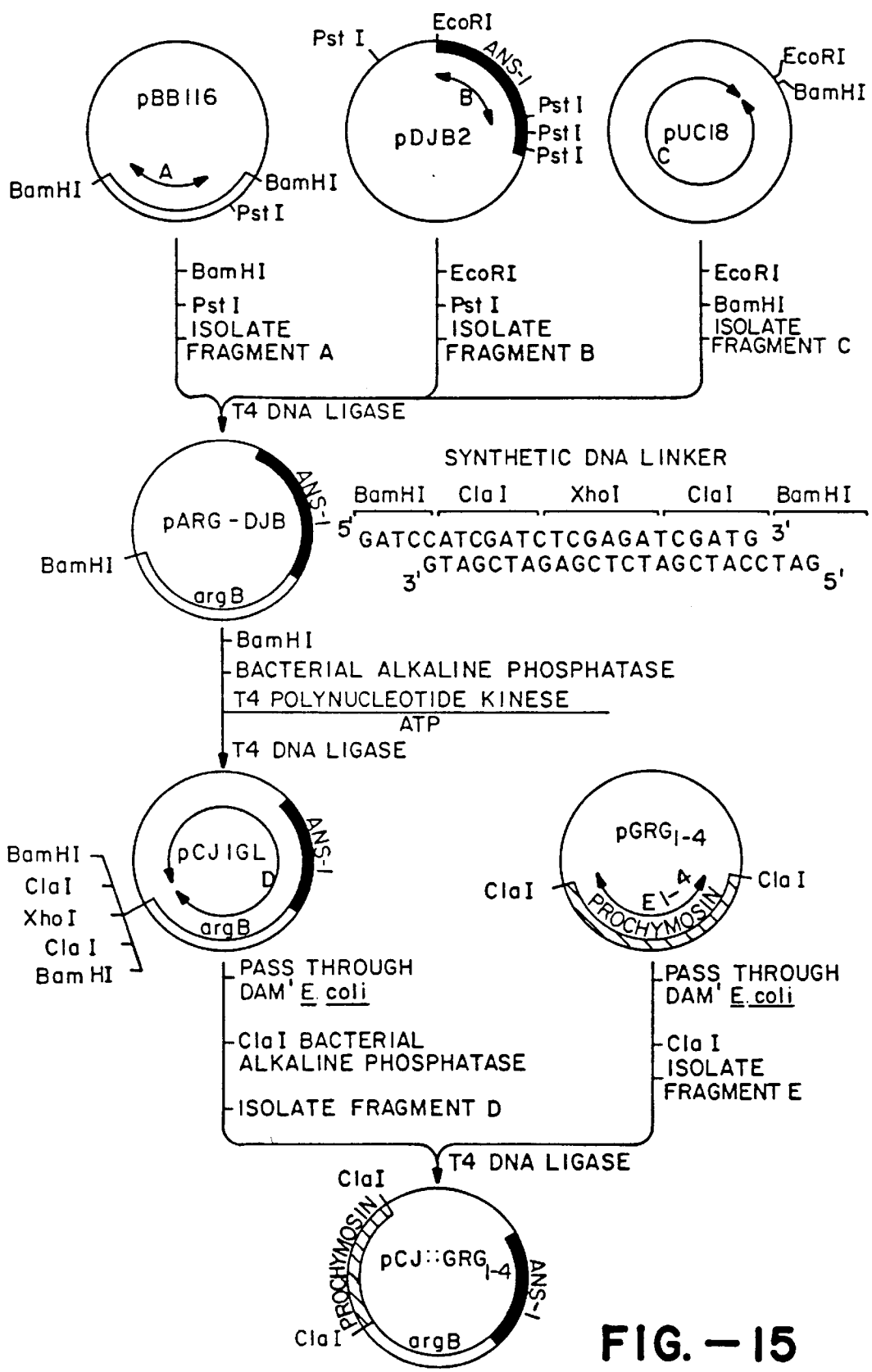
FIG. 15 (SEQ ID NO: 1)depicts the construction of plasmid pCJ:GRG1 through pCJ:GRG4.

B. Construction of argB-based Prochymosin Expression Vectors for Transformation of Aspergillus Species In this construction (see FIG. 15) the first step was to combine the transformation enhancing sequence ANS-1 and the selectable argB gene on the same plasmid. In order to achieve this, plasmid pBB116 (59), which contains the argB gene from *A. nidulans*, was digested with PstI and BamHI and the indicated fragment A, which contains the argB structural gene, was isolated. Plasmid pDJB2 (59) was digested with EcoR1 and PstI, and the indicated fragment B, which contains the ANS-1 sequence, was isolated. In a three part ligation fragments A and B were joined together with fragment C, which contains the large EcoR1-BamHI fragment of plasmid vector pUCis (33) to give plasmid PARG-DJB.

In the second step of this construction a synthetic DNA polylinker containing ClaI sites was inserted into PARG-DJB in order to allow the insertion of ClaI fragments which contain various prochymosin expression units. Plasmid PARG-DJB was digested with BamHI and then dephosphorylated with bacterial alkaline phosphatase. The indicated synthetic DNA polylinker was phosphorylated with T4 polynucleotide kinase, and then ligated to the cleaved PARG-DJB to give pCJ16L. Because this plasmid was found to be resistant to digestion with ClaI, it was first used to transform the *E. coli* dam- mutant strain GM48 in order to prevent methylation of the ClaI sites. Upon isolation of the plasmid from GM48 transformants, it was successfully cleaved with ClaI and dephosphorylated with bacterial alkaline phosphatase.

In the final step of this construciton of ClaI-cleaved pCJ16L vector was joined to each of the ClaI prochymosin expression fragments from plasmids pGRG1 through pGRG4. The resulting four plasmids, pCJ::GRG1 through pCJ::GRG4, were used to transform the argB mutants of *A. nidulans* and *A. awamori* to prototrophy. Resulting transformants were analyzed for expression of prochymosin polypeptides.

C. Analysis of *A. nidulans* and *A. awamori* transformants

Secreted chymosin polypeptides from *A. awamori* and *A. nidulans* transformed with pCJ::GRG1 through pCJ::GRG4 were detected by the milk clotting assay and by enzyme immunoassays and Western immunoblotting techniques. In each case (results not shown) the transformed fungi secreted biochemically active chymosin into the culture medium.

EXAMPLE 9

Expression and Secretion of *Humicola grisea* Glucoamylase from *A. nidulans*

The glucoamylase gene from the fungus *Humicola grisea* was isolated and cloned. This gene was thereafter ligated into the argB expression plasmid pCJ16L. The resulting vectors, pCJ:RSH1 and pCJ:RSH2 were used to transform argB deficient *A. nidulans* (Example 8) which resulted in the expression and secretion of Humicola arisea glucoamylase.

A. Isolation and Cloning of *Humicola grisea* Glucoamylase Gene

1. Purification of *Humicola grisea* Glucoamylase

Authentic *H. arisea* (var. *thermoidea* NRRL 15219) glucoamylase was obtained from A.E. Staley Company (lot no. 1500-149-8A). The enzyme was purified to homogeneity through chromatography on a 4.6 mm×250 mm Synchrompak C4 reversed phase column (SynChrom, Inc., Linden, Ind.). The column was initially equilibrated with 0.05% triethylamine and 0.05% trifluoroacetic acid (solvent A) at 0.5 ml/min. After injection of the glycomaylase sample (40 μg) the column was washed for 2 minutes with solvent A, and then eluted with a gradient of 5% solvent B per minute (solvent B is 0.05% triethylamine, 0.05% trifluoroacetic acid in acetonitrile) to 40% solvent B. The slope of the gradient was then changed to 0.5% solvent B per minute, and the glucoamylase was eluted at approximately 55% solvent B. At this point the glucoamylase was judged to be homogenous by sodium dodecylsulfate polyacrylamide gel electrophoresis.

2. Amino Acid Sequence of *H. grisea* Glucoamylase

The amino terminal sequence of purified *H. grisea* glucoamylase was obtained as described previously (60). The sequence read as follows:

AAVDTFINTEKPSAXNSL (SEQ ID NO: 16).

These and other lettered peptide sequences presented herein refer to amino acid sequences wherein each letter corresponds to the following amino acids:

| Amino acid or residue thereof | 3-letter symbol | 1-letter symbol |
|---|---|---|
| Alanine | Ala | A |
| Glutamate | Glu | E |
| Glutamine | Gln | Q |
| Aspartate | Asp | D |
| Asparagine | Asn | N |
| Leucine | Leu | L |
| Glycine | Gly | G |
| Lysine | Lys | K |
| Serine | Ser | S |
| Valine | Val | V |
| Arginine | Arg | R |
| Threonine | Thr | T |
| Proline | Pro | P |
| Isoleucine | Ile | I |
| Methionine | Met | M |
| Phenylalanine | Phe | F |
| Tyrosine | Tyr | Y |
| Cysteine | Cys | C |
| Tryptophan | Trp | W |
| Histidine | His | H |

In order to obtain peptide fragments for additional amino acid sequencing, purified glucoamylase (1 mg/ml) was digested in 2% acetic acid for 2 hours at 108° C. The material was injected directly onto a Synchrompak C4 column (4.8 mm×100 mm) equilibrated as described above. After washing for 2 minutes with 100% solvent A (see above), the peptides were eluted with a linear gradient of solvent C (1% per minute). Solvent C was composed of 0.05% triethylamine, 0.05% trifluoroacetic acid in propanol. At this point three peptides were selected for further analysis. One peptide (GA3) was sequenced directly. A mixture of two other peptides (GA1 and GA2) was subjected to further purification on a 4.8 mm×250 MM Synchrompak C4 column as follows. The mixture of GA1 and GA2 was diluted with three volumes of solvent A and injected onto the column. After washing for 2 minutes, the peptides were eluted with a linear gradient of solvent D (0.5% per minute). Solvent D was 0.05% triethylamine, 0.05% trifluoroacetic acid in 9% propanol: 65% acetonitrile. Separated GA1 and GA2 were then purified again using the same protocol and the amino acid sequences were determined as described above. The sequences of peptides GA1, GA2 and GA3 are as follows:

GA1 PLWSITVPIKATGXAV<u>OYKYIK</u>VXQL (SEQ ID NO: 17)

GA2 AAVRPLINPEKPIAWNXLKANIGPN (SEQ ID NO: 18)

GA3 INTEKPIAWNKLLANIGPNGKAAP-
GAAAGVVIASPSRTD (SEQ ID NO: 19)

The genomic DNA encoding the *H. grisea* glucoamylase gene was cloned as follows. A synthetic mixture of 48 oligonucleotides was used as a hybridization probe to detect the glucoamylase gene. The oligonucleotides were 17 bases in length (17mer) and corresponded to a sequence of six amino acids (underlined in the GA1 peptide, supra) from *H. grisea* glucoamylase:

```
   GlnTyrLysTyrIleLys  (SEQ ID NO: 21)
5'CAATATAAATATATTAA 3'  (SEQ ID NO: 20)
   G   C  G   C   C
                  A
```

The mixture of 48 oligonucleotides was synthesized in six pools, each containing eight different synthetic 17 mers.

```
pool 1:  5'CAATATAAATATATTAA 3'    (SEQ ID NO: 22)
              G   C  G pool 2:  5'CAATATAAATACATTAA 3'    (SEQ ID NO: 23)
              G   C  G pool 3:  5'CAATATAAATATATCAA 3'    (SEQ ID NO: 24)
              G   C  G pool 4:  5'CAATATAAATACATCAA 3'    (SEQ ID NO: 25)
              G   C  G pool 5:  5'CAATATAAATATATAAA 3'    (SEQ ID NO: 26)
              G   C  G pool 6:  5'CAATATAAATACATAAA 3'    (SEQ ID NO: 27)
              G   C  G
```

The oligonucleotides were synthesized on a Biosearch automated DNA synthesizer (Biosearch, San Rafael, Calif.) using reagents and protocols specified by the manufacturer.

4. Selection of Correct Oligonucleotide Probe

Genomic DNA from *H. grisea* was analyzed for the presence of glucoamylase sequences by the method of Southern (30). Briefly, *H. grisea* DNA was digested with BamHI restriction endonuclease. Six aliquots of this digested DNA (one for each probe pool) were fractionated according to size by electrophoresis on a 1% agarose gel. After blotting the DNA to nitrocellulose, as previously described, the DNA was fixed to the nitrocellulose filter at 80° C. in a vacuum oven. The filter was cut into six strips, corresponding to the six aliquots of BamHI digested DNA, and each strip was hybridized for 18 hours at low stringency (2, 40) with one of the pools of synthetic oliconucleotide probes. (The probes were radiolabeled with gamma-[32P] ATP using T4 polynucleotide kinase as previously described.) After hybridization, the filters were washed 15 minutes in 2×SSC, 0.1% SDS at 37° C., and twice in 2×SSC at the same temperature. Filters were air dried, wrapped in Saran-Wrap, and applied to Kodak XOmat-AR X-ray film to obtain an autoradiographic image. After developing the autoradiogram, a faint band of hybridization corresponding to a 3.7 Kb BamHI fragment was visible from the strip that was hybridized with pool 3.

In order to improve the hybridization signal, pool 3 was resynthesized as eight individual oligonucleotides. The Southern hybridization experiments were repeated using each of the eight oligonucleotides as probes. Only one of these 17 mer probes was found to hybridize to the 3.7 Kb BamHI fragment of *H. grisea* genomic DNA. The sequence of the oligonucleotide was 5' CAGTACAAGTATATCAA 3' (SEQ ID NO: 28). This 17 mer was used as the hybridization probe for the cloning of the *H. grisea* glucoamylase gene.

5. Cloning of Glucoamylase Gene Seauences

Genomic DNA from *H. grisea* was digested with BamHI and size-fractionated by polyacrylamide gel electrophoresis according to standard methods (30). DNA fragments 2 to 4 Kb in size were excised and eluted from the gel. This DNA fraction was used to generate a library of clones in the *E. coli* cloning vector pBR322 (ATCC 37017). The cloning vector was digested with BamHI and dephosphorylated with bacterial alkaline phosphatase. The phosphatase was removed by extraction with phenol-chloroform (1:1 v/v). The BamHI cleaved size-selected *H. grisea* DNA was ligated to the BamHI cleaved and dephosphorylated pBR322. The thus ligated DNA was used to transform competent *E. coli* 294 cells (ATCC 31446) prepared by the method of Morrison (41). Transformants were selected on LB agar plates (30) which contained carbenecillin at a concentration of 50 µg/ml. Transformants which harbored glucoamylase gene sequences were identified by colony hybridization methods (30) using the specific 17mer (described above) as a probe. Hybridizing colonies were purified, and plasmids were isolated from each by the alkaline-SDS miniscreen procedure (30). The plasmids selected in this manner all contained a 3.7 Kb BamHI fragment which hybridized to the glucoamylase-specific 17mer probe. One such plasmid, designated pRSH1, was selected for further analysis.

Figure 16:
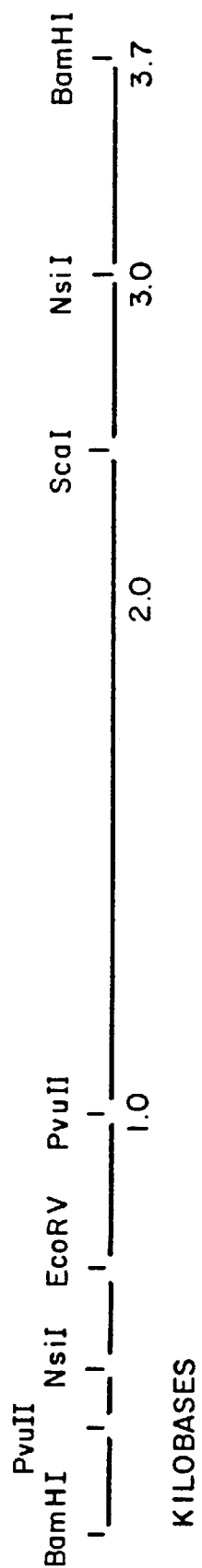
FIG. 16 depicts a restriction endonuclease cleavage map of the 3.7 Kb BamHI fragment from pRSH1.

A 600 bp Sau3A fragment from pRSH1 was subcloned into bacteriophage M13mp 18(33) and partially sequenced by the dideoxy chain termination method (43) to confirm that the cloned DNA encoded the glucoamylase gene. A restriction endonuclease cleavage map of the 3.7 Kb BamHI fragment contained in pRSH1 is shown in FIG. 16. It was generated following single and double restriction digests followed by orientation of the DNA fragments with respect to known restriction sites in pBR322 (44). On the basis of the DNA sequencing data we obtained and the restriction map, we determined that there was a high probability that the entire coding sequence of the glucoamylase gene was contained within the 3.7 Kb BamHI fragment in pRSH1.

B. Construction of arqB Vector Containing *Humicola grisea* Glucoamylase Gene

Figure 17:
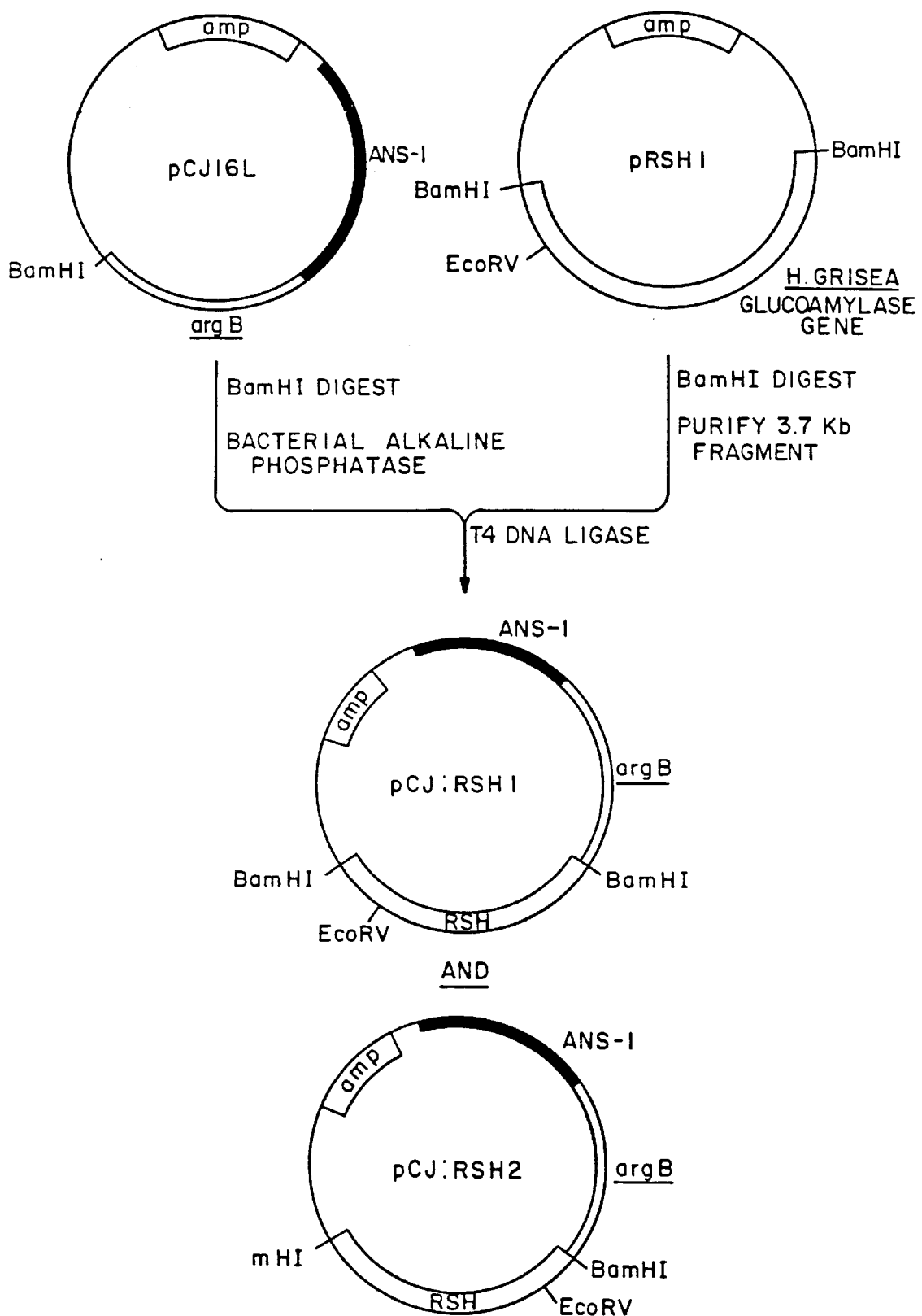
FIG. 17 depicts the construction of pCJ:RSH1 and pCJ:RSH2.

The 3.7 Kb BamHI fragment from pRSH1 was cloned (in both orientations) into pCJ16L which contains a selectable argB gene from *A. nidulans* (FIG. 17). The resulting vectors, PCJ:RSH1 and pCJ:RSH2, were used to transform argB-deficient *A. nidulans*.

C. Expression and Secretion of *H. grisea* Glucoamylase

Figure 18:
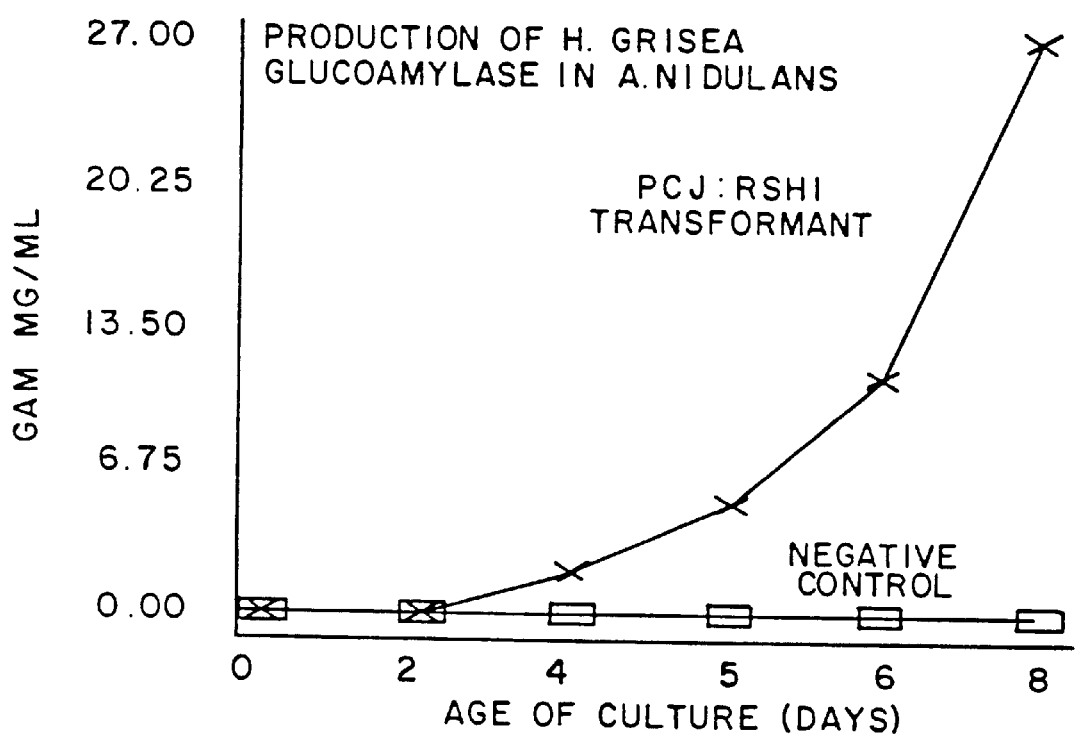
FIG. 18 depicts the expression of *H. grisea* glucoamylase from *A. nidulans*.

Prototrophic transformants were purified and innoculated into minimal medium with starch as the sole carbon source (this medium is the same as that described for the production of chymosin except that the pH was adjusted to 5.0). Culture filtrates were assayed for *H. grisea* glucoamylase activity. FIG. 18 shows the extracellular production of *H. grisea* glucoamylase by *A. nidulans* transformed with pCJ:RSH1. The negative control was non-transformed argB deficient *A. nidulans*.

Although the foregoing refers to particular preferred embodiments, it will be understood that the present invention is not so limited. It will occur to those ordinarily skilled in the art that various modifications may be made to the disclosed embodiments and that such modifications are intended to be within the scope of the present invention.

The references grouped in the following bibliography and respectively cited parenthetically by number in the foregoing text, are hereby incorporated by reference.

BIBLIOGRAPHY

1. Hitzeman, R. A., et al., 1984. In *Recombinant DNA Products: Insulin-Interferon-Growth Hormone*, A. P. Bollon, ed., CRC Press, Boca Raton, Fla.; Goeddel, D. V. et al., 1979. *Nature*, 281: 544–548.
2. Haynes, J. et al., 1983, *Nucleic Acids Res.*, 11:687–706; Pennica, D. et al., 1983, *Nature*, 301:214–221.
3. Lawn, R., et al., 1981, *Nucl. Acids Res.*, 9:6103–6114.

4. Wood, W. I., et al., 1984, *Nature*, 312:330–337.
5. Heyneker, H. L. et al., European Patent Office Publication No. 0092182 published Oct. 26, 1983.
6. Tuite, M. F., et al., 1982, *EMBO J.*, 1:603–608.
7. Mellor, J., et al., 1982, *Gene*, 24:1–14.
8. Sibakov, M., et al., 1983, *FEMS Microbiol Lett.*, 17:81–85.
9. Wells, J. A., et al., 1982, *Nucl. Acids Res.*, 11:7911–7925.
10. Baty, D., et al., 1981, *Gene*, 16:79–87.
11. Sibakov, M., et al., 1984, *Genetics and Biotechnology of Bacilli*, A. T. Ganesan and J. A. Hoch, eds., Academic Press, NY.
12. Edens, L., et al., 1984, European Patent Office Publication No. EP0129268A2.
13. Marston, F. A. O., et al., 1984, *Biotechnol.*, 2:800–804.
14. Foltmann, B., et al., 1979, *J. Biol. Chem.*, 254:8447–8456.
15. Hayenga, K. J., et al., 1984, European Patent Application EP0114507.
16. Case, M. E., et al., 1979, *Proc. Natl. Acad. Sci. USA*, 76:5259–5263; and Lambowitz U.S. Pat. No. 4,486,533.
17. Kinsey, J. A. and J. A. Rambosek, 1984, *Molecular and Cellular Biology* 4:117–122.
18. Yelton, M., et al., 1984, *Proc. Natl. Acad. Sci. USA*, 81:1470–1474; Mullaney, E. J. et al., 1985, *Mol. Gen. Genet.*, 199:37–45.
19. John, M. A. and J. F. Peberdy, 1984, *Enzyme Microb. Technol.*, 6:386–389.
20. Tilburn, et al., 1982, *Gene*, 26:205–221.
21. Ballance, D. J., et al., 1983, *Biochem. Biophys. Res. Comm*, 112:284–289.
22. Kelly, J. M. and M. Hynes, 1985, *EMBO*, 4:475–479.
23. Bull, J. H. and J. C. Wooton, 1984, *Nature*, 310:701–704.
24. Barclay, S. L. and E. Meller, 1983, *Molecular and Cellular Biology*, 3:2117–2130.
25. Ingolia, P. L., et al., 1984, p. 28, ASM Conf., *Genet. and Mol. Bio. Ind. Microorganisms*, (Abstr.)
26. Alexopoulos, C. J., 1962, Introductory Mycology, John Wiley & Sons, Inc., New York.
27. Innis, M. A., et al., 1985, *Science*, 228:21–26
28. Penttila, M. E., et al., 1984, *Mol. Gen. Genet.*, 194:494–499.
29. Shoemaker, S. P., et al., 1984, European Patent Application EPO137280A1.
30. Maniatis, T., et al., 1982, *Molecular Cloning*, Cold Spring Harbor Press, Cold Spring Harbor, NY.
31. Crea, R., et al., 1978, *Proc. Natl. Acad. Sci. USA*, 75:5765–5769.
32. Buxton, F. and Radford A., 1983, *Mol. Gen. Gent.*, 190:403–405.
33. Yanisch-Perron, C., Vieira, J., and Messing, J., 1985, *Gene*, 33:103–119.
34. Clutterbuck, J. H., 1974, *Aspergillus nidulans*, In: *Handbook of Genetics*. King, R. C. ed., p. 447–510, Plenum Press, New York.
35. Towbin, H., et al., 1979, *Proc. Natl. Acad. Sci. USA*, 76:4350–4354.
36. Uchiyama, H., et al., 1981, *J. Biochem*, 90:483–487.
37. Sokol, P. A., et al., 1979, *J. Clin. Microbiol.*, 9:538–540.
38. Pollock, M. R., 1961, *J. Gen. Microbiol.*, 26:239–253.
39. Nunberg, J. H., et al., 1984, *Mol. Cell. Biol.*, 4:2306–2315.
40. Adelman, J. P., et al., 1983, DNA, 2:183–193.
41. Morrison, D. A. 1979, Methods Enzymol., 68:326–331.
42. Messing, J., 1983, *Methods Enzymol.*, 101:20–78.
43. Sanger, F., et al., 1977, *Proc. Natl. Acad. Sci. USA*, 74:5463–5467.
44. Bolivar, F., et al., 1977, *Gene*, 2:95–113.
45. Bolivar, S., 1978, *Gene*, 4:121–136.
46. Wallace, R. B., et al., 1981, *Nucl. Acids Res.*, 9:3647–3656.
47. Nunberg, J. H., et al., 1984, International Patent Publication No. WO84/020921. 48. Boel, E., et al., 1984, *EMBO J.*, 3:1581–1585.
49. European Patent Office Publication No. 0116778 published Aug. 29, 1984.
50. Hitzeman, R. A., et al., 1983, *Science*, 219:620–625.
51. Hitzeman, R. A., et al., 1983, *Nucl. Acids Res.*, 11:2745–2763.
52. Hitzeman, R. A., et al., 1980, *J. Biol. Chem.*, 255:12073.
53. Hitzeman, R. A., et al., 1982, *Nucl. Acids Res.*, 10:7791–7808.
54. Bech, A. M. and Foltmann, B., 1981, *Neth. Milk Dairy J.*, 35:275–280.
55. Foltmann, B. and Pedersen, V. B., 1977, pp. 3–22, In: *Acid Proteases*, J. Tang, ed., Plenum Press, NY.
56. Boeke, J. D., et al., 1984, *Mol. Gen. Genet.*, 197:345–346.
57. Basabe, J. R., et al., 1979, *Anal. Biochem.*, 94:356–360.
58. Berse, B., et al., 1983, *Gene*, 25:109–117.
59. Balance, D. J., et al., 1985, *Gene*, 36:321–331.
60. Rodriguez, H., et al., 1984, *Anal. Biochem.*, 134:538–547.
61. Johnston, I. L., et al., 1985, *EMBO J.*, 4:1307–1311.

What is claimed is:

1. A filamentous fungus capable of expressing and secreting a hetefoloous polypeptide.

2. The filamentous fungus of claim 1 wherein a DNA sequence encoding said heterologous polypeptide is integrated into the genome of said filamentous fungus.

3. The filamentous fungus of claim 1 wherein said filamentous fungus is selected from the group consisting of Aspergillus species, Trichoderma species and Mucor species.

4. The filamentous fungus of claim 1 wherein said filamentous fungus is *A. nidulans* or *A. awamori*.

5. The filamentous fungus of claim 1 wherein said filamentous fingus is *Trichoderma reesei*.

6. The filamentous fungus of claim 1 wherein said heterologous polypeptide is an enzyme selected from the group consisting of chymosin, prochymosin, preprochymosin, *A. niger* glucoamylase, *Humicola grisea* glucoamylase and *Mucor mehei* carboxyl protease.

7. The filamentous fungus of claim 1 wherein said secreted heterologous polypeptide is a mammalian polypeptide.

8. The filamentous fungus of claim 1 wherein said secreted heterologous polypeptide is biochemically active.

9. A process for making a heterologous polypeptide comprising:

transforming a filamentous fungus with a vector containing DNA sequences capable of expressing a heterologous polypeptide and of causing secretion of said heterologous polypeptide from said filamentous fungus, and expressing and secreting said heterologous polypeptide.

10. The process of claim 9 wherein said expressing and secreting is carried out in a culture medium comprising utilizable carbon, nitrogen and phosphate sources, surfactant and trace elements.

11. The process of claim 9 further comprising the step of isolating said secreted heterologous polypeptide.

12. The process of claim 9 wherein said secreted heterologous polypeptide is an enzyme selected from the group consisting of chymosin, prochymosin, preprochymosin, *A. niger* glucoamylase, *Humicola grisea* glucoamylase and *Mucor mehei* carboxyl protease.

13. The process of claim 9 wherein said secreted heterologous polypeptide is a mammalian polypeptide.

14. The process of claim 9 wherein said secreted heterologous polypeptide is biochemically active.

* * * * *

UNITED STATES PATENT AND TRADEMARK OFFICE
CERTIFICATE OF CORRECTION

PATENT NO. : 6,379,928 B1
DATED : April 30, 2002
INVENTOR(S) : Berka, Randy Michael et al.

It is certified that error appears in the above-identified patent and that said Letters Patent is hereby corrected as shown below:

Column 45,
Line 53, after "secreting a" and before "polypeptide.", please delete "hetefoloous" and instead insert -- heterologous --.

Signed and Sealed this

Twelfth Day of November, 2002

JAMES E. ROGAN
Director of the United States Patent and Trademark Office